(12) United States Patent
Ginn

(10) Patent No.: US 12,115,076 B2
(45) Date of Patent: Oct. 15, 2024

(54) SACROILIAC JOINT STABILIZATION PROSTHESES

(71) Applicant: Tenon Medical, Inc., Los Gatos, CA (US)

(72) Inventor: Richard S Ginn, Gilroy, CA (US)

(73) Assignee: Tenon Medical, Inc., Los Gatos, CA (US)

( * ) Notice: Subject to any disclaimer, the term of this patent is extended or adjusted under 35 U.S.C. 154(b) by 627 days.

(21) Appl. No.: 17/469,132

(22) Filed: Sep. 8, 2021

(65) Prior Publication Data

US 2021/0401581 A1 Dec. 30, 2021

Related U.S. Application Data

(63) Continuation of application No. 17/463,831, filed on Sep. 1, 2021, which is a continuation-in-part of
(Continued)

(51) Int. Cl.
*A61F 2/44* (2006.01)
*A61B 5/055* (2006.01)
(Continued)

(52) U.S. Cl.
CPC .......... *A61F 2/30988* (2013.01); *A61B 5/055* (2013.01); *A61B 5/062* (2013.01); *A61B 6/032* (2013.01); *A61B 6/485* (2013.01); *A61B 8/0841* (2013.01); *A61B 17/1604* (2013.01); *A61B 17/1664* (2013.01); *A61B 17/1671* (2013.01);
(Continued)

(58) Field of Classification Search
CPC .. A61F 2002/30121; A61F 2002/30123; A61F 2002/3013; A61F 2002/30138; A61F 2002/30197; A61F 2002/30215; A61F 2002/30166; A61F 2002/30227; A61F 2002/30878; A61F 2002/30883; A61F 2002/30884; A61F 2002/30995; A61F 2/4455; A61B 17/0642
See application file for complete search history.

(56) References Cited

U.S. PATENT DOCUMENTS 4,444,181 A * 4/1984 Wevers .............. A61B 17/8019
606/75
4,501,269 A * 2/1985 Bagby ...................... A61D 1/00
606/279
(Continued)

FOREIGN PATENT DOCUMENTS

WO WO-2010045749 A1 * 4/2010 ......... A61B 17/1617

*Primary Examiner* — Lynnsy M Summitt
(74) *Attorney, Agent, or Firm* — Francis Law Group

(57) ABSTRACT

Prostheses are described for stabilizing dysfunctional sacroiliac (SI) joints. The prostheses are sized and configured to be press-fit into surgically created pilot SI joint openings in dysfunctional SI joint structures. The prostheses include a fixation composition that is adapted to transition from a flowable state, wherein the fixation composition flows into spaces between the prostheses and the dysfunctional SI joint structures when the prostheses are implanted in a dysfunctional SI joint, to a solid elastomer state upon application of radiation energy, wherein the fixation composition forms a positive fit connection by and between the prostheses and the dysfunctional SI joint structures.

7 Claims, 33 Drawing Sheets

Related U.S. Application Data application No. 13/857,977, filed on Apr. 5, 2013, now Pat. No. 11,273,042, which is a continuation of application No. 13/192,289, filed on Jul. 27, 2011, now abandoned.

(60) Provisional application No. 61/368,233, filed on Jul. 27, 2010.

(51) Int. Cl.

| | | |
|---|---|---|
| *A61B 5/06* | (2006.01) | |
| *A61B 6/00* | (2006.01) | |
| *A61B 6/03* | (2006.01) | |
| *A61B 8/08* | (2006.01) | |
| *A61B 17/16* | (2006.01) | |
| *A61B 17/70* | (2006.01) | |
| *A61B 17/88* | (2006.01) | |
| *A61B 34/20* | (2016.01) | |
| *A61F 2/30* | (2006.01) | |
| *A61F 2/46* | (2006.01) | |

(52) U.S. Cl.
CPC .......... *A61B 17/70* (2013.01); *A61B 17/7055* (2013.01); *A61B 17/7074* (2013.01); *A61B 17/8858* (2013.01); *A61B 34/20* (2016.02); *A61F 2/4455* (2013.01); *A61F 2/4601* (2013.01); *A61F 2/4611* (2013.01); *A61B 2576/00* (2013.01); *A61F 2002/30121* (2013.01); *A61F 2002/30123* (2013.01); *A61F 2002/30166* (2013.01); *A61F 2002/30593* (2013.01); *A61F 2002/30995* (2013.01)

(56) References Cited

U.S. PATENT DOCUMENTS

| | | | | |
|---|---|---|---|---|
| 4,570,623 A | * | 2/1986 | Ellison | A61B 17/68 606/75 |
| 4,714,469 A | * | 12/1987 | Kenna | A61F 2/4611 606/247 |
| 4,834,757 A | * | 5/1989 | Brantigan | A61F 2/42 623/17.11 |
| 4,946,378 A | * | 8/1990 | Hirayama | A61F 2/442 606/247 |
| 5,390,683 A | * | 2/1995 | Pisharodi | A61F 2/4455 606/279 |
| 5,397,364 A | * | 3/1995 | Kozak | A61B 17/025 606/247 |
| 5,425,772 A | * | 6/1995 | Brantigan | A61F 2/447 606/247 |
| 5,445,639 A | * | 8/1995 | Kuslich | A61B 17/1671 606/180 |
| 5,449,359 A | * | 9/1995 | Groiso | A61B 17/8872 411/460 |
| 5,454,814 A | * | 10/1995 | Comte | A61B 17/0642 606/75 |
| 5,458,638 A | * | 10/1995 | Kuslich | A61F 2/446 606/907 |
| 5,522,899 A | * | 6/1996 | Michelson | A61F 2/4455 606/279 |
| 5,593,409 A | * | 1/1997 | Michelson | A61F 2/4611 606/247 |
| 5,609,636 A | * | 3/1997 | Kohrs | A61F 2/4455 606/279 |
| 5,669,909 A | * | 9/1997 | Zdeblick | A61F 2/4455 606/247 |
| 5,683,394 A | * | 11/1997 | Rinner | A61F 2/4455 606/279 |
| 5,888,223 A | * | 3/1999 | Bray, Jr. | A61F 2/4611 606/247 |
| 5,904,719 A | * | 5/1999 | Errico | A61F 2/446 623/17.16 |
| 5,928,239 A | * | 7/1999 | Mirza | A61B 17/1668 606/167 |
| 5,968,098 A | * | 10/1999 | Winslow | A61F 2/446 606/248 |
| 6,045,579 A | * | 4/2000 | Hochshuler | A61F 2/4455 606/247 |
| 6,053,916 A | * | 4/2000 | Moore | A61F 2/30988 606/86 R |
| 6,096,080 A | * | 8/2000 | Nicholson | A61F 2/28 623/17.16 |
| 6,123,705 A | * | 9/2000 | Michelson | A61B 17/1671 623/17.16 |
| 6,165,219 A | * | 12/2000 | Kohrs | A61F 2/446 623/17.11 |
| 6,197,037 B1 | * | 3/2001 | Hair | A61B 17/688 606/151 |
| 6,224,631 B1 | * | 5/2001 | Kohrs | A61F 2/446 623/17.11 |
| 6,245,072 B1 | * | 6/2001 | Zdeblick | A61B 1/3135 623/17.11 |
| 6,371,987 B1 | * | 4/2002 | Weiland | A61F 2/4455 623/17.11 |
| 6,383,221 B1 | * | 5/2002 | Scarborough | A61F 2/30771 623/901 |
| 6,413,278 B1 | * | 7/2002 | Marchosky | A61B 17/1671 623/17.11 |
| 6,436,139 B1 | * | 8/2002 | Shapiro | A61F 2/446 623/17.11 |
| 6,440,170 B1 | * | 8/2002 | Jackson | A61F 2/4611 606/247 |
| 6,497,707 B1 | * | 12/2002 | Bowman | A61B 17/0401 606/218 |
| 6,641,613 B2 | * | 11/2003 | Sennett | A61B 17/1757 623/17.11 |
| 6,666,888 B1 | * | 12/2003 | Jackson | A61F 2/446 623/17.11 |
| 6,723,126 B1 | * | 4/2004 | Berry | A61F 2/4455 606/247 |
| 6,743,256 B2 | * | 6/2004 | Mason | A61F 2/447 623/17.11 |
| 6,743,257 B2 | * | 6/2004 | Castro | A61F 2/442 623/17.16 |
| 6,746,451 B2 | * | 6/2004 | Middleton | A61B 17/1664 606/180 |
| 6,761,738 B1 | * | 7/2004 | Boyd | A61F 2/4455 623/17.11 |
| 6,767,367 B1 | * | 7/2004 | Michelson | A61F 2/447 623/17.11 |
| 6,800,093 B2 | * | 10/2004 | Nicholson | A61B 17/1757 623/23.5 |
| 6,835,208 B2 | * | 12/2004 | Marchosky | A61F 2/4455 623/17.11 |
| D503,801 S | * | 4/2005 | Jackson | D24/155 |
| 6,942,698 B1 | * | 9/2005 | Jackson | A61F 2/4611 606/279 |
| 7,201,775 B2 | * | 4/2007 | Gorensek | A61F 2/446 623/17.11 |
| 7,235,101 B2 | * | 6/2007 | Berry | A61F 2/4455 623/17.14 |
| 7,326,251 B2 | * | 2/2008 | McCombe | A61F 2/447 623/17.16 |
| 7,648,509 B2 | * | 1/2010 | Stark | A61F 2/4601 606/90 |
| 7,708,761 B2 | * | 5/2010 | Petersen | A61L 27/3608 606/247 |
| 7,749,225 B2 | * | 7/2010 | Chappuis | A61B 17/1617 606/167 |
| 7,794,500 B2 | * | 9/2010 | Felix | A61F 2/447 623/17.11 |
| 7,837,732 B2 | * | 11/2010 | Zucherman | A61F 2/446 623/17.11 |
| 7,846,206 B2 | * | 12/2010 | Oglaza | A61B 17/8858 623/17.11 |
| 7,914,530 B2 | * | 3/2011 | Michelson | A61B 17/8888 623/17.11 |

(56) References Cited

U.S. PATENT DOCUMENTS

| | | | |
|---|---|---|---|
| 7,922,765 B2* | 4/2011 | Reiley | A61B 17/70 606/279 |
| 8,021,392 B2* | 9/2011 | Petersen | A61B 17/1757 606/247 |
| 8,062,294 B2* | 11/2011 | Reynolds | A61B 17/8052 606/301 |
| 8,066,773 B2* | 11/2011 | Muhanna | A61F 2/4425 623/17.14 |
| 8,080,046 B2* | 12/2011 | Suddaby | A61B 17/1637 623/17.11 |
| 8,088,163 B1* | 1/2012 | Kleiner | A61F 2/442 623/17.11 |
| 8,133,283 B2* | 3/2012 | Wilson | A61B 17/1782 606/86 R |
| 8,143,042 B2* | 3/2012 | Bettinger | C08G 63/6854 435/395 |
| 8,157,865 B2* | 4/2012 | Hochschuler | A61F 2/4455 606/279 |
| 8,221,428 B2* | 7/2012 | Trieu | A61B 17/7076 606/104 |
| 8,226,721 B2* | 7/2012 | Belliard | A61F 2/4425 623/17.15 |
| 8,287,572 B2* | 10/2012 | Bae | A61F 2/447 606/279 |
| 8,343,189 B2* | 1/2013 | Assell | A61F 2/4405 606/279 |
| 8,348,950 B2* | 1/2013 | Assell | A61B 17/32002 606/79 |
| 8,388,667 B2* | 3/2013 | Reiley | A61B 17/8695 606/301 |
| 8,414,648 B2* | 4/2013 | Reiley | A61B 17/1615 606/279 |
| 8,419,722 B2* | 4/2013 | Richards | A61B 17/00491 604/82 |
| 8,425,570 B2* | 4/2013 | Reiley | A61B 17/866 606/279 |
| 8,444,693 B2* | 5/2013 | Reiley | A61F 2/4455 623/17.11 |
| 8,470,004 B2* | 6/2013 | Reiley | A61B 17/1671 606/279 |
| 8,491,656 B2* | 7/2013 | Schoedinger, III | A61F 2/4611 623/17.16 |
| 8,523,945 B1* | 9/2013 | Wensel | A61B 17/70 623/17.11 |
| 8,551,171 B2* | 10/2013 | Johnson | A61B 17/844 606/279 |
| 8,551,175 B1* | 10/2013 | Wensel | A61F 2/447 623/17.11 |
| 8,617,244 B2* | 12/2013 | Reichen | A61F 2/4455 623/17.11 |
| 8,679,123 B2* | 3/2014 | Kinmon | A61B 17/0642 606/75 |
| 8,709,042 B2* | 4/2014 | Greenhalgh | A61F 2/4611 606/279 |
| 8,709,045 B1* | 4/2014 | Folsom | A61B 17/1615 606/247 |
| 8,721,722 B2* | 5/2014 | Shah | A61F 2/4611 623/17.11 |
| 8,740,912 B2* | 6/2014 | Stark | A61B 17/17 606/90 |
| 8,790,368 B2* | 7/2014 | Sullivan | A61F 2/0811 606/325 |
| 8,808,377 B2* | 8/2014 | Donner | A61F 2/4611 623/17.11 |
| 8,852,280 B2* | 10/2014 | Armstrong | A61F 2/4455 623/17.11 |
| D717,951 S* | 11/2014 | Cheney | D24/155 |
| 8,951,254 B2* | 2/2015 | Mayer | A61B 17/1617 623/18.11 |
| 8,961,571 B2* | 2/2015 | Lee | A61F 2/4601 606/279 |
| 9,005,291 B2* | 4/2015 | Loebl | A61F 2/4611 623/17.15 |
| 9,039,768 B2* | 5/2015 | Voellmicke | A61F 2/4611 606/86 A |
| 9,107,745 B2* | 8/2015 | Bouduban | A61F 2/0811 |
| 9,125,649 B2* | 9/2015 | Bruewer | A61B 17/07207 |
| 9,186,155 B2* | 11/2015 | Katzman | A61B 17/1671 |
| 9,204,973 B2* | 12/2015 | Aflatoon | A61F 2/447 |
| 9,254,130 B2* | 2/2016 | Hollis | A61B 17/68 |
| 9,333,090 B2* | 5/2016 | Donner | A61B 17/7055 |
| 9,359,472 B2* | 6/2016 | Nicholson | A61K 45/06 |
| 9,408,711 B2* | 8/2016 | Burkinshaw | A61F 2/4465 |
| 9,480,511 B2* | 11/2016 | Butters | A61F 2/4202 |
| 9,566,103 B2* | 2/2017 | Mayer | A61B 17/17 |
| 9,585,756 B2* | 3/2017 | Mayer | A61B 17/70 |
| 9,592,131 B2* | 3/2017 | Sandstrom | A61F 2/30767 |
| 9,610,172 B2* | 4/2017 | Butler | A61F 2/4465 |
| 9,615,856 B2* | 4/2017 | Arnett | A61B 17/0642 |
| 9,724,447 B2* | 8/2017 | Karp | A61L 15/26 |
| 9,826,986 B2* | 11/2017 | Donner | A61B 17/7055 |
| 9,888,911 B2* | 2/2018 | Siegal | A61B 17/025 |
| 10,166,022 B2* | 1/2019 | Early | A61B 17/0642 |
| 10,182,921 B2* | 1/2019 | Georges | A61F 2/4455 |
| 10,201,427 B2* | 2/2019 | Mauldin | A61F 2/4455 |
| 10,238,382 B2* | 3/2019 | Terrill | A61B 17/0642 |
| 10,278,742 B2* | 5/2019 | Pavlov | A61F 2/447 |
| 10,285,689 B2* | 5/2019 | Finley | A61B 17/15 |
| 10,292,825 B2* | 5/2019 | Kahmer | A61F 2/447 |
| 10,376,367 B2* | 8/2019 | Fallin | A61B 17/8004 |
| 10,376,379 B2* | 8/2019 | Songer | A61F 2/4455 |
| 10,383,733 B2* | 8/2019 | Early | A61B 17/7059 |
| 10,492,841 B2* | 12/2019 | Hartdegen | A61B 17/8085 |
| 10,512,548 B2* | 12/2019 | Messerli | A61F 2/447 |
| 10,603,055 B2* | 3/2020 | Donner | A61B 17/1739 |
| D892,331 S* | 8/2020 | Hollis | D24/155 |
| 10,729,555 B1* | 8/2020 | Rappaport | A61F 2/4465 |
| 10,779,816 B2* | 9/2020 | Goldstein | A61B 17/0642 |
| 10,918,729 B2* | 2/2021 | Harris | A61L 27/48 |
| 11,006,949 B2* | 5/2021 | Daniel | A61B 17/8872 |
| 11,103,239 B2* | 8/2021 | Isch | A61B 17/0642 |
| 11,752,011 B2* | 9/2023 | Stuart | A61B 17/92 623/17.11 |
| 11,866,523 B2* | 1/2024 | Gabriele | C08F 2/10 |
| 2001/0020186 A1* | 9/2001 | Boyce | A61F 2/4455 606/279 |
| 2002/0038123 A1* | 3/2002 | Visotsky | A61B 17/8095 606/907 |
| 2004/0193271 A1* | 9/2004 | Fraser | A61F 2/442 623/17.11 |
| 2004/0260286 A1* | 12/2004 | Ferree | A61F 2/4455 606/247 |
| 2005/0149192 A1* | 7/2005 | Zucherman | A61B 17/1671 623/17.11 |
| 2005/0222683 A1* | 10/2005 | Berry | A61F 2/442 623/17.13 |
| 2006/0054171 A1* | 3/2006 | Dall | A61B 90/11 128/898 |
| 2006/0058802 A1* | 3/2006 | Kofoed | A61B 17/562 606/75 |
| 2006/0178745 A1* | 8/2006 | Bartish, Jr. | A61F 2/442 623/17.13 |
| 2007/0156241 A1* | 7/2007 | Reiley | A61B 17/56 623/17.11 |
| 2007/0239278 A1* | 10/2007 | Heinz | A61F 2/4425 623/17.15 |
| 2007/0270879 A1* | 11/2007 | Isaza | A61B 17/1739 606/104 |
| 2008/0140082 A1* | 6/2008 | Erdem | A61B 17/8805 606/92 |
| 2008/0221623 A1* | 9/2008 | Gooch | A61B 17/686 606/302 |
| 2009/0024174 A1* | 1/2009 | Stark | A61B 17/7055 606/321 |
| 2009/0036927 A1* | 2/2009 | Vestgaarden | A61B 17/7064 606/247 |
| 2009/0099602 A1* | 4/2009 | Aflatoon | A61F 2/4405 606/301 |

(56) References Cited

U.S. PATENT DOCUMENTS

| | | | |
|---|---|---|---|
| 2009/0138015 A1* | 5/2009 | Conner | A61F 2/4684 606/90 |
| 2009/0149884 A1* | 6/2009 | Snyder | A61F 2/0805 606/228 |
| 2009/0254090 A1* | 10/2009 | Lizee | A61B 17/0642 606/75 |
| 2009/0259261 A1* | 10/2009 | Reiley | A61B 17/7055 606/329 |
| 2010/0158978 A1* | 6/2010 | Markland | A61K 9/12 424/490 |
| 2010/0268228 A1* | 10/2010 | Petersen | A61B 17/1671 606/60 |
| 2011/0040362 A1* | 2/2011 | Godara | A61B 18/1482 607/116 |
| 2011/0046737 A1* | 2/2011 | Teisen | A61B 17/1671 606/86 A |
| 2011/0098709 A1* | 4/2011 | Malandain | A61B 17/1617 606/79 |
| 2011/0098816 A1* | 4/2011 | Jacob | A61B 17/7055 623/17.11 |
| 2011/0098817 A1* | 4/2011 | Eckhardt | A61B 17/7055 623/17.11 |
| 2011/0160866 A1* | 6/2011 | Laurence | A61F 2/4611 623/17.16 |
| 2011/0184518 A1* | 7/2011 | Trieu | A61B 17/562 623/17.11 |
| 2011/0184520 A1* | 7/2011 | Trieu | A61B 17/562 623/17.11 |
| 2011/0230966 A1* | 9/2011 | Trieu | A61B 17/562 623/17.11 |
| 2011/0238181 A1* | 9/2011 | Trieu | A61B 17/7055 623/17.11 |
| 2011/0295272 A1* | 12/2011 | Assell | A61B 17/32002 606/131 |
| 2011/0301407 A1* | 12/2011 | Deitch | A61F 2/0045 600/30 |
| 2012/0083883 A1* | 4/2012 | Ginn | A61B 17/1604 623/17.11 |
| 2012/0116454 A1* | 5/2012 | Edidin | A61B 17/1757 606/279 |
| 2012/0130374 A1* | 5/2012 | Bouduban | A61F 2/0805 606/75 |
| 2012/0191191 A1* | 7/2012 | Trieu | A61B 17/864 623/17.11 |
| 2012/0215315 A1* | 8/2012 | Hochschuler | A61F 2/4455 623/17.16 |
| 2012/0253406 A1* | 10/2012 | Bae | A61F 2/4611 606/279 |
| 2012/0296428 A1* | 11/2012 | Donner | A61B 17/7043 623/17.11 |
| 2012/0323285 A1* | 12/2012 | Assell | A61B 17/8625 606/305 |
| 2012/0330420 A1* | 12/2012 | Brodke | A61L 27/32 623/17.16 |
| 2013/0030456 A1* | 1/2013 | Assell | A61B 17/32002 606/170 |
| 2013/0053852 A1* | 2/2013 | Greenhalgh | A61B 17/1659 606/83 |
| 2013/0053902 A1* | 2/2013 | Trudeau | A61B 17/8685 606/313 |
| 2013/0085535 A1* | 4/2013 | Greenhalgh | A61B 17/7055 606/301 |
| 2013/0172736 A1* | 7/2013 | Abdou | G16H 50/30 606/279 |
| 2013/0173004 A1* | 7/2013 | Greenhalgh | A61F 2/4455 623/17.16 |
| 2013/0237988 A1* | 9/2013 | Mauldin | A61B 17/1604 606/84 |
| 2013/0245764 A1* | 9/2013 | Mauldin | A61F 2/44 623/17.11 |
| 2013/0267836 A1* | 10/2013 | Mauldin | A61B 17/1671 606/96 |
| 2013/0267961 A1* | 10/2013 | Mauldin | A61B 17/68 606/99 |
| 2013/0267989 A1* | 10/2013 | Mauldin | A61M 29/00 606/86 R |
| 2013/0296953 A1* | 11/2013 | Mauldin | A61B 17/7055 606/328 |
| 2014/0066991 A1* | 3/2014 | Marik | A61B 17/8625 606/279 |
| 2014/0088707 A1* | 3/2014 | Donner | A61F 2/30988 623/17.11 |
| 2014/0135850 A1* | 5/2014 | Parent | A61B 17/8872 606/304 |
| 2014/0142700 A1* | 5/2014 | Donner | A61B 17/1739 623/17.11 |
| 2014/0200618 A1* | 7/2014 | Donner | A61F 2/4611 606/281 |
| 2014/0207240 A1* | 7/2014 | Stoffman | A61B 17/68 623/18.11 |
| 2014/0277463 A1* | 9/2014 | Yerby | A61F 2/4611 623/17.11 |
| 2015/0173805 A1* | 6/2015 | Donner | A61B 17/17 606/279 |
| 2016/0081810 A1* | 3/2016 | Reiley | A61B 17/1757 623/17.11 |
| 2016/0100870 A1* | 4/2016 | Lavigne | A61B 17/864 606/304 |
| 2017/0156879 A1* | 6/2017 | Janowski | A61F 2/4611 |
| 2019/0071537 A1* | 3/2019 | Pereira | C08G 63/918 |
| 2021/0169660 A1* | 6/2021 | Reckling | A61B 17/7055 |
| 2021/0393408 A1* | 12/2021 | Ginn | A61F 2/4611 |
| 2021/0393409 A1* | 12/2021 | Ginn | A61B 17/1757 |
| 2022/0071644 A1* | 3/2022 | Donner | A61B 17/144 |
| 2022/0273447 A1* | 9/2022 | Ginn | A61B 17/848 |
| 2022/0273448 A1* | 9/2022 | Ginn | A61F 2/4611 |
| 2022/0296378 A1* | 9/2022 | Ginn | A61F 2/4601 |
| 2022/0304814 A1* | 9/2022 | Ginn | A61B 6/485 |
| 2022/0346964 A1* | 11/2022 | Spenciner | A61F 2/40 |
| 2023/0000631 A1* | 1/2023 | Ginn | A61B 17/1664 |
| 2023/0032203 A1* | 2/2023 | Maxwell | A61B 17/869 |
| 2023/0255623 A1* | 8/2023 | Ritz | A61B 17/0642 606/75 |

* cited by examiner

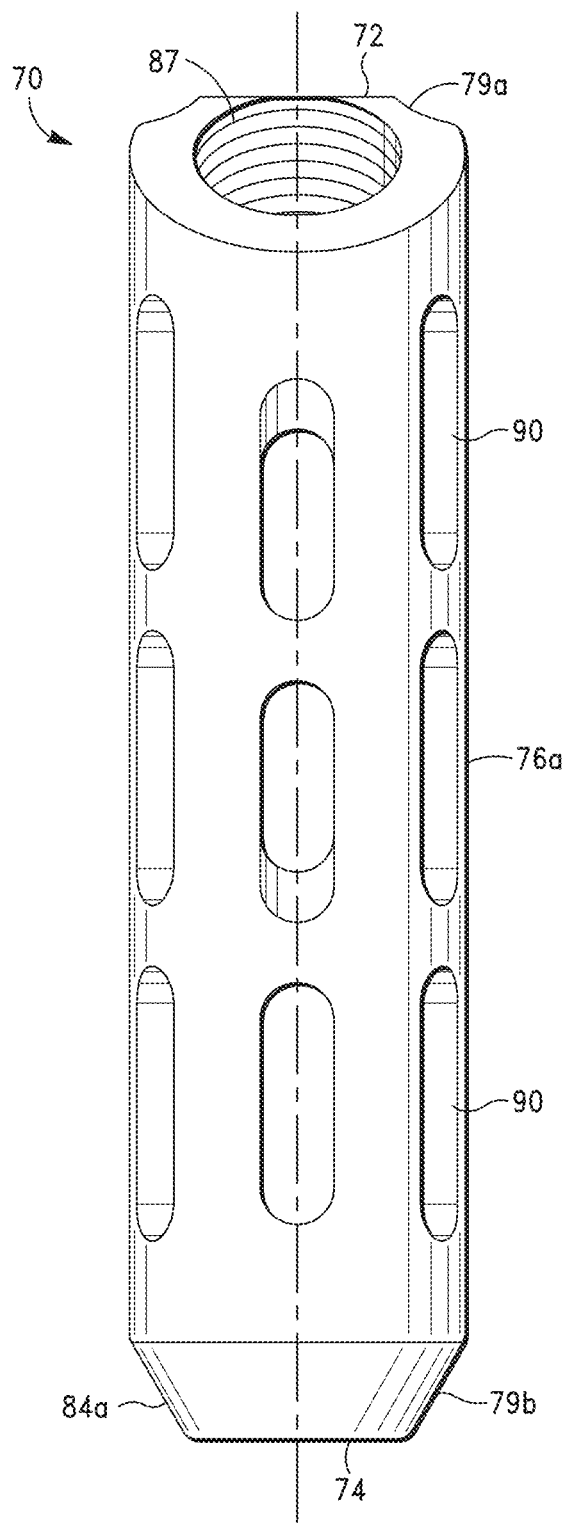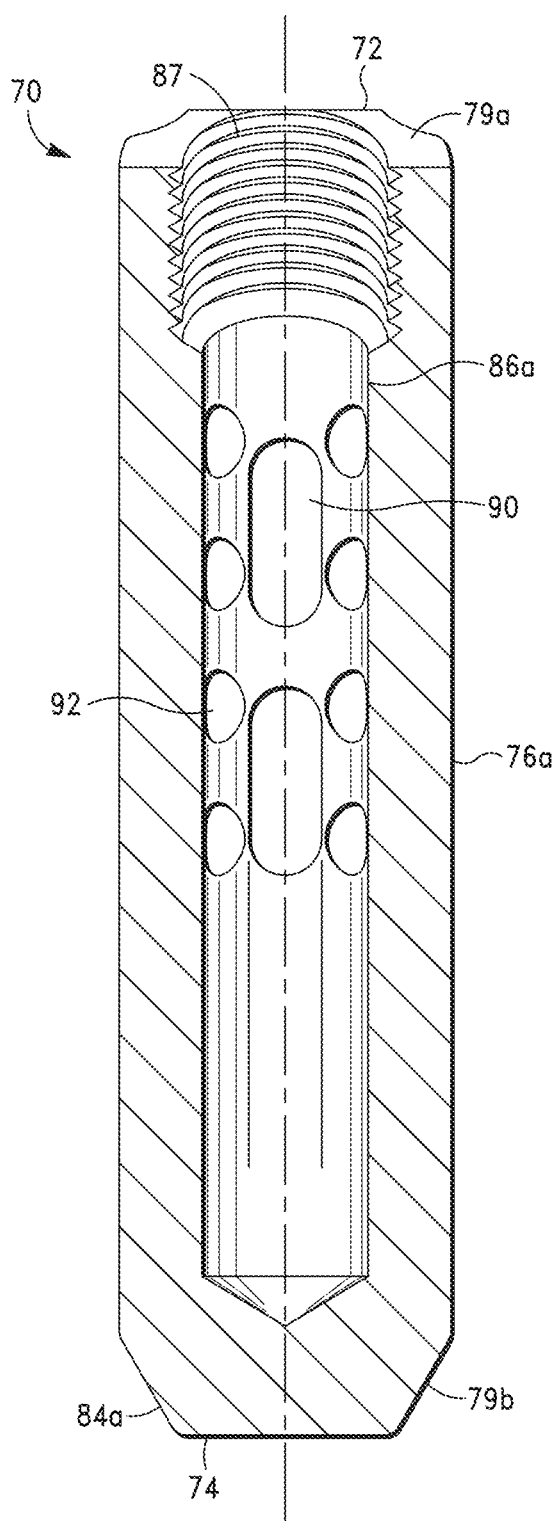
FIG. 6G
FIG. 6H

SACROILIAC JOINT STABILIZATION PROSTHESES

CROSS-REFERENCES TO RELATED APPLICATIONS

This application is a continuation of U.S. patent application Ser. No. 17/463,831, filed Sep. 1, 2021, which is a continuation-in-part application of U.S. patent application Ser. No. 13/857,977, filed Apr. 5, 2013, which is a continuation application of U.S. patent application Ser. No. 13/192,289, filed Jul. 27, 2011, now abandoned, which claims the benefit of U.S. provisional patent application Ser. No. 61/368,233, filed Jul. 27, 2010.

FIELD OF THE INVENTION

The present invention relates to methods, systems and apparatus for stabilizing junctions between bone structures. More particularly, the present invention relates to methods, systems and apparatus for stabilizing dysfunctional sacroiliac (SI) joints.

BACKGROUND OF THE INVENTION

As is well known in the art, the sacroiliac (SI) joint 6 comprises a diarthrodial synovial joint, which, as illustrated in FIG. 1A, is defined by the interface between the articular surfaces of the sacrum 2 and the ilium 4. Thus, the SI joint 6 is defined by (and, hence, comprises) portions of the sacrum 2 and ilium 4.

As is also well known in the art, the SI joint further comprises articular cartilage, i.e., hyaline and fibrocartilage, and a strong, extensive ligamentous architecture, which stabilizes the SI joint.

Generally, the articular surfaces of the sacrum 2 and the ilium 4 that define the SI joint 6 comprise cortical bone 8, which is more compact, dense and hard relative to softer trabecular bone 10, which, as further illustrated in FIG. 1A, is disposed in the interior regions of the sacrum and ilium 2, 4.

The SI Joint is distinguished from other synovial joints by the atypical articulation of the different articular surfaces of the sacrum and ilium; the articular surface of the sacrum comprising hyaline cartilage and the articular surface of the ilium comprising substantially stronger fibrocartilage.

As is further well known in the art, the primary plane of motion of the SI joint is anterior-posterior along a transverse axis. The terms often employed to describe the relative motion of the sacrum and ilium are nutation, which refers to anterior-inferior movement of the sacrum while the coccyx (denoted "3" in FIG. 1A) moves posteriorly relative to the ilium, and counternutation, which refers to posterior-superior movement of the sacrum while the coccyx moves anteriorly relative to the ilium.

In most healthy individuals, the SI joint range of motion in flexion-extension is approximately 3°, approximately 1.5° in axial rotation and approximately 0.8° in lateral bending.

As is well established, the SI joint performs several seminal biomechanical functions. The primary functions of the SI joint are to attenuate loads exerted on the upper body and to distribute the loads to the lower extremities. The SI joint also functions as a shock absorber for loads exerted on spine.

As Is also well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

Indeed, SI joint dysfunction is estimated to be the primary cause of lower back pain in 15-30% of subjects afflicted with such pain. However, lower back pain associated with SI joint dysfunction is suspected to be far more common than most healthcare providers realize, since such pain is often associated with other skeletal and musculoskeletal dysfunctions.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans ilii, and other degenerative conditions of the SI joint structures.

Various ram-surgical methods, such as administration of pharmacological agents, e.g., the corticosteroid prednisone, and surgical methods and devices, i.e., prostheses, have been developed and employed to treat SI joint dysfunction.

The most common approach employed to treat SI joint dysfunctions (when non-surgical treatments fail to ameliorate pain associated therewith), at present, is SI joint stabilization, i.e., reinforcing or modulating articulation by and between the sacrum and ilium, via surgical intervention.

SI joint stabilization typically comprises surgical placement of a prosthesis proximate to or in a dysfunctional SI joint and is generally characterized by the direction of access to the dysfunctional SI joint, i.e., anterior, posterior or lateral.

Although several conventional SI joint stabilization surgical methods and associated bone prostheses have effectively ameliorated pain associated with SI joint dysfunction, there remains many disadvantages associated with the conventional methods and associated prostheses.

A major disadvantage associated with many conventional SI joint stabilization surgical methods is that the surgeon is required to make a substantial incision in and through the skin and tissues of a subject to access the dysfunctional SI joint. Often referred to as "open surgery" methods, these surgical methods have the attendant disadvantages of requiring general anesthesia and often involve increased operative time, pain, hospitalization, and recovery time due to the extensive soft tissue damage. There is also an increased probability of post-surgical complication associated with open surgery methods, such as nosocomial infection.

Minimally-invasive methods for SI joint stabilization have thus been developed to address the noted disadvantages associated with open surgery methods. Although conventional minimally-invasive SI joint stabilization methods, such as the methods disclosed in U.S. Pub. No. 2009/0076551 to Petersen, have garnered some success in relieving pain associated with SI joint dysfunction and have effectively addressed many of the disadvantages associated with open surgery methods, there similarly remains many disadvantages associated with conventional minimally-invasive SI joint stabilization methods.

A major disadvantage associated with many conventional minimally-invasive SI joint stabilization methods is that such methods are difficult to perform and, hence, often require extensive, system-specific surgical training and experience. Despite the level of surgical training and experience that surgeons possess, when such conventional minimally-invasive SI joint stabilization methods are employed, there is still a substantial incidence of damage to the lumbosacral neurovascular structures proximate to the SI joint.

A further disadvantage associated with many conventional minimally-invasive SI joint stabilization methods and associated apparatus, i.e., prostheses, such as the methods and prostheses disclosed in U.S. Pub. No. 2009/0076551 to Petersen, is that pre-existing sacral abnormalities can lead to displacement of the implanted prostheses, which can, and often will result in damage to surrounding bone and soft tissue structures.

An additional disadvantage associated with many conventional minimally invasive SI joint stabilization methods is that they comprise anterior or lateral approaches to the dysfunctional SI joint and, hence, muscles, e.g., gluteal aponeurotic fascia and gluteus medius, and ligaments are typically disrupted, and nerves and blood vessels are susceptible to damage during placement of a prosthesis in a dysfunctional SI joint.

Further, some conventional minimally-invasive SI joint stabilization methods are particularly prone to failure due to displacement of the prostheses in the dysfunctional SI joint and/or failure of the prostheses to effectively engage the SI joint structures, e.g., articular surfaces of the sacrum and/or ilium.

Various "improved" prostheses have thus been developed for use in minimally-invasive SI joint stabilization methods or procedures to effectively engage SI joint structures and maintain engagement thereto during SI joint function.

Although many of the "improved" prostheses, when deployed properly in a dysfunctional SI joint can, and often will, effectively engage SI joint structures, there remains several disadvantages associated with the prostheses. Illustrative are the prostheses disclosed in U.S. Pat. No. 8,951,254 to Mayer, et al.

The prostheses disclosed in U.S. Pat. No. 8,951,254 comprise or are coated with a liquefiable synthetic polymer that is adapted to liquefy upon administration of mechanical energy, e.g., high frequency vibration, when implanted and re-solidify thereafter to securely engage the SI joint structures, i.e., sacrum and ilium.

A major disadvantage associated with the prostheses disclosed in U.S. Pat. No. 8,951,254 is that the liquefiable synthetic polymers, when re-solidified in situ, are structurally inferior to the osseous or bone tissue of the sacrum and ilium. The fusion sites between the articular surfaces of the sacrum and ilium that define the SI joint are, thus, highly susceptible to structural fatigue and failure, which can, and often will, result in misalignment of the SI joint and ultimately increased pain for the subject.

A further disadvantage associated with the prostheses disclosed in U.S. Pat. No. 8,951,254 is that the synthetic liquefiable synthetic polymers are also substantially immunogenic and will induce an adverse immune response when the prostheses are implanted in a dysfunctional SI joint. As is well established, the adverse immune response can, and often will, prevent healing and osteogenic processes, e.g., remodeling of damaged osseous tissue and regeneration of new osseous tissue.

Additional disadvantages associated with the prostheses disclosed in U.S. Pat. No. 8,951,254 and many other prostheses designed for minimally-invasive SI joint stabilization are that the noted prostheses are difficult to accurately place in optimum positions in a dysfunctional SI joint and, in many instances, lack sufficient structural properties, such as rigidity and/or fatigue resistance, to effectively stabilize the dysfunctional SI joint.

It would thus be desirable to provide SI joint stabilization systems and apparatus, which substantially reduce or eliminate the disadvantages associated with conventional SI joint stabilization systems and apparatus.

It is therefore an object of the invention to provide improved SI joint stabilization systems and apparatus, which substantially reduce or eliminate the disadvantages associated with conventional SI joint stabilization systems and apparatus.

It is another object of the invention to provide improved minimally-invasive SI joint stabilization systems and apparatus, which can be readily employed to place prostheses in and, thereby, stabilize dysfunctional SI joints via a posterior approach.

It is another object of the invention to provide improved minimally-invasive SI joint stabilization systems and apparatus, which can be readily employed to stabilize dysfunctional SI joints.

It is another object of the invention to provide improved minimally-invasive SI joint stabilization systems and apparatus, which, when implanted in a dysfunctional SI joint, effectively ameliorate pain associated with the SI joint dysfunction.

It is another object of the invention to provide improved SI joint prostheses that can readily be employed in minimally-invasive SI joint stabilization methods and provide secure engagement to SI joint structures.

It is another object of the invention to provide improved SI joint prostheses that can readily be employed in minimally-invasive SI joint stabilization methods and possess optimal structural properties to effectively stabilize dysfunctional SI joints.

It is yet another object of the invention to provide improved SI joint prostheses that can readily be employed in minimally-invasive SI joint stabilization methods and facilitate remodeling of damaged osseous tissue and regeneration of new osseous tissue and osseous tissue structures.

SUMMARY OF THE INVENTION

The present invention is directed to minimally-invasive methods, systems and apparatus for stabilizing dysfunctional SI joints.

In some embodiments of the invention, there are thus provided minimally-invasive systems and associated prostheses for stabilizing dysfunctional SI joints. In one embodiment, there is thus a SI joint stabilization prosthesis for stabilizing a dysfunctional SI joint comprising:

an elongated prosthesis structure adapted to be implanted in the dysfunctional SI joint via a posterior approach, the dysfunctional SI joint being disposed between and defined by a sacrum bone structure and an ilium bone structure, the elongated prosthesis structure comprising first and second elongated partially cylindrical sections connected to a bridge section, whereby the elongated prosthesis structure comprises a continuous exterior surface comprising first and second partially cylindrical surface regions, the elongated prosthesis structure comprising proximal and distal ends, the bridge section comprising proximal and distal ends, the bridge section distal end comprising a first tapered region configured and adapted to disrupt at least articular cartilage and cortical bone, the first elongated partially cylindrical section comprising a first elongated partially cylindrical section internal lumen, the second elongated partially cylindrical section comprising a second elongated partially cylindrical section comprising a second elongated partially cylindrical section internal lumen, the first and second elongated partially cylindrical sections further comprising a plurality of slots extending from the first and second elongated partially cylindrical section lumens to and through the exterior surface of the elongated prosthesis structure, the elongated prosthesis structure further comprising a poly(glycerol-co-sebacate) acrylate (PGSA) based fixation composition disposed in one or both of the internal prosthesis engagement member lumens of the prosthesis in a flowable state, the fixation composition being adapted to transition from the flowable state, wherein the fixation composition is capable of flowing through and dispersed out of the plurality of slots and into a SI joint space between the elongated prosthesis structure and the sacrum bone structure or ilium bone structure when the elongated prosthesis structure is implanted in the dysfunctional SI joint, to a solid elastomer state upon application of radiation energy, wherein the fixation composition forms a positive fit connection by and between the elongated prosthesis structure and the sacrum and ilium bone structures when the elongated prosthesis structure is the implanted in the dysfunctional SI joint.

In some embodiments, the fixation composition further comprises a photoinitiator comprising 2-hydroxy-1-[4-hydroxyethoxy) phenyl]-2-methyl-1-propanone, 2,2-dimethoxy-2-phenylacetophenone, titanocenes, fluorinated diaryltitanocenes, iron arene complexes, manganese decacarbonyl or methylcyclopentadienyl manganese tricarbonyl.

In some embodiments, the radiation energy comprises ultraviolet (UV) light radiation in the range of 10-400 nm.

In some embodiments, the fixation composition further comprises a bone morphogenic protein (BMP) comprising BMP-1, BMP2a, BMP2b, BMP3, BMP4, BMP5, BMP6, BMP7 or BMP8a.

In some embodiments, the fixation composition further comprises an antibiotic and/or an anti-inflammatory.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 6G is a right-side plan view of the prosthesis shown in FIG. 6A, in accordance with the invention;

FIG. 6H is a right-side sectional plan view of the prosthesis shown in FIG. 6A, in accordance with the invention;

DETAILED DESCRIPTION OF THE PREFERRED EMBODIMENT

Figure 1A:
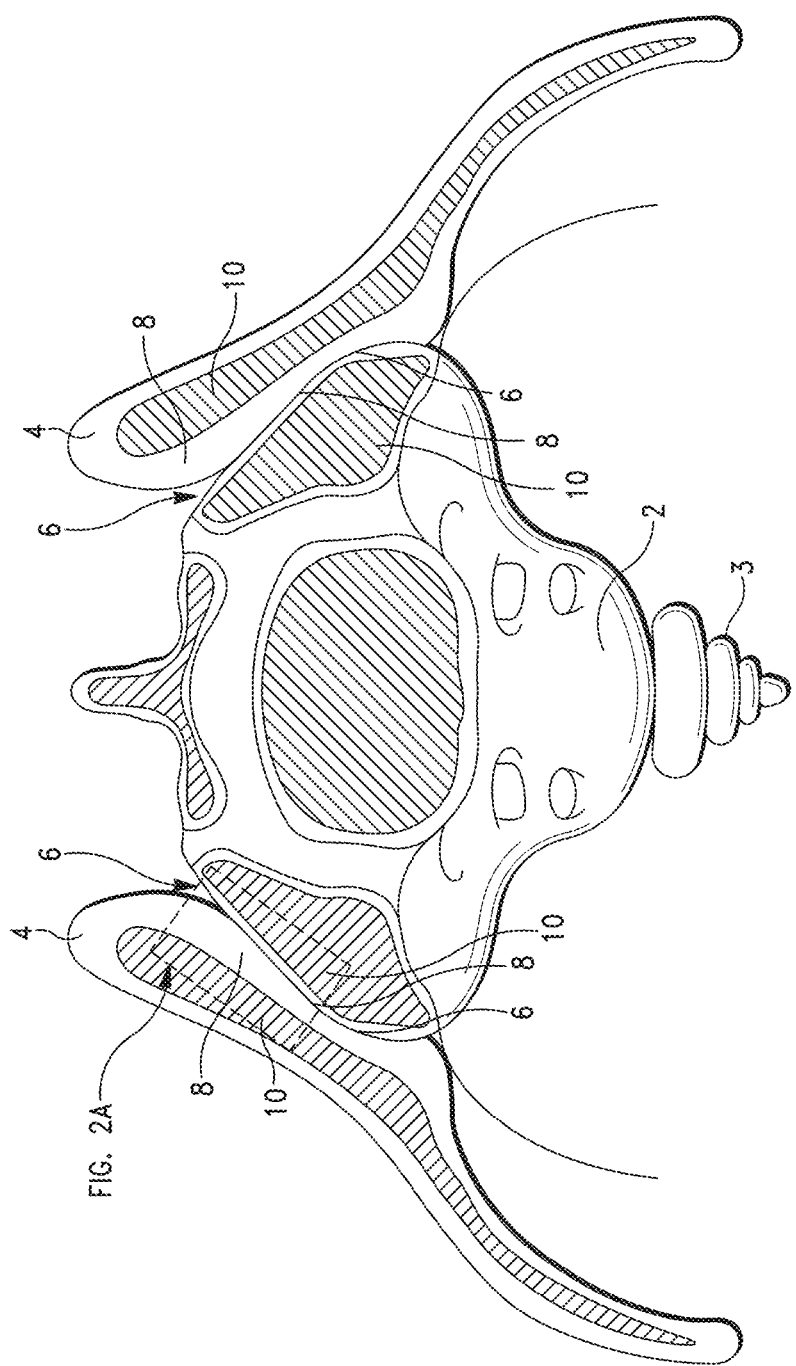
FIG. 1A is a schematic illustration of a human pelvic region from an anteroposterior (AP) perspective showing the SI joints thereof.
Figure 1B:
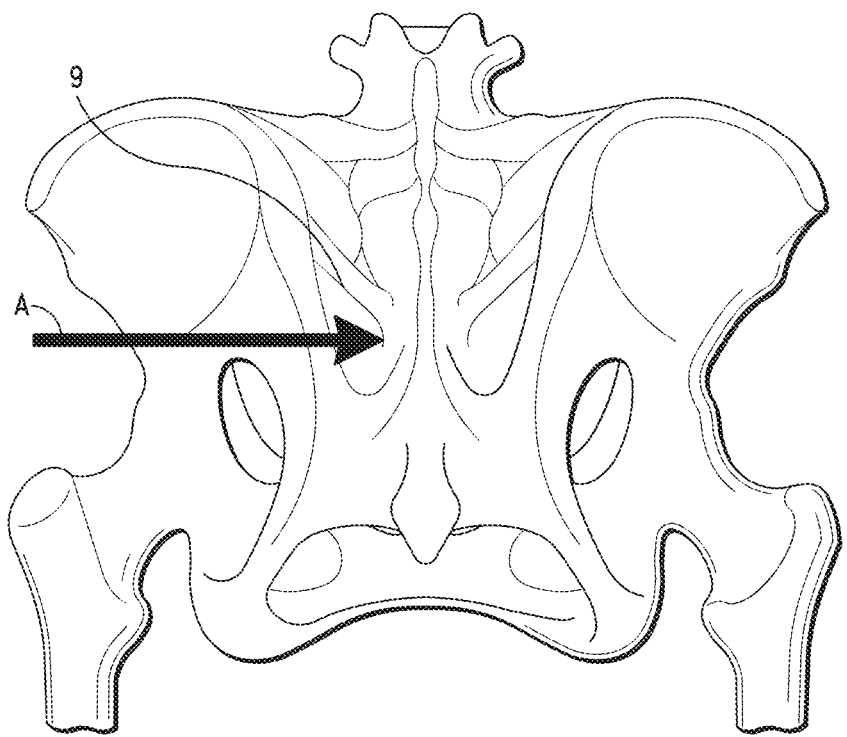
FIG. 1B is another schematic illustration of a human pelvic region from a posterior perspective showing the adjoining sacrum and ilium bone structures, and ligamentous structures thereof.
Figure 1C:
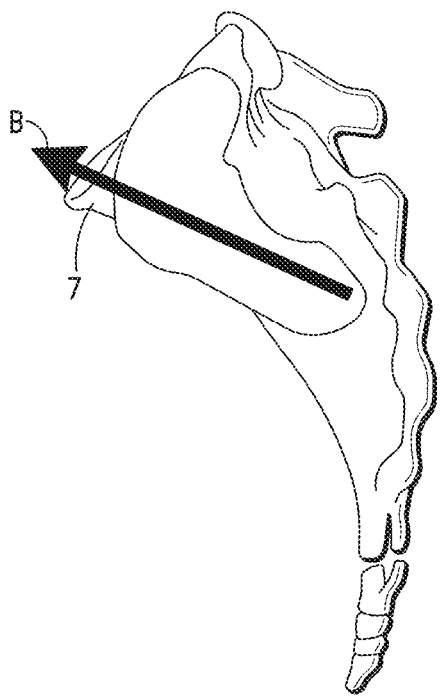
FIG. 1C is a schematic illustration of the sacrum and coccyx from a lateral perspective showing the sacral promontory and the articular surface of sacrum.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that, although the present invention is described and illustrated in connection with sacroiliac (SI) joint stabilization, fixation and fusion procedures, the invention is not limited to such procedures. According to the invention, the apparatus, systems and methods of the invention can also be employed to stabilize and/or fuse other articulating bone structures, including, without limitation, spinal vertebrae, tarsal bones and the like.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures.

The term "dysfunctional" as used in connection with a SI joint, means and includes a physiological abnormality, disorder or impairment of an SI joint, including, but limited to, traumatic fracture dislocation of the pelvis, degenerative arthritis, sacroiliitis, i.e., an inflammation or degenerative condition of the SI joint; osteitis condensans ilii, and other degenerative conditions of SI joint bone structures.

The terms "articular surface" and "articulating surface" are used interchangeably herein in connection with bone structures; particularly, the sacrum and ilium bone structures, and mean and include a surface of a bone structure that forms an articulating junction (i.e., a synovial joint) with an adjacent bone structure, e.g., the articular surfaces of the sacrum and ilium bone structures.

The terms "fusion" and "arthrodesis" are used interchangeably herein in connection with bone structures, and mean and include partial or complete immobilization of adjacent bone structures; particularly, the sacrum and ilium bone structures.

The term "stabilization", as used herein, means and includes reinforcing, e.g., supporting, or modulating motion of adjacent articular bone structures; particularly, the sacrum and ilium bone structures. The term "stabilization", thus, in some instances, means and includes fusion and arthrodesis of adjacent bone structures.

The term "prosthesis", as used herein in connection with bone structures, means and includes a system or apparatus configured and adapted to stabilize or modulate motion of articulating bone structures; particularly, the sacrum and ilium bone structures.

The term "biodegradable", as used herein, means the ability of a material; particularly, a polymer or adhesive, to breakdown and be absorbed within the physiological environment of a SI joint and/or a structure associated therewith, including sacrum and ilium bone structures, by one or more physical, chemical, or cellular processes.

Biodegradable polymers, according to the invention, thus include, without limitation, polylactide polymers (PLA), copolymers of lactic and glycolic acids, including poly(lactic-co-glycolic) acid (PLGA) and poly(s-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly(polyol sebacate) (PPS), poly(xylitol sebacate) (PXS), poly(xylitol glutamate sebacate) (PXGS), hydroxybutyrate-hydroxyvalerate copolymers, polyesters such as, but not limited to, aspartic acid and different aliphatic diols; poly(alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and OctylSeal); polyethylene glycol) (PEG) based compositions, including FocalSeal®, Progel™, Duraseal™, DuraSeal™ Xact, Coseal® and ReSure Sealant; polysaccharide-based compositions, polypeptide-based compositions, and combinations thereof.

The term "osteogenic composition"; as used herein, means and includes an agent or composition that induces or modulates an osteogenic physiological or biological process, or cellular activity, e.g., induces proliferation, and/or growth and/or remodeling and/or regeneration of bone or osseous tissue.

The term "osteogenic composition" thus means and includes, without limitation, the following osteogenic materials and compositions comprising same: demineralized bone matrix, autograft bone material, allograft bone material, xenograft bone material, polymethyl-methacrylate, calcium-based bone void filler material, including hydroxyapatite (HA) and tricalcium phosphate; and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly(ethylene glycol) (PGS-PEG); and/or composites thereof, e.g., PGS-hydroxyapatite (HA) composites and PGS-poly(ε-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of osseous tissue, cartilage and connective tissue, e.g., tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)) and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF-2; basic fibroblast growth factor (bFGF) (also referred to as FGF2), transforming growth factor-β (TGF-β), including, TGF-β1 and TGF-β2; a growth hormone (GH), parathyroid hormone (PTH, including PTH1-34), transforming growth factor-α (TGF-α), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2) and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs) and embryonic stem cells.

The terms "biologically active agent" and "biologically active composition" also mean and include an "extracellular vesicle (EV)", "exosome" "microsome" or "micro-vesicle", which are used interchangeably herein, and mean and include a biological structure formed from a hydrocarbon monolayer or bilayer configured to contain or encase a composition of matter.

The terms "extracellular vesicle (EV)", "exosome", "microsome" and "micro-vesicle" thus include, without limitation, a biological structure formed from a lipid layer configured to contain or encase biologically active agents and/or combinations thereof.

The terms "extracellular vesicle (EV)", "exosome", "microsome" and "micro-vesicle" also include, without limitation, EVs derived from the aforementioned cells and compositions comprising same, e.g., BMSC-derived EVs.

The terms "pharmacological agent" and "active agent" are used interchangeably herein, and mean and include an agent, drug, compound, composition or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-α) inhibitors, including etanercept and infliximab, disease-modifying anti-rheumatic drugs (DMARDs), including methotrexate and hydroxychloroquine, antibiotics, anti-viral agents, steroidal anti-inflammatories, non-steroidal anti-inflammatories, anti-thrombotic agents, including anti-coagulants and anti-platelet agents, and vasodilating agents.

The terms "pharmacological agent" and "active agent" further mean and include, without limitation, the following bisphosphonate agents and compositions comprising same: risedronate (Actonel®), alendronate (Fosamax®), ibandronate (Boniva®), zoledronic acid (Reclast®), pamidronate (Aredia®) and etidronate (Didronel®).

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin and rifampin.

The terms "anti-inflammatory" and "anti-inflammatory agent" are also used interchangeably herein, and mean and include a "pharmacological agent", which, when a therapeutically effective amount is administered to a subject, prevents or treats bodily tissue inflammation, i.e., the protective tissue response to injury or destruction of tissues, which serves to destroy, dilute, or wall off both the injurious agent and the injured tissues.

Anti-inflammatory agents thus include, without limitation, dexamethasone, betamethasone, prednisone, prednisolone, methylprednisolone sodium succinate, methylprednisolone, cortisone, ketorolac, diclofenac and ibuprofen.

The terms "pharmacological agent" and "active agent" further mean and include, without limitation, the following metal-based antimicrobials and compositions comprising same: silver particles, copper particles, cobalt particles, nickel particles, zinc particles, zirconium particles, molybdenum particles, lead particles and mixtures thereof.

As indicated above, the term "pharmacological composition", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to minimally-invasive methods, systems and apparatus for stabilizing dysfunctional SI joints.

In some embodiments of the invention, there are thus provided minimally-invasive systems for stabilizing dysfunctional SI joints. As indicated above, in a preferred embodiment, the minimally-invasive systems (also referred to herein as "minimally-invasive SI joint stabilization systems") can be readily employed in minimally-invasive methods or procedures to stabilize dysfunctional SI joints via a posterior approach.

As indicated above, SI joint stabilization, including minimally-invasive SI joint stabilization, typically comprises surgical placement of a prosthesis proximate to or in a dysfunctional SI joint via anterior, lateral and posterior approaches to the SI joint.

From the perspective of FIG. 1A, an anterior approach to the SI joint 6 (and, hence, a dysfunctional SI joint) would be substantially perpendicular to the page upon which FIG. 1A is printed.

Figure 2A:
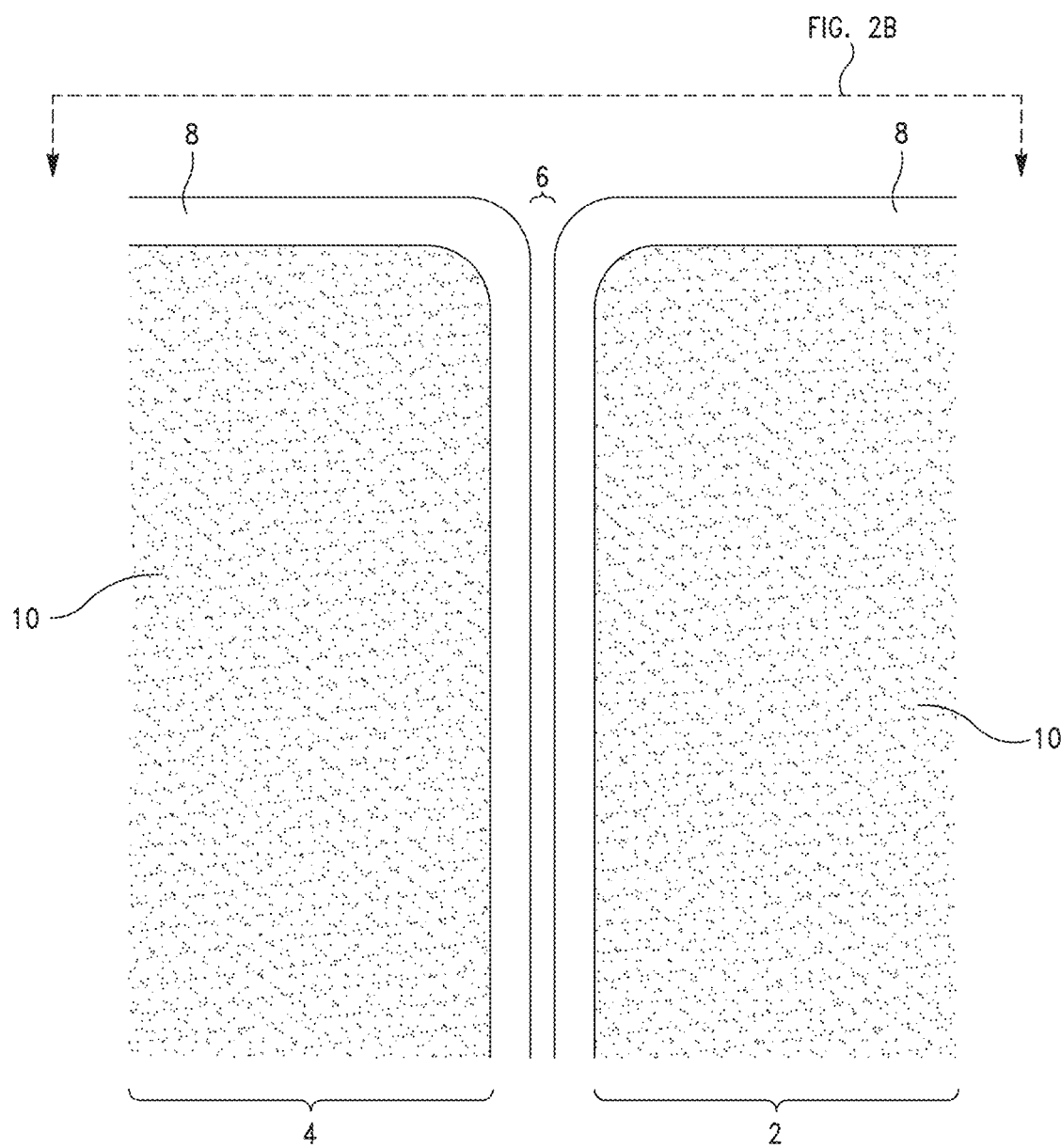
FIG. 2A is an illustration of a SI joint from a superior perspective showing tire adjoining sacrum and ilium articular surfaces.

Referring now to FIG. 2A there is shown a close-up illustration of a portion of the leftmost SI joint 6 illustrated in FIG. 1A. For illustrative simplicity, a uniform layer of cortical bone 8 is shown adjacent a deeper layer of trabecular bone 10 on both of the depicted sacrum 2 and ilium 4 portions. However, in actuality, such layers are far less uniform and homogeneous.

Figure 2B:
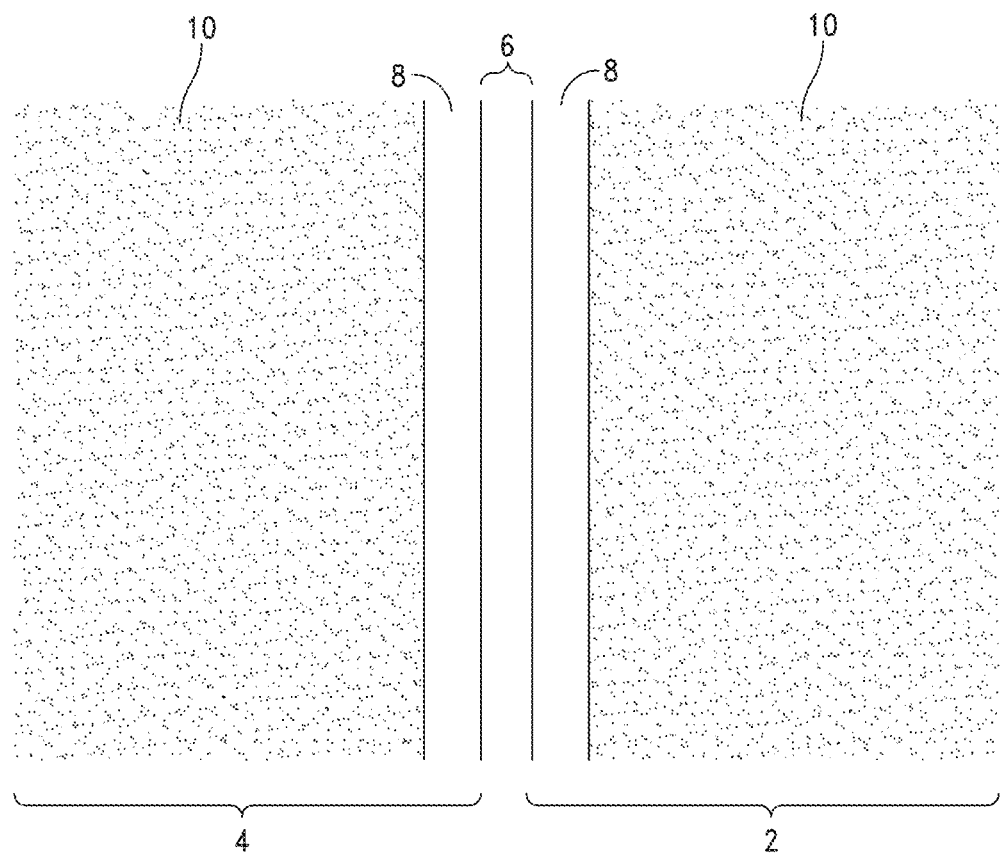
FIG. 2B is another illustration of a SI joint from a posterior perspective showing the adjoining sacrum and ilium articular surfaces.
Figure 2C:
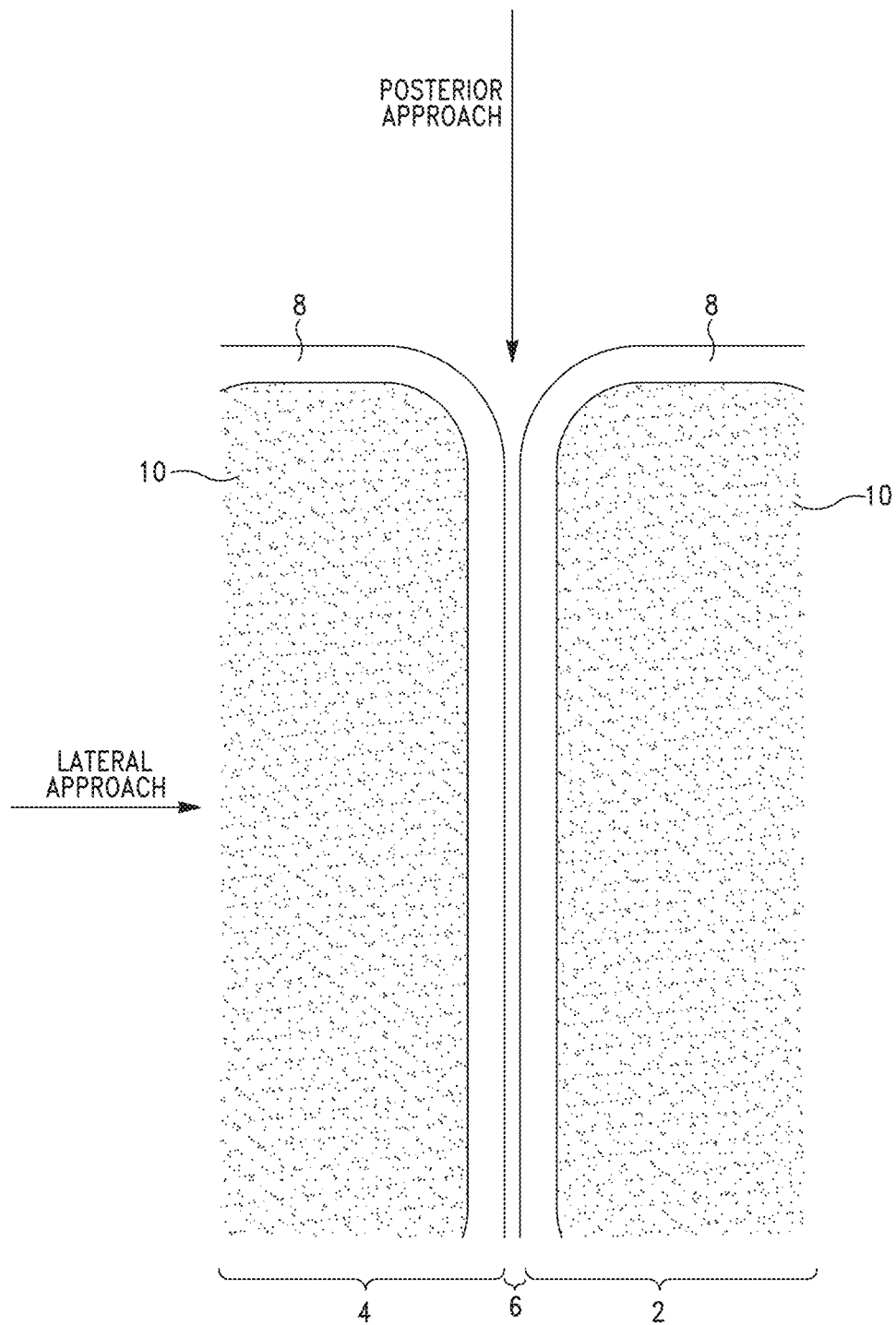
FIG. 2C is a further illustration of the SI joint shown in FIG. 2A showing lateral and posterior approaches to the SI joint, in accordance with the invention.

Referring now to FIG. 2B, there is shown a view of the same structure from a different posterior perspective. From the perspective of FIG. 2B, a posterior approach to the SI joint 6 (and, hence, a dysfunctional SI joint) would be substantially perpendicular to the page upon which FIG. 2B is printed. Indeed, referring to FIG. 2C, a variation similar to that depicted in FIG. 2A is illustrated, showing an approximate approach vector for a lateral approach to the SI joint 6 versus a posterior approach, using the orientation paradigms introduced in FIGS. 1A and 2A-2C. Such paradigm is used to illustrate various embodiments of the subject invention in various figures that follow FIGS. 1A and 2A-2C.

As indicated above, a major disadvantage associated with many conventional anterior or lateral approaches to a dysfunctional SI joint is that muscles and ligaments are typically disrupted and often damaged. Nerves and blood vessels are also susceptible to damage during such SI joint stabilization methods.

In contrast, a posterior approach to a dysfunctional SI joint is much less invasive. Indeed, less tissue and fewer muscles are disrupted, and nerves and large blood vessels are avoided.

As indicated above, in a preferred embodiment of the invention, the system for stabilizing a dysfunctional SI joint comprises a tool assembly and a prosthesis.

Referring now to FIGS. 3A-3C, 4A-4C and 5A-5B, a preferred tool assembly of the invention will be described in detail. As illustrated in FIGS. 3A-3C and 5A-5B, the tool assembly comprises an elongated guide probe 20, an SI joint opening or defect creation assembly (referred to hereinafter as "defect creation assembly") 30, and prosthesis deployment assembly 50.

Figure 3A:
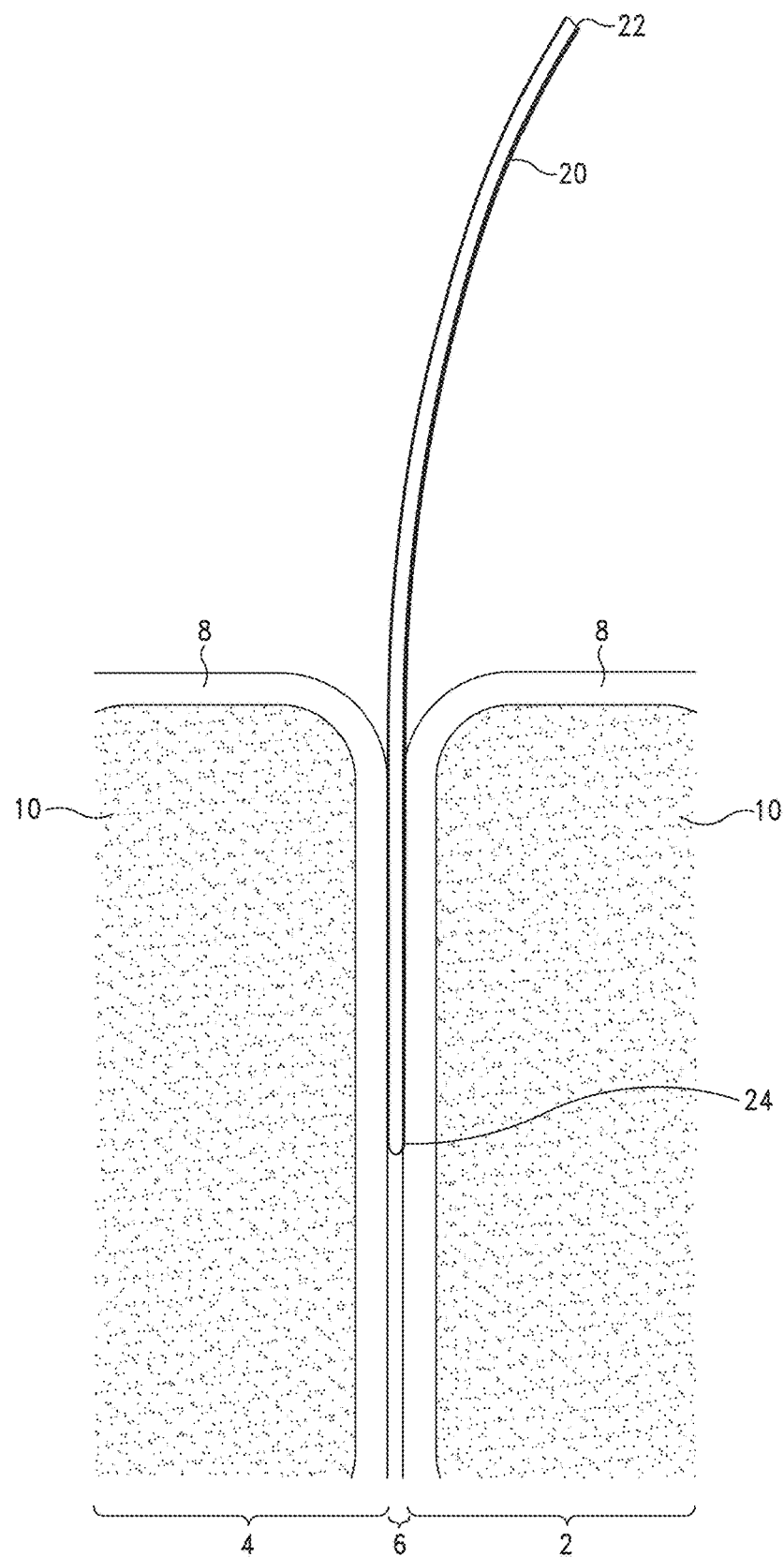
FIG. 3A is a further illustration of the SI joint shown in FIG. 2A showing an elongated guide probe of the invention positioned in the SI joint, in accordance with the invention.
Figure 3B:
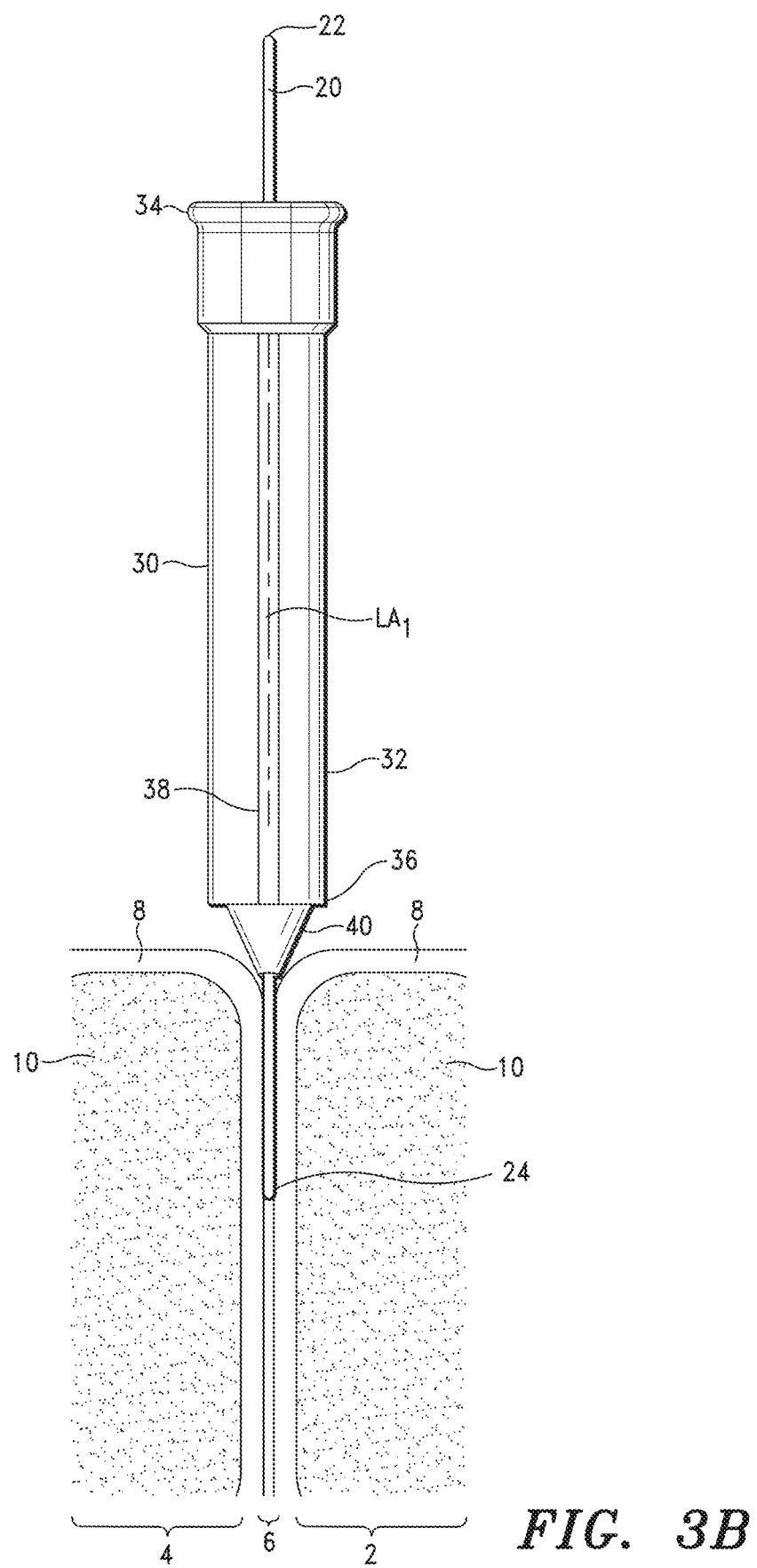
FIG. 3B is a further illustration of the SI joint shown in FIG. 3A showing one embodiment of a defect creation assembly disposed proximate the SI joint, in accordance with the invention.

Referring first to FIGS. 3A and 3B, there is shown a preferred embodiment of an elongated guide probe 20. As illustrated in FIGS. 3A and 3B, the elongated guide probe 20 comprises proximal and distal ends 22, 24.

As further illustrated in FIG. 3B, and set forth in Co-pending U.S. application Ser. No. 17/463,831, which is expressly incorporated by reference herein, the elongated guide probe 20 is sized and configured to be positioned in the dysfunctional SI joint and function as a guide for advancing the defect creation assemblies of the invention; particularly, defect creation assembly 30, into dysfunctional SI joints and placement of a prosthesis therein.

Figure 3C:
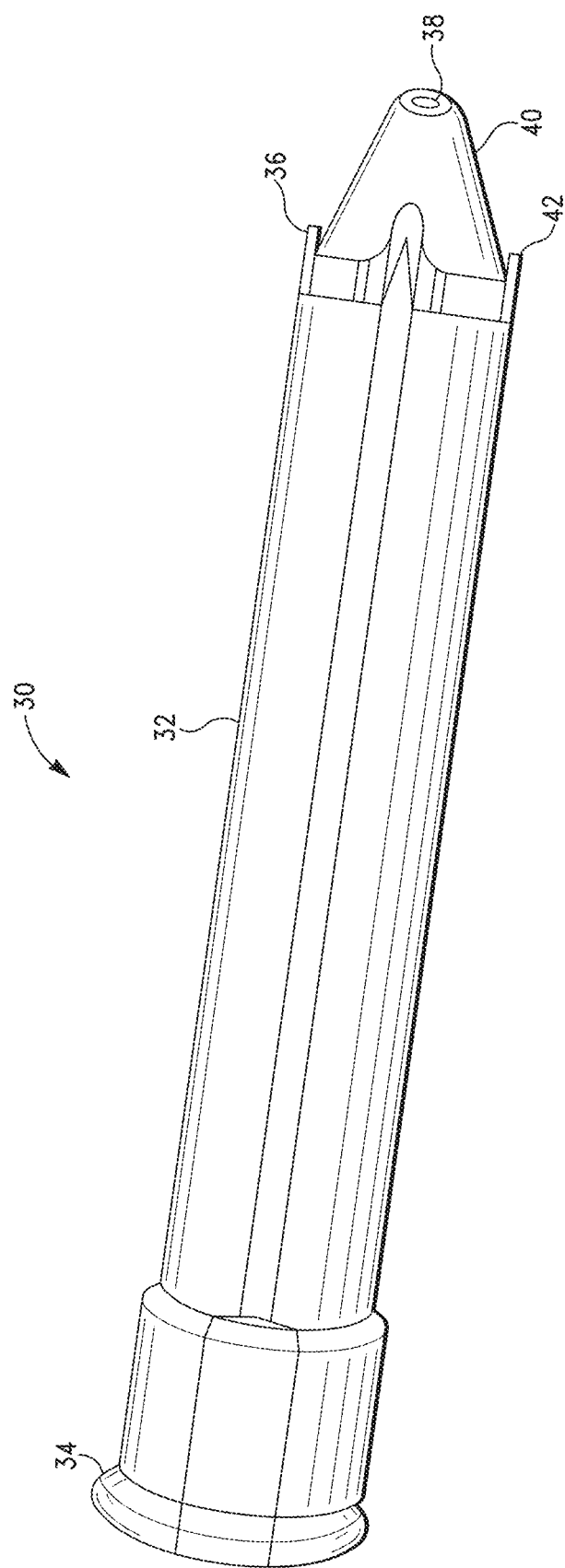
FIG. 3C is a perspective view of the defect creation assembly shown in FIG. 3B, in accordance with the invention.

Referring now to FIGS. 3B and 3C, there is shown a preferred embodiment of the defect creation assembly 30. The defect creation assembly 30 is preferably configured and adapted to create pre-determined, surgically produced open spaces or defects in the dysfunctional SI joint (referred to herein after as "pilot SI joint openings") to accommodate placement of a prosthesis of the invention therein.

As illustrated in FIGS. 3B and 3C, the defect creation assembly 30 comprises a housing 32, having a longitudinal axis $LA_1$, a proximal end 34, a distal end 36, and a guide member lumen 38 that extends through the defect creation assembly 30.

As further illustrated in FIG. 3B, the guide member lumen 38 adapted to receive said guide probe 20 therein, whereby the defect creation assembly 30 is allowed to slidably translate or be advanced along the guide probe 20 to position the defect creation assembly 30 proximate to a dysfunctional SI joint site.

The defect creation assembly 30 further comprises a bone dislodging apparatus or system 40 disposed on the defect creation assembly distal end 36, which is configured and adapted to dislodge portions of osseous tissue, i.e., bone, proximate and in the dysfunctional SI joint.

As set forth in Co-pending U.S. application Ser. No. 17/463,831, the bone dislodging system 40 can comprise various bone dislodging apparatus, such as a drill assembly and associated drill bit or orthopedic burr, which can be operated manually, pneumatically, or electromechanically. In a preferred embodiment, the bone dislodging system 40 comprises a drill assembly and associated drill bit.

As shown in greater detail in FIG. 3O, the distal end 36 of the defect creation assembly 30 can also comprise one or more teeth or apices 42 configured to assist with creation of a pilot SI joint opening in SI joint bone structures, i.e., sacrum or ilium bone structures.

As indicated above, the defect creation assemblies of the invention, including defect creation assembly 30, are preferably configured and adapted to create pilot SI joint openings in SI joint bone structures to accommodate placement of a prosthesis of the invention therein.

As also set forth in Co-pending U.S. application Ser. No. 17/463,831, the defect creation assemblies of the invention, including defect creation assembly 30, are configured and adapted to create pilot SI joint openings in SI joint bone structures of various sizes and configurations. Illustrative are the pilot SI joint openings depicted in FIGS. 11C-11E of Co-pending priority U.S. application Ser. No. 13/857,977.

Figure 4A:
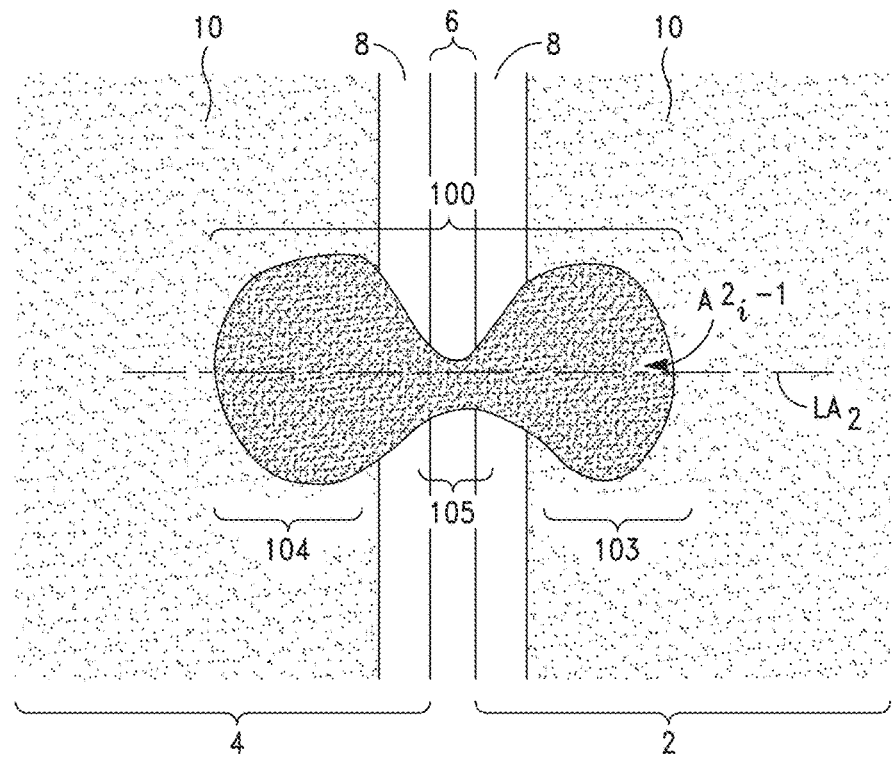
FIG. 4A is a further illustration of the SI joint shown in FIG. 2B showing one embodiment of a pilot SI joint opening, in accordance with the invention.

Referring now to FIG. 4A, there is show one embodiment of a pilot SI joint opening (denoted "100") that can be created with the defect creation assemblies of the invention; particularly, defect creation assembly 30.

As illustrated in FIG. 4A, the pilot SI joint opening 100 comprises a three-dimensional opening comprising first and second lobe regions 103, 104; the first lobe region 103 being disposed in the sacrum 2 and comprising a sacrum opening three-dimensional shape, and the second lobe region 104 being disposed in the ilium 4 and comprising an ilium opening three-dimensional shape.

As further illustrated in FIG. 4A, the three-dimensional pilot SI joint opening 100 preferably comprises an SI joint opening cross-sectional shape in a plane that intersects the sacrum 2 and ilium 4 bone structures; the plane being substantially perpendicular to the longitudinal axis $LA_1$ of the defect creation assembly 30 when the defect creation assembly 30 is disposed in a defect creation position in the dysfunctional SI joint. The three-dimensional pilot SI joint opening cross-sectional shape thus comprises the sacrum opening three-dimensional shape and ilium opening three-dimensional shape.

As additionally illustrated in FIG. 4A, the three-dimensional pilot SI joint opening 100 is defined in part by at least one noncircular cross-sectional shaped region (denoted "105") in the noted plane.

The three-dimensional pilot SI joint opening 100, i.e., cross-sectional shape thereof, also defines a cross-sectional area of the three-dimensional pilot SI joint opening cross-sectional shape (denoted "$A^2_i\text{-}1$")

The three-dimensional pilot SI joint opening 100, i.e., cross-sectional shape thereof, also comprises a longitudinal axis (denoted "$LA_2$") in the plane that intersects the sacrum 2 and ilium 4 and an initial pilot SI joint opening length along the axis $LA_2$.

Figure 4B:
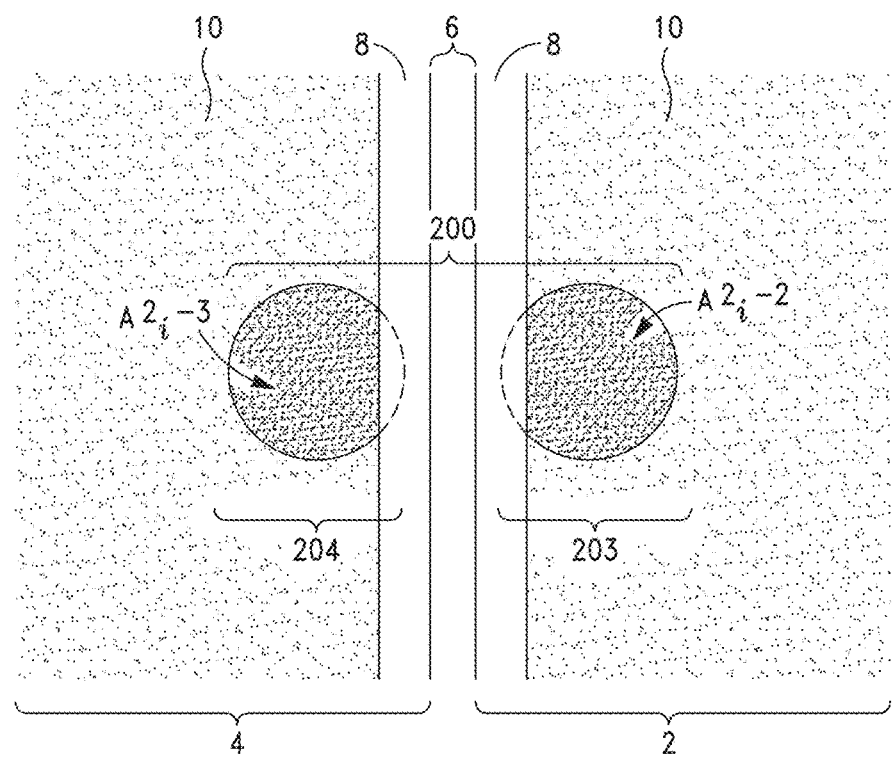
FIGS. 4B and 4C are illustrations of further embodiments of SI joint openings, in accordance with the invention.
Figure 4C:
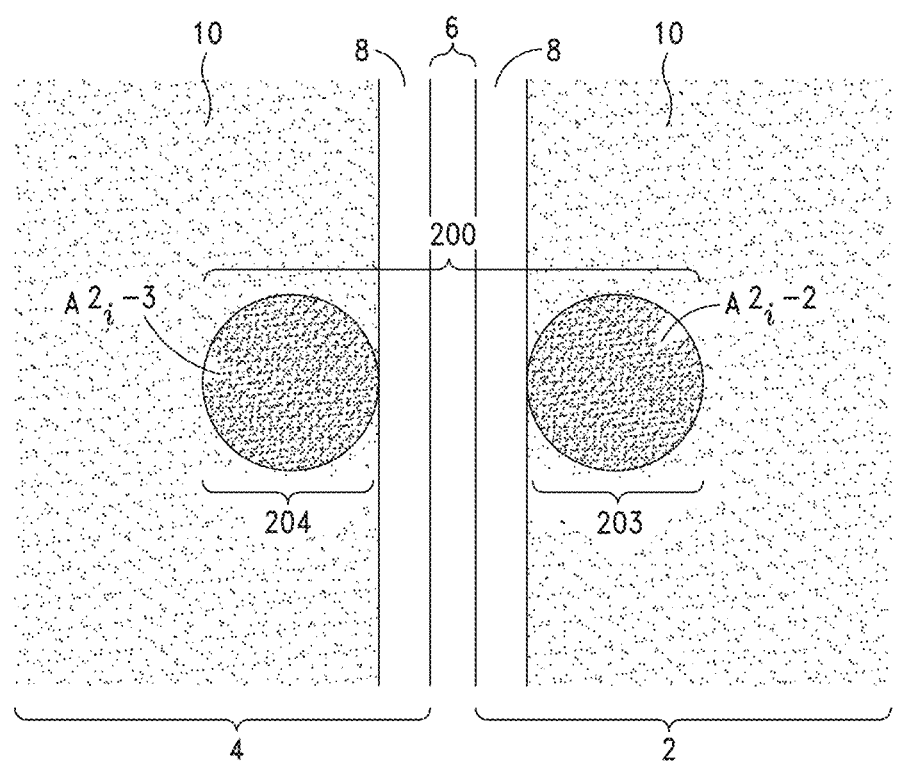

Referring now to FIG. 4B, there is shown a further pilot SI joint opening (denoted "200") that can be created with the defect creation assemblies of the invention; particularly, defect creation assembly 30.

As illustrated in FIG. 4B, the pilot SI joint opening 200 comprises two three-dimensional pilot or guide portions or regions 203, 204; the first guide portion 203 being disposed in the sacrum 2 and the second guide portion 204 being disposed in the ilium 4.

As set forth in Co-pending U.S. application Ser. No. 17/463,831, the sacrum and ilium guide portions 203, 204 can comprise various configurations, e.g., cross-sectional shapes, and sizes to, as discussed in detail below, accommodate insertion of defined regions of a prosthesis of the invention therein and transition of the sacrum and ilium guide portions 203, 204 from pilot or first configurations and sizes to expanded second configurations and sizes when the prosthesis is inserted therein.

The sacrum and ilium guide portions 203, 204 can also be disposed at various locations in the sacrum 2 and ilium 4, such as shown in FIGS. 4A and 4B.

As illustrated in FIG. 4B, the sacrum and ilium guide portions 203, 204 of the pilot SI joint opening 200 created by the defect creation assemblies of the invention; particularly, defect creation assembly 30 preferably comprise substantially circular cross-sectional shapes.

As further illustrated in FIG. 4B, the sacrum and ilium guide portions 203, 204 of the pilot SI joint opening 200, i.e., cross-sectional shape thereof, define cross-sectional areas of the sacrum and ilium guide portions 203, 204 (denoted "$A^2_i\text{-}2$" and "$A^2_i\text{-}3$", respectively).

The sacrum and ilium guide portions 203, 204 of the pilot SI joint opening 200 are also preferably disposed on a plane that similarly intersects the sacrum 2 and ilium 4.

Figure 5A:
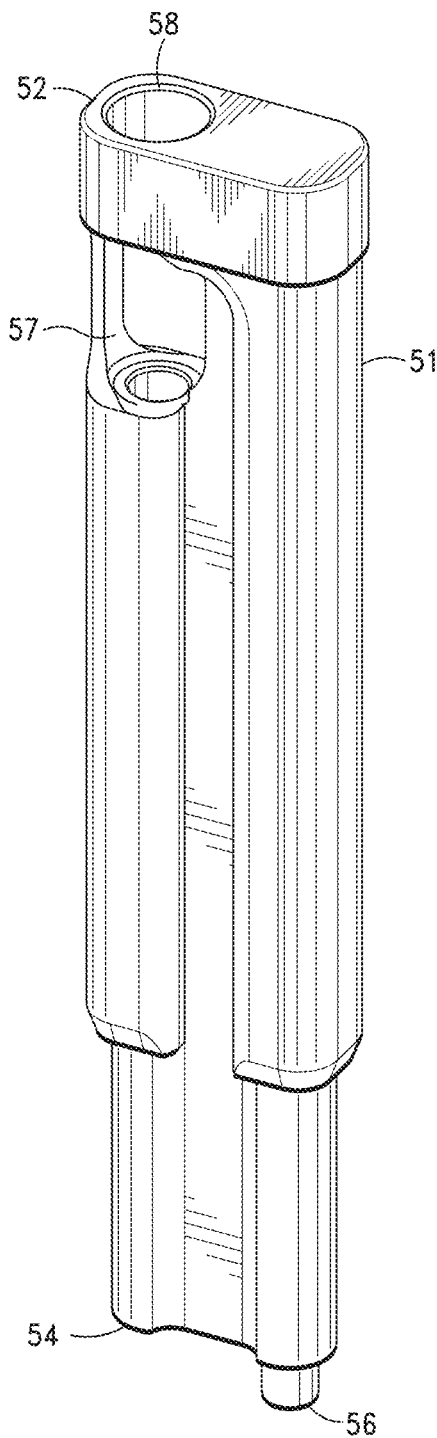
FIG. 5A is a perspective view of one embodiment of a prosthesis deployment assembly, in accordance with the invention.
Figure 5B:
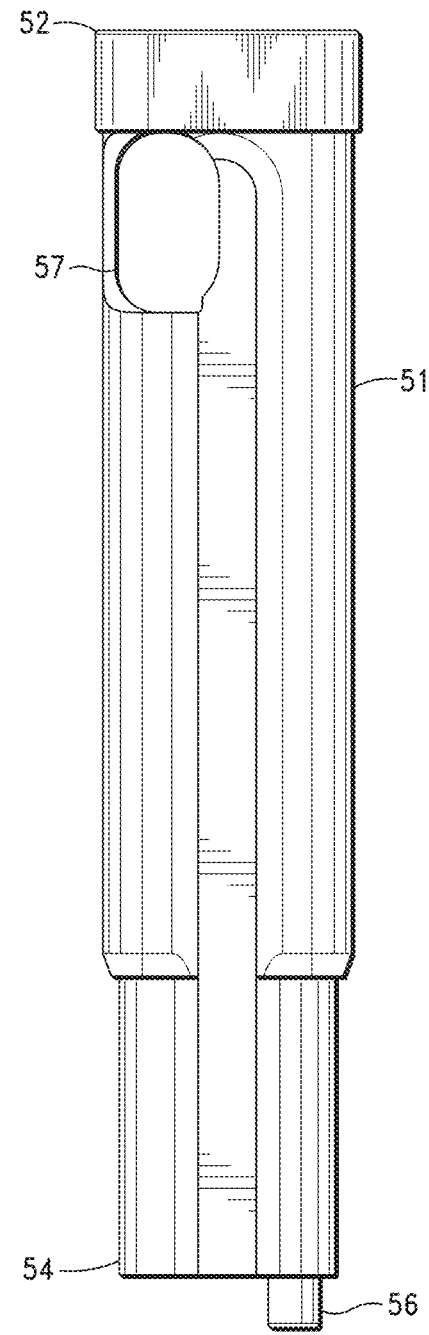
FIG. 5B is a front plan view of the prosthesis deployment assembly shown in FIG. 5A, in accordance with the invention.
Figure 5C:
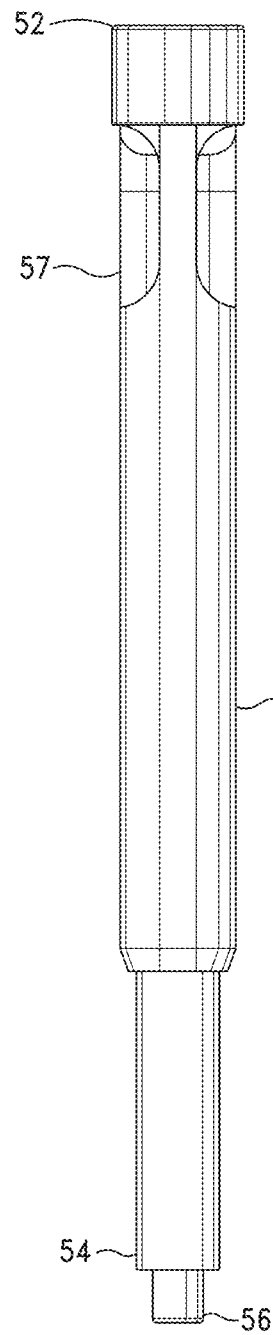
FIG. 5C is a left side plan view of the prosthesis deployment assembly shown in FIG. 5A, in accordance with the invention.
Figure 5D:
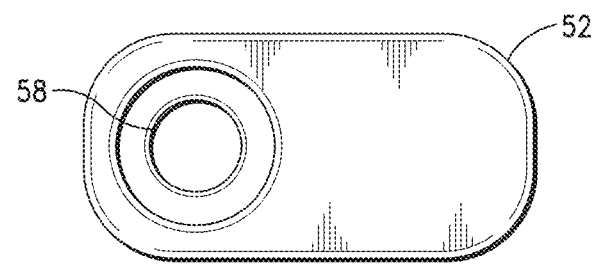
FIG. 5D is a top plan view of the prosthesis deployment assembly shown in FIG. 5A, in accordance with the invention.
Figure 5E:
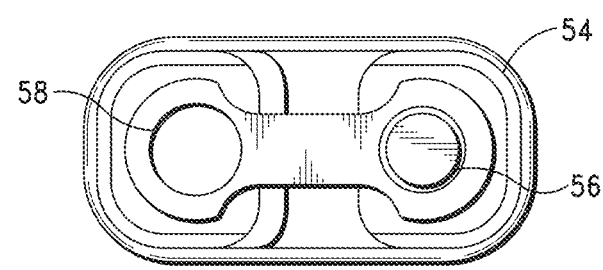
FIG. 5E is a bottom plan view of the prosthesis deployment assembly shown in FIG. 5A, in accordance with the invention.
Figure 5F:
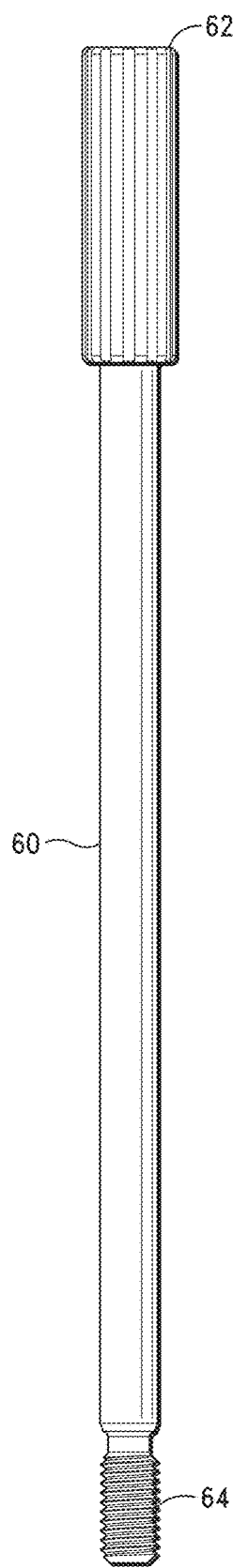
FIG. 5F is a front plan view of a prosthesis engagement rod of the prosthesis deployment assembly shown in FIG. 5A, in accordance with the invention.
Figure 5G:
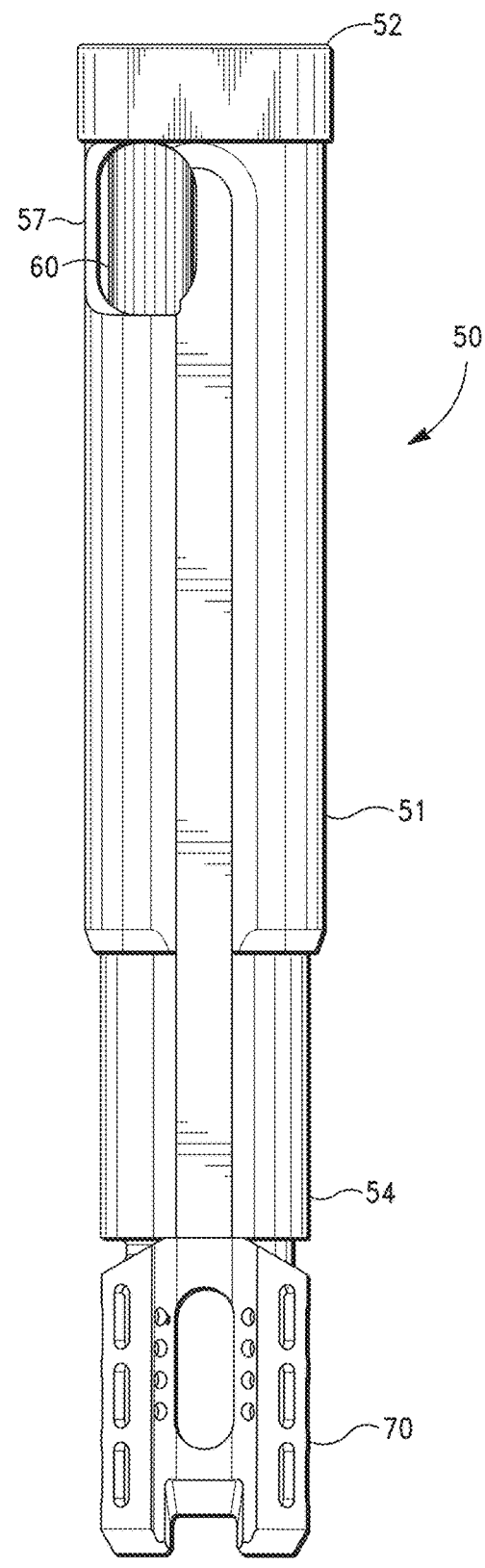
FIG. 5G is a perspective view of the prosthesis deployment assembly shown in FIG. 5A engaged to a prosthesis of the invention, in accordance with the invention.

Referring now to FIGS. 5A-5G, there is shown a preferred embodiment of a prosthesis deployment assembly of the invention (denoted "50" in FIG. 5G).

As also set forth in Co-pending U.S. application Ser. No. 17/463,831, the prosthesis deployment assembly 50 comprises prosthesis engagement means configured and adapted to connect the prosthesis deployment assembly 50 to prostheses of the invention (prosthesis 70 shown in FIG. 5G) and guide the prostheses into pilot SI joint openings created by the defect creation assembly 30.

As illustrated in FIGS. 5A-5C, the prosthesis deployment assembly 50 comprises an elongated guide member 51 comprising proximal and distal ends 52, 54.

As further illustrated in FIGS. 5B and 5E, the elongated guide member 51 further comprises a prosthesis guide pin 56 that extends from the guide member distal end 54. As discussed shown in FIG. 5G, the prosthesis guide pin 56 is sized and configured to seat in an internal prosthesis engagement member lumen 86a or 86b of the preferred prosthesis 70 of the invention.

As illustrated in FIGS. 5A, 5D and 5E, the elongated guide member 51 further comprises an internal lumen 58 that extends from the proximal end 52 of the elongated guide member 51 to the distal end 54 of the elongated guide member 51.

As illustrated in FIG. 5G, the internal lumen 58 is preferably sized and configured to receive the prosthesis engagement rod 60 (i.e., prosthesis engagement means) of the prosthesis deployment assembly 50, discussed below.

Referring now to FIG. 5F, there is shown a preferred embodiment of a prosthesis engagement rod 60 of the invention. As illustrated in FIG. 5F, the prosthesis engagement rod 60 comprises a proximal end 62 and a threaded distal end 64, which, as discussed in detail below, is sized and configured to threadably engage an internal prosthesis engagement member lumen of a prosthesis of the invention, e.g., internal prosthesis engagement member lumens 86a and/or 86b of prosthesis 70.

As further illustrated in FIG. 5F, the proximal end 62 of the prosthesis engagement rod 60 comprises a knurled configuration to facilitate threading the prosthesis engagement rod 60 into an internal prosthesis engagement member lumen of a prosthesis of the invention.

Referring back to FIGS. 5A and 5B, to further facilitate threading the prosthesis engagement rod 60 into an internal prosthesis engagement member lumen of a prosthesis of the invention, the elongated guide member 51 further comprises an access port 57 that provides access to the knurled proximal end 62 of the prosthesis engagement rod 60 when positioned in the internal lumen 58 of the elongated guide member 51, as shown in FIG. 5G.

According to the invention, the system for stabilizing dysfunctional SI joints can comprise various prostheses, which are configured and adapted to be inserted into pilot SI joint openings created by a defect creation assembly of the invention.

Suitable prostheses that are configured and adapted to be inserted info a pilot SI joint opening created by a defect creation assembly are set forth, in Co-pending priority application Ser. No. 13/857,977.

As set forth in Co-pending U.S. application Ser. No. 17/463,831, the prostheses illustrated in FIGS. 12A-12C, 13A-13B, 14A-14C and 15A-15D of Co-pending priority application Ser. No. 13/857,977 are suitable for insertion into pilot SI joint openings 100, 200 described above, and into and through articular cartilage and cortical bone (and trabecular bone), which define a SI joint.

Referring now to FIGS. 6A-6I, there is shown a preferred prosthesis 70 of the invention, which is particularly suitable for placement in pilot SI joint openings of the invention (particularly, pilot SI joint openings 100 and 200) in a SI joint, and into and through articular cartilage and bone structures (i.e., cortical and trabecular bone), which define the SI joint.

Figure 6A:
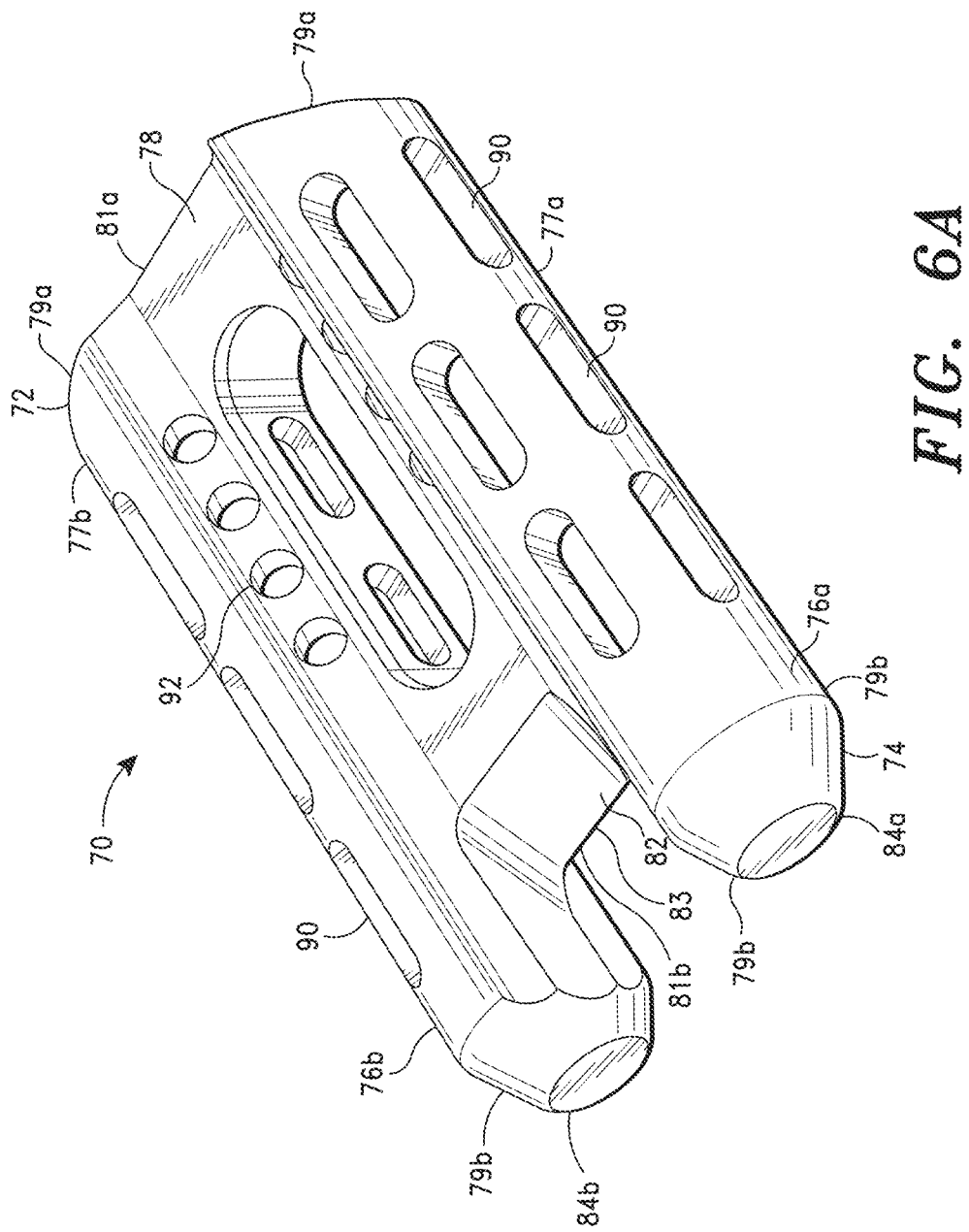
FIG. 6A is a perspective view of one embodiment of a prosthesis, in accordance with the invention.
Figure 6B:
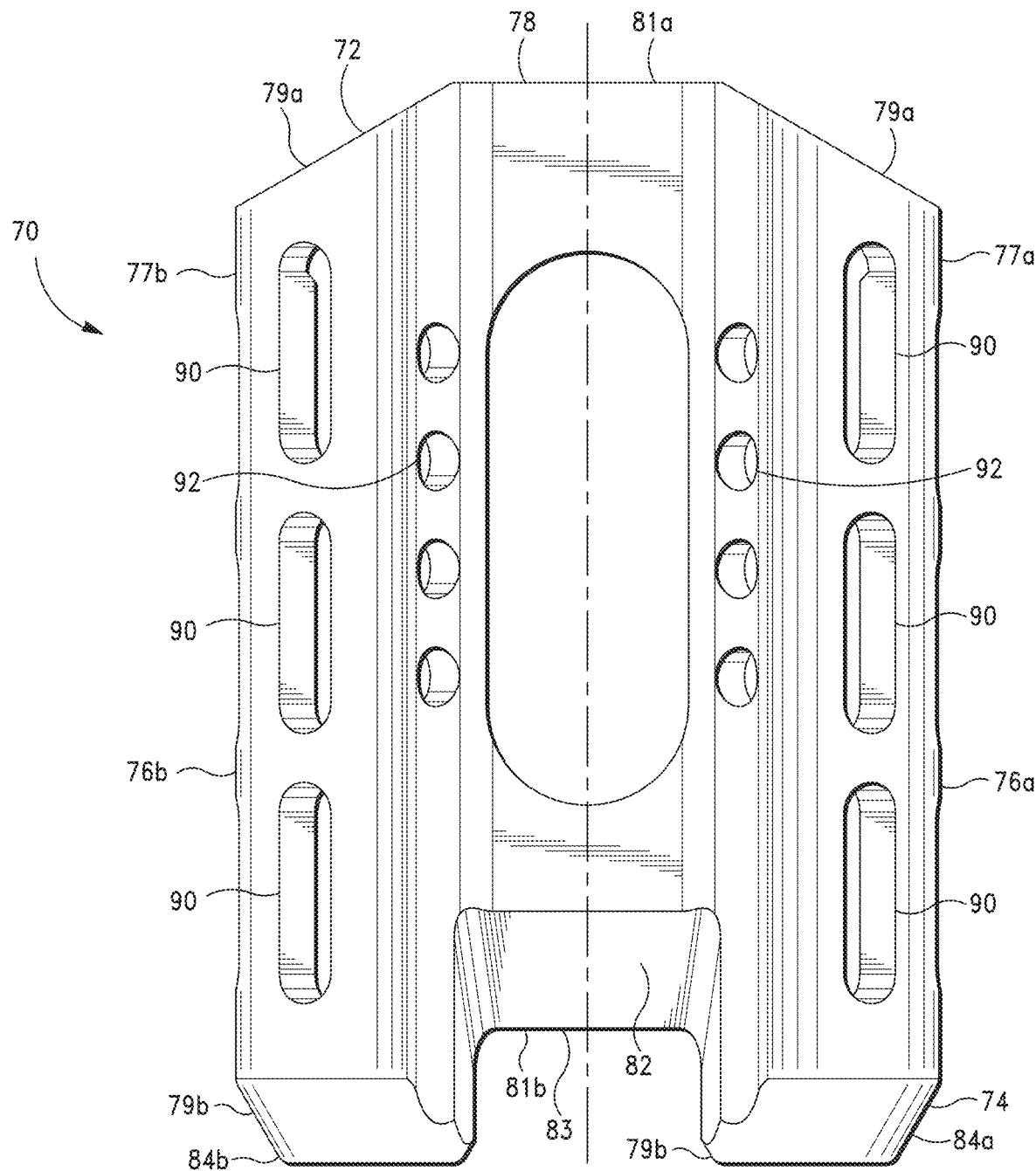
FIG. 6B is a top plan view of the prosthesis shown in FIG. 6A, in accordance with the invention.
Figure 6C:
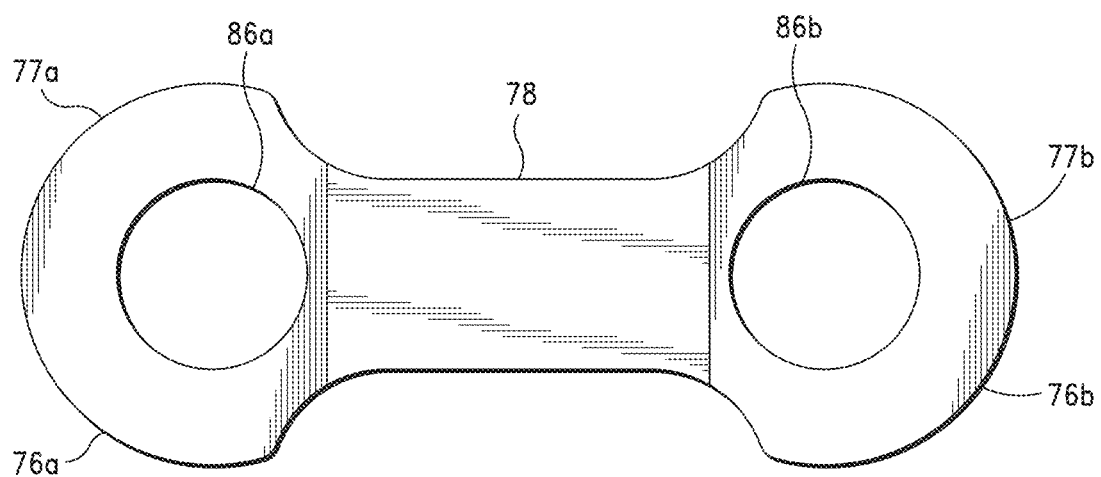
FIG. 6C is a rear plan view of the prosthesis shown in FIG. 6A, in accordance with the invention.
Figure 6D:
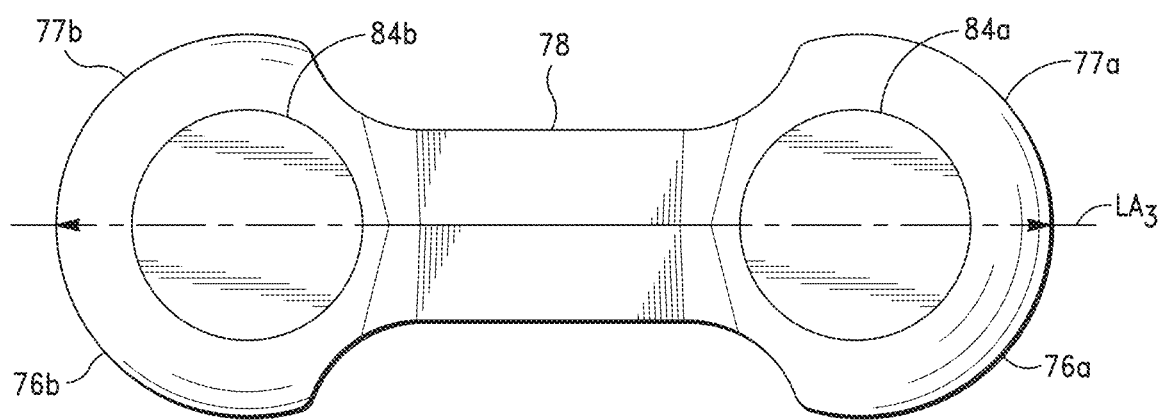
FIG. 6D is a front plan view of the prosthesis shown in FIG. 6A, in accordance with the invention.
Figure 6E:
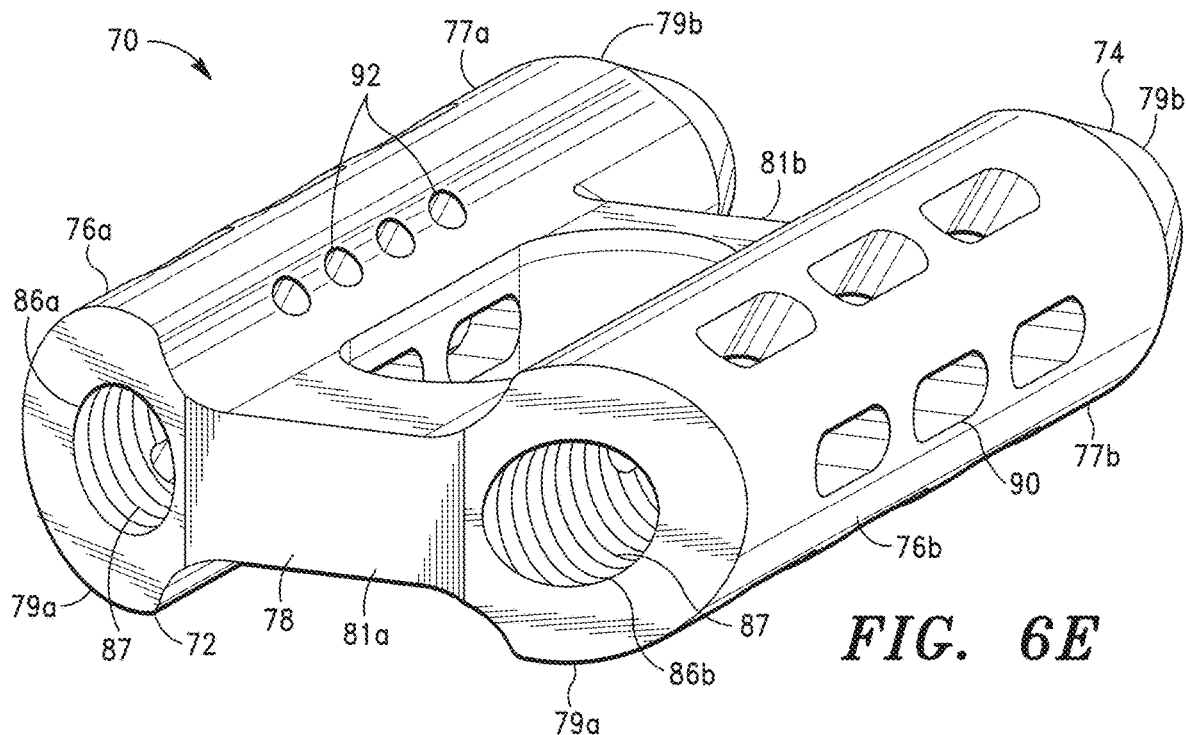
FIG. 6E is a rear perspective view of the prosthesis shown in FIG. 6A, in accordance with the invention.
Figure 6F:
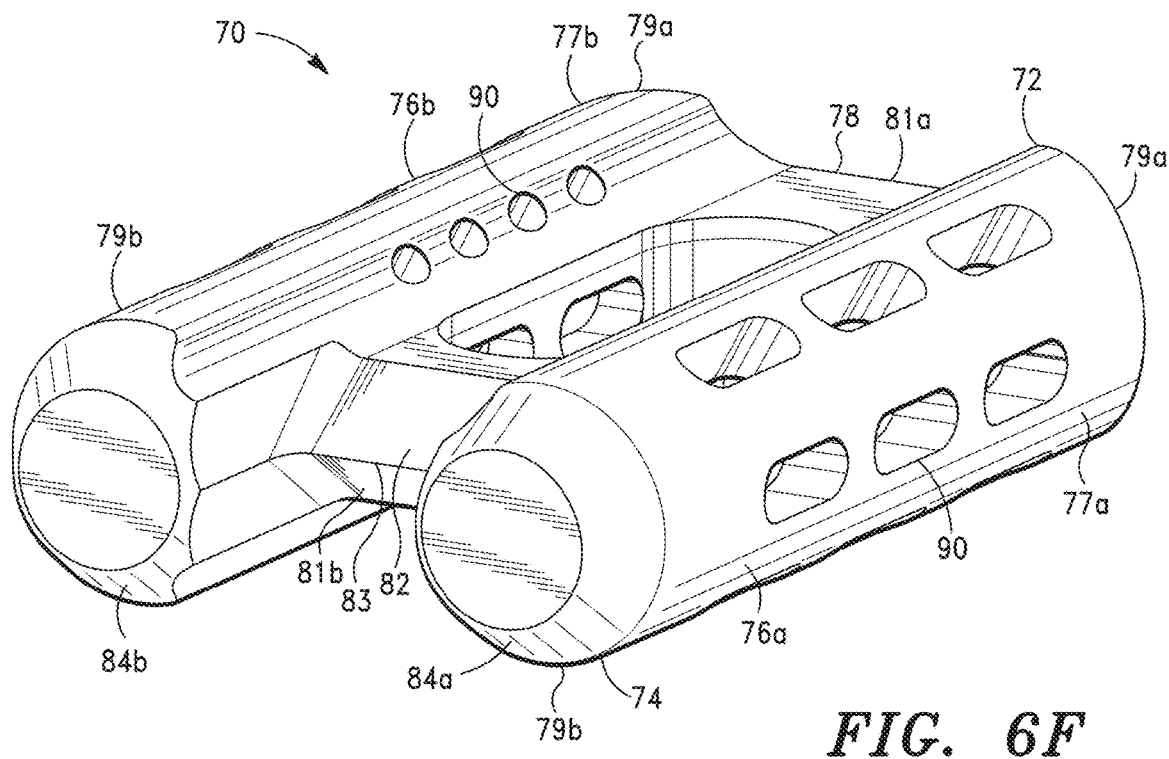
FIG. 6F is a front perspective view of the prosthesis shown in FIG. 6A, in accordance with the invention.

As illustrated in FIGS. 6A, 6E and 6F, the prosthesis 70 comprises a biocompatible and, hence, implantable member comprising proximal and distal ends 72, 74, and first and second elongated partially cylindrical sections 76a, 76b connected to a bridge section 78, whereby the prosthesis 70 comprises a continuous exterior surface comprising first and second partially cylindrical surface regions 77a, 77b.

As further illustrated in FIGS. 6A, 6E and 6F, the first and second partially cylindrical sections 76a, 76b comprise proximal and distal ends 79a, 79b. The bridge section 78 similarly comprises proximal and distal ends 81a, 81b.

As set forth in Co-pending U.S. application Ser. No. 17/463,831, the prosthesis 70 can comprise any suitable length from the proximal ends 79a to the distal ends 79b of the partially cylindrical sections 76a, 76b. In some embodiments, the prosthesis 70 comprises a length in the range of 20-50 mm, more preferably, a length in the range of 30-40 mm.

As illustrated in FIGS. 6C, 6E, 6F and FIGS. 4A and 4B, the first partially cylindrical surface region 77a preferably comprises a partially cylindrical surface region shape that corresponds to at least a portion of the first lobe region 103 of the pitot SI joint opening 100 and/or the sacrum guide portion 203 of the pilot SI joint opening 200, and/or the second lobe region 104 of the pilot SI joint opening 100 and/or the ilium guide portion 204 of the pilot SI joint opening 200, depending on the entry position of the prosthesis 70 into the pilot SI joint openings 100, 200.

The second partially cylindrical surface region 77b similarly preferably comprises a partially cylindrical surface region shape that corresponds to at least a portion of the first lobe region 103 of the pilot SI joint opening 100 and/or the sacrum guide portion 203 of the pilot SI joint opening 200, or the second lobe region 104 of the pilot SI joint opening 100 and/or the ilium guide portion 204 of the pilot SI joint opening 200, again depending on the entry position of the prosthesis 70 into the pilot SI joint openings 100, 200.

As illustrated in FIGS. 6A, 6B, 6F-6H, the distal end 81b of the bridge section 78 preferably comprises a taper region 82, which is configured and adapted to disrupt, i.e., cut into and through, articular cartilage and cortical bone 8 (and, in some aspects, trabecular bone 10), which define a SI joint.

As also set forth in Co-pending U.S. application Ser. No. 17/463,831, the taper region 82 of the bridge section 78 can comprise various configurations including, without limitation, X-bevel, wedge-shaped or bevel, including top and bottom wedge bevels, Y-bevel, including top and bottom Y-bevels, and K-bevel configurations.

In some embodiments, the taper region 82 comprises two angled regions that intersect at a central point 83, i.e., pointed proximate the mid-region of the bridge section 78, such as shown in FIGS. 6A and 6F. In some embodiments, the taper region 82 comprises a single angled or sloped region defining a plane that intersects the plane defined by the bottom surface of the prosthesis 70, i.e., wedge shaped or bevel configuration.

Figure 8A:
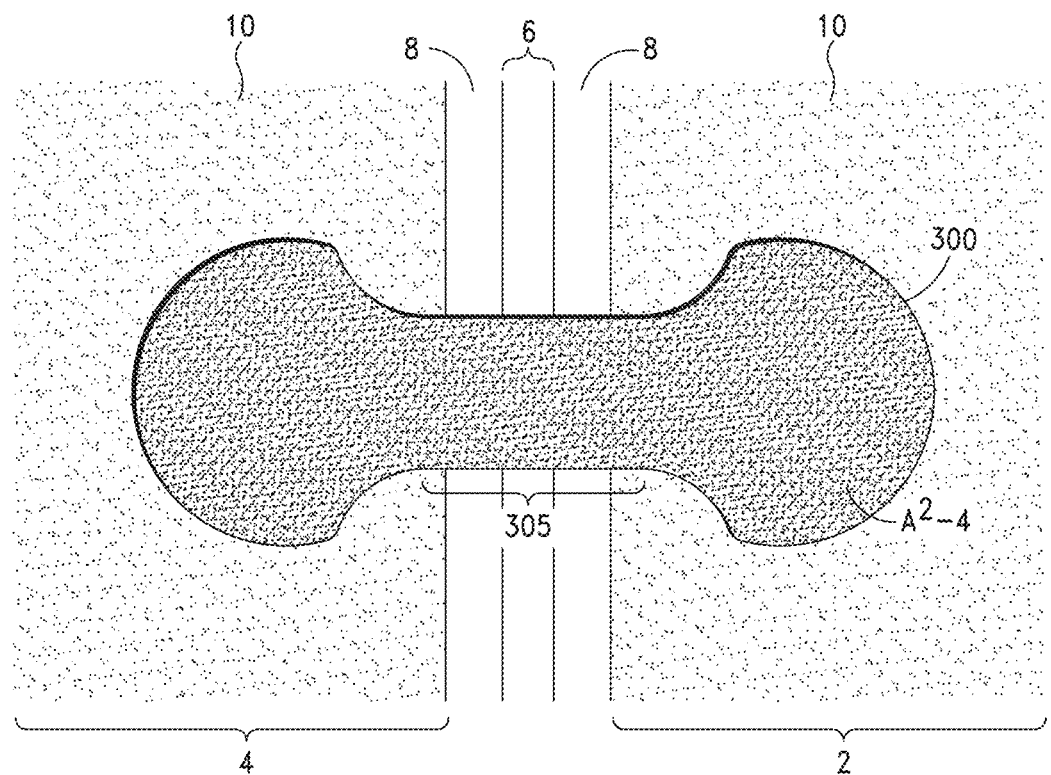
FIG. 8A is an illustration of the post-prosthesis insertion SI joint opening generated or induced when the prosthesis shown in FIG. 6A is inserted in the pilot SI joint opening shown in FIG. 4A, in accordance with the invention.
Figure 8B:
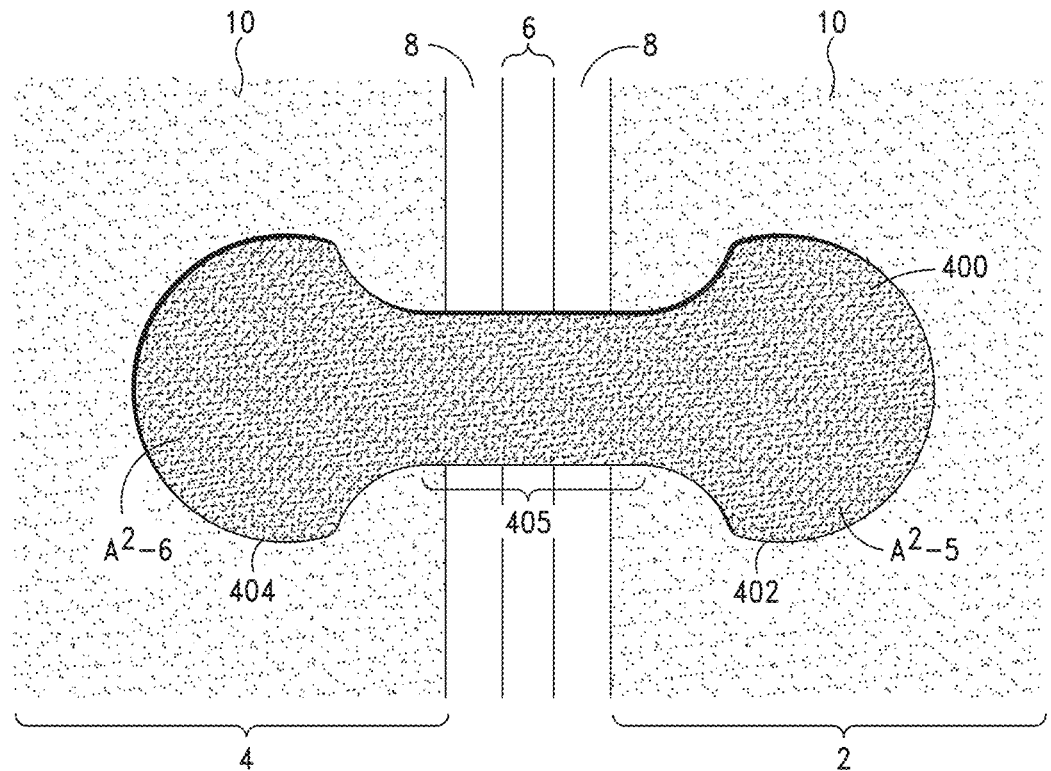
FIG. 8B is an illustration of the post-prosthesis insertion SI joint opening generated or induced when the prosthesis shown in FIG. 6A is inserted in the pilot SI joint opening shown in FIG. 4B and/or 4C, in accordance with the invention.

As further illustrated in FIG. 6A, the distal ends 79b of the first and second elongated partially cylindrical sections 76a, 76b also preferably comprise tapered regions 84a, 84b, which facilitate (i) insertion of the distal ends 79b of the first and second elongated partially cylindrical sections 76a, 76b into the first and second lobe regions 103, 104 of the pilot SI joint opening 100 and/or the sacrum and ilium guide portions 203, 204 of the pilot SI joint opening 200, and (ii) as discussed in detail below, in some embodiments, transition of the pilot SI joint opening 100 from a first configuration and size (and, hence, cross-sectional area, i.e., $A^2_i$-1 shown in FIG. 4A) to a second expanded configuration and size (and, hence, cross-sectional area, i.e., $A^2$-4 shown in FIG. 8A) when the prosthesis 70 is inserted therein, and transition of the sacrum and ilium guide portions 203, 204 of pilot SI opening 200 from first configurations and sizes (and, hence, cross-sectional areas, i.e., $A^2_i$-2 and $A^2_i$-3 shown in FIG. 4B) to expanded second configurations and sizes (and, hence, cross-sectional areas, i.e., $A^2$-5 and $A^2$-6 shown in FIG. 8B) when the prosthesis 70 is inserted therein.

As illustrated in FIGS. 6C, 6E, and 6H, the first elongated partially cylindrical section 76a of the prosthesis 70 comprises an internal prosthesis engagement member lumen 86a that extends from the proximal end 79a of the first elongated partially cylindrical section 76a.

As illustrated in FIGS. 6C and 6E, the second elongated partially cylindrical section 76b of the prosthesis 70 also comprises an internal prosthesis engagement member lumen 86b that extends from the proximal end 79a of the first elongated partially cylindrical section 76b.

In a preferred embodiment, the internal prosthesis engagement member lumens 86a, 86b of the prosthesis 70 are sized and configured to receive the prosthesis guide pin 56 of the prosthesis deployment assembly 50 and, as discussed below, the prosthesis engagement rod 60 of the prosthesis deployment assembly 50.

As set forth in Co-pending U.S. application Ser. No. 17/463,831 and illustrated in FIGS. 6E and 6G, in a preferred embodiment, the internal prosthesis engagement member lumens 86a, 86b of the first and second elongated partially cylindrical sections 76a, 76b comprise a threaded region 87 proximate the proximal end 79a that is sized and configured to receive and threadably engage the threaded distal end 64 of the prosthesis engagement rod 60 of the prosthesis deployment assembly 50 and, as discussed in detail below, the prosthesis extraction rods or screws 602a, 602b of the prosthesis extraction assembly 600.

In a preferred embodiment, the internal prosthesis engagement lumens 86a, 86b are also configured to receive agents and compositions that further facilitate adhesion of the prosthesis 70 to the pilot SI openings 100, 200 of the invention and, thereby, sacrum and/or ilium bone structures, and the aforementioned biologically active agents and compositions, including osteogenic agents and compositions, and pharmacological agents and compositions that facilitate osseous or bone tissue ingrowth into the prosthesis 70 and healing of the SI joint bone structures.

Referring back to FIGS. 6A and 6B, in a preferred embodiment, the prosthesis 70 further comprises a plurality of slots 90 and holes 92, which preferably are in communication with the internal prosthesis engagement member lumens 86a, 86b.

In a preferred embodiment, the agents and compositions referenced above are adapted to extrude through the slots 90 and holes 92 of the prosthesis 70 when the prosthesis 70 is inserted in a pilot SI joint opening (i.e., pilot SI joint openings 100 or 200), to, as indicated above, (i) further facilitate adhesion of the prosthesis 70 to the pilot SI openings 100, 200 of the invention and, thereby, sacrum and/or ilium, and (ii) facilitate osseous or bone tissue ingrowth into the prosthesis 70 and healing of the SI joint bone structures.

Figure 6I:
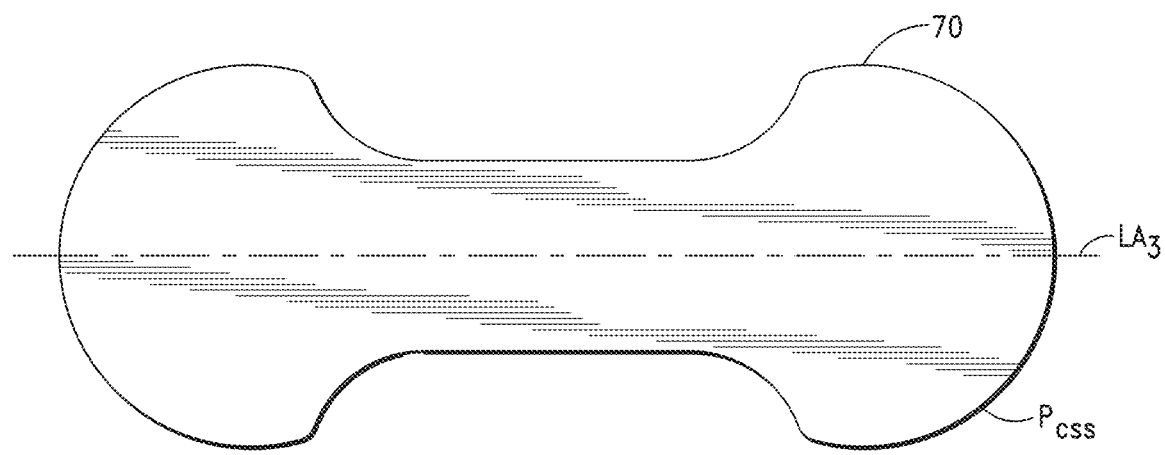
FIG. 6I is another rear plan view of the prosthesis shown in FIG. 6A showing the cross-sectional shape defined by the outer surface of the prosthesis, in accordance with the invention.

Referring now to FIG. 6I, according to the invention, the continuous exterior surface of the prosthesis 70, which is illustrated in FIGS. 6C and 6D, defines a prosthesis cross-sectional shape (denoted "$P_{CSS}$") having a longitudinal axis $LA_3$.

Figure 7A:
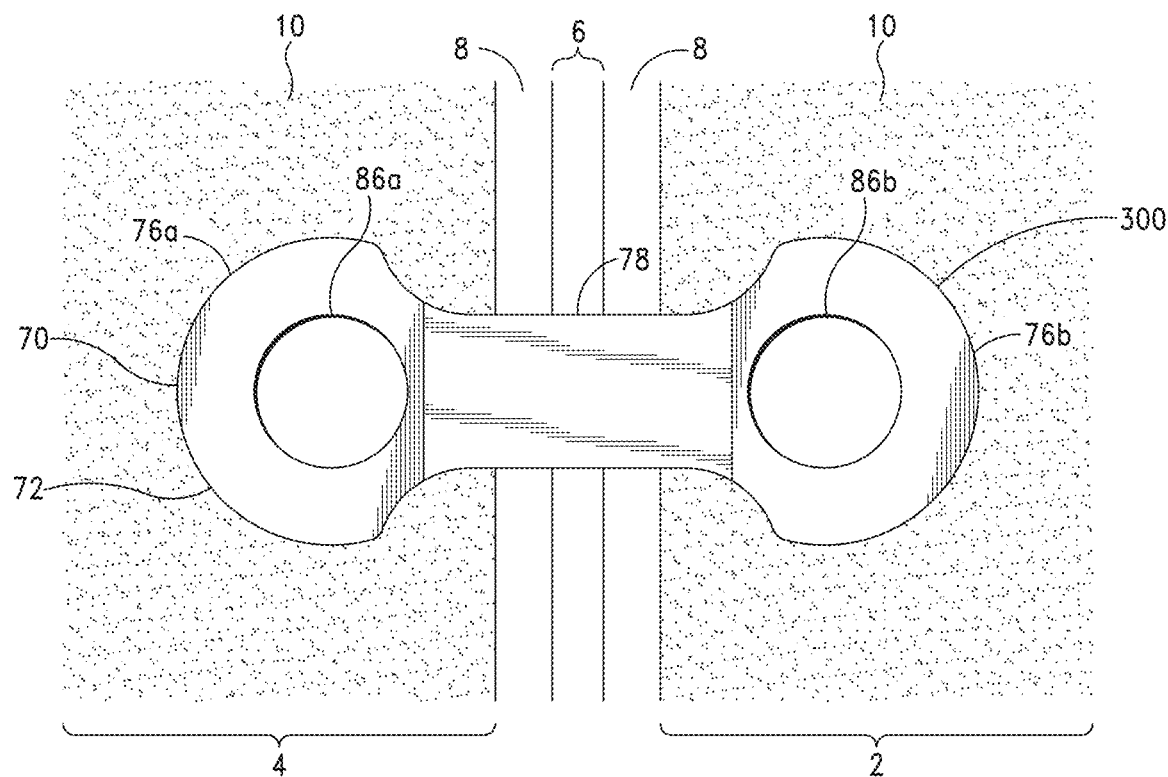
FIG. 7A is an illustration of the prosthesis shown in FIG. 6A inserted into the pilot SI joint opening shown in FIG. 4A and the resulting or induced post-prosthesis insertion SI joint opening, in accordance with the invention.

According to one embodiment, the length of the prosthesis cross-sectional shape $P_{CCS}$ along longitudinal axis $LA_3$ is greater than the length of the pilot SI joint opening 100, i.e., cross-sectional shape thereof illustrated in FIG. 4A, along the longitudinal axis $LA_2$ thereof, whereby, when the prosthesis 70 is inserted into pilot SI joint opening 100, as illustrated in FIG. 7A, the pilot SI opening 100 transitions to a post-prosthesis insertion SI joint opening 300 comprising a larger cross-sectional length shape that corresponds to the length of the prosthesis cross-sectional shape $P_{CCS}$.

As illustrated in FIG. 8A, in a preferred embodiment, when the prosthesis 70 is inserted into pilot SI joint opening 100, the cross-sectional area of the post-prosthesis insertion SI joint opening 300 also comprises a cross-sectional area (denoted "$A^2$-4") that is greater than the cross-sectional area $A^2_i$-1 of the pilot SI joint opening 100.

As further illustrated in FIG. 8A, the noncircular region 105 of pilot SI joint opening 100 also transitions to a much larger noncircular region (denoted "305"), which is achieved by virtue of the tapered bridge section 78 of the prosthesis 70 cutting info and through the articular cartilage and cortical bone 8, which define the SI joint 6, and the trabecular bone 10 proximate the SI joint 6.

Figure 7B:
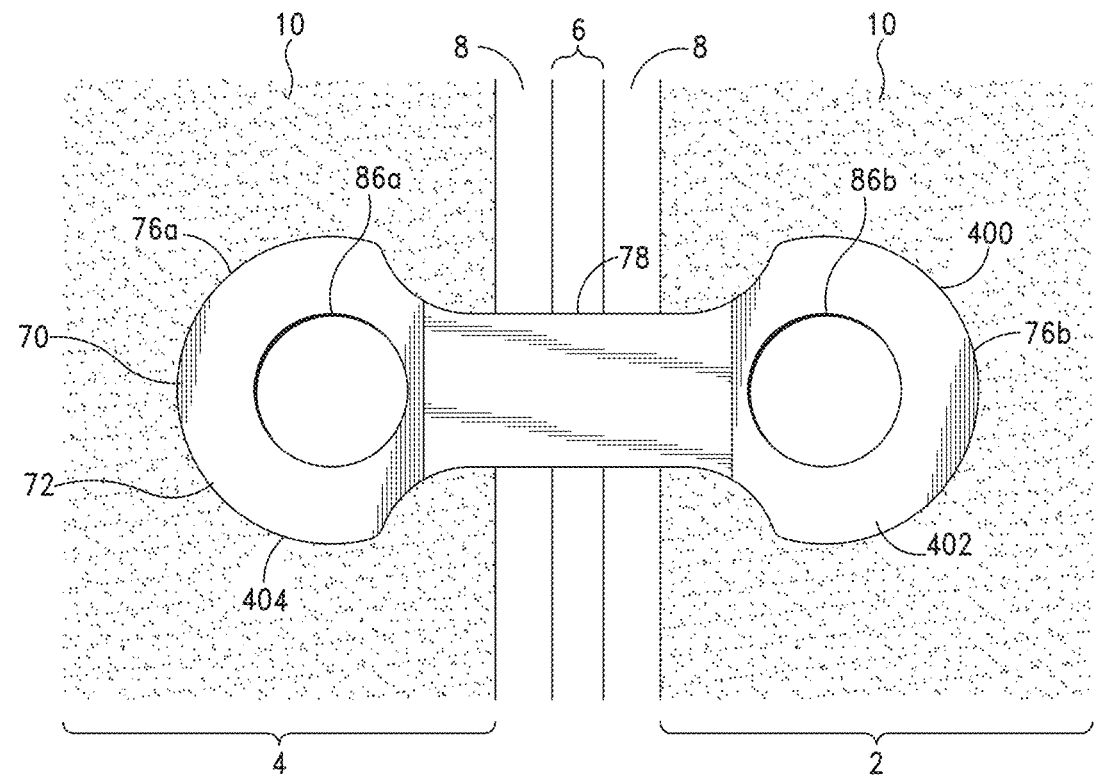
FIG. 7B is an illustration of the prosthesis shown in FIG. 6A inserted in the pilot SI joint opening shown in FIG. 4B and the resulting or induced post-prosthesis insertion SI joint opening, in accordance with the invention.

As set forth in Co-pending U.S. application Ser. No. 17/463,831, when the prosthesis 70 is inserted into pilot SI joint opening 200, as illustrated in FIG. 7B, the pilot SI joint opening 200 similarly transitions to a post-prosthesis insertion SI joint opening 400, wherein, as illustrated in FIG. 8B, the cross-sectional areas of the post-prosthesis sacrum and ilium guide portions of the post-prosthesis insertion SI joint opening 400 (now denoted "402" and "404", respectively) comprise greater cross-sectional areas (denoted "$A^2$-5" and "$A^2$-6").

As further illustrated in FIG. 8B, the post-prosthesis insertion SI joint opening 400 also comprises a noncircular region (denoted "405"), which is similarly achieved by virtue of the tapered bridge section 78 of the prosthesis 70 cutting into and through the articular cartilage and cortical bone 8, which define the SI joint 6, and the trabecular bone 10 proximate the SI joint 6.

As illustrated in FIGS. 6I, 8A and 8B, the post-prosthesis insertion SI joint openings 300, 400 also comprise cross-sectional shapes that correspond to the prosthesis cross-sectional shape "$P_{CSS}$" defined by the outer surface of the prosthesis 70, including the first and second elongated partially cylindrical sections 76a, 76b and bridge section 78.

In a preferred embodiment, to achieve sufficient expansion of the pilot SI joint openings 100, 200 when the prosthesis 70 is inserted therein, preferably, the cross-sectional areas of the regions defined by the first and second elongated partially cylindrical sections 76a, 76b of the prosthesis 70 are at least 0.05% greater than the cross-sectional areas defined by the first and second lobe regions 103, 104 of the pilot SI joint opening 100, and the cross-sectional areas defined by the sacrum and ilium guide portions 203, 204 of pilot SI joint opening 200.

In some embodiments, the cross-sectional areas of the regions defined by the first and second elongated partially cylindrical sections 76a, 76b of the prosthesis 70 are substantially equal to or slightly smaller, e.g., ≤0.05%, than the cross-sectional areas defined by the first and second lobe regions 103, 104 of the pilot SI joint opening 100, and the cross-sectional areas defined by the sacrum and ilium guide portions 203, 204 of pilot SI joint opening 200.

As also set forth in Co-pending U.S. application Ser. No. 17/463,831, the prosthesis 70, as well as the prostheses disclosed in Co-pending priority application Ser. No. 13/857,977, can comprise various biocompatible materials, including metals and metal alloys, such as titanium, stainless-steel, cobalt-chromium alloys and nickel-titanium alloys.

The prosthesis 70, as well as the prostheses disclosed in Co-pending application Ser. No. 13/857,977, can also comprise various biocompatible polymers, including, without limitation, reinforced polymers, such as carbon fiber reinforced polymers and metal-framed polymers.

The prosthesis 70, as well as the prostheses disclosed in Co-pending priority application Ser. No. 13/857,977, can also comprise a porous structure to facilitate (i) adhesion of the prosthesis 70 to a post-prosthesis insertion SI joint opening of the invention; particularly, post-prosthesis insertion SI joint openings 300, 400 and, thereby, to SI joint bone structures, i.e., sacrum and ilium bone structures, and (ii) bone or osseous tissue ingrowth into the prosthesis 70.

The prosthesis 70, as well as the prostheses disclosed in Co-pending priority application. Ser. No. 13/857,977, can further comprise various exterior surface textures and roughness to facilitate or enhance engagement of the prosthesis to a post-prosthesis insertion SI joint opening, such as post-prosthesis insertion SI joint openings 300, 400, and, thereby, to SI joint bone structures, i.e., sacrum and ilium bone structures, and/or maintain engagement thereto and positioning therein. The surface of the prosthesis 70 (as well as the prostheses disclosed in Co-pending priority application Ser. No. 13/857,977) can, thus, comprise a roughness grade number of N1 (Ra=~0.025 µm), N2 (Ra=~0.05 µm), M3 (Ra=~0.1 µm), N4 (Ra=~0.2 µm), N5 (Ra=~0.4 µm), N6 (Ra=~0.08 µm), N7 (Ra=~1.6 µm), N8 (Ra=~3.2 µm), N9 (Ra=~6.3 µm), N10 (Ra=~12.5 µm), N11 (Ra=~25 µm) or N12 (Ra=~50 µm).

In some embodiments, the prosthesis 70, as well as the prostheses disclosed in Co-pending priority application Ser. No. 13/857,977, further comprise an outer coating.

In some embodiments, the outer coating comprises a biocompatible and, preferably, biodegradable adhesive composition. According to the invention, suitable adhesive compositions include, without limitation, poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol and combinations thereof; fibrin-based compositions, collagen-based compositions, including collagen and poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and Octyl-Seal); polyethylene glycol) (PEG) based compositions, including FocalSeal®, Progel™, Duraseal™, DuraSeal™ Xact, Coseal® and ReSure Sealant, polysaccharide-based compositions, polypeptide-based compositions, and radiation curable materials, such as poly(glycerol-co-sebacate) acrylate (PGSA), discussed below.

In some embodiments, the outer coating comprises a biologically active composition comprising one of the aforementioned biologically active agents or a pharmacological composition comprising one of the forementioned pharmacological agents.

In some embodiments, the outer coating comprises one of the aforementioned polymers and/or compositions comprising same.

In some embodiments, the aforementioned polymer compositions comprise one or more of the aforementioned biologically active agents or pharmacological agents.

In some embodiments of the invention, the polymer comprises poly(glycerol sebacate) (PGS) or a derivative thereof, including, without limitation, poly(glycerol-co-sebacate) acrylate (PGSA) and PGS co-polymers, such as poly(glycerol sebacate)-co-poly(ethylene glycol) (PGS-PEG); and/or composites thereof, e.g., PGS-hydroxyapatite (HA) composites and PGS-poly(ε-caprolactone) (PGS-PCL) composites, and compositions comprising same.

As set forth in Co-pending U.S. application Ser. No. 17/463,831, PGS and derivatives thereof possess a unique property of inducing remodeling of damaged osseous or bone tissue, such as at pilot SI joint openings, and, hence, healing of the associated bone structures when disposed proximate thereto.

As set forth in Loh, et al., Poly(glycerol sebacate) *Biomaterial: Synthesis and Biomedical Applications*, Journal of Materials Chemistry B, vol. 3(39), pp. 7641-7652 (2015) and indicated in Table 1 below, a further seminal property of PGS is that its physical state can be modulated during synthesis by controlling the "degree of esterification" via at least one crosslinking agent, e.g., methylene diphenyl diisocyanate (MDI).

TABLE 1

| Degree of Esterification | Physical State |
|---|---|
| ≤46% | Solid (Brittle Wax) |
| ~47%-64% | Semi-Solid (Soft Wax) |
| ~65%-75% | Viscous Liquid |
| ~76%-83% | Sticky Elastomer |
| ≥84% | Elastomer |

As set forth in Co-pending U.S. application. Ser. No. 17/463,831, any suitable degree of esterification of PGS can be employed for PGS when employed in or for PGS based outer coatings (I.e., polymer compositions comprising PGS) and biologically active agent compositions of the invention.

In some embodiments, the PGS based outer coatings comprise a degree of esterification in the range of ~76%-83%, whereby the PGS exhibits adhesive properties, which will enhance engagement of prosthesis 70 (as well as the prostheses disclosed in Co-pending priority application Ser. No. 13/857,977) to the post-prosthesis insertion SI joint openings 300, 400 and, thereby, to the SI joint bone structures, i.e., sacrum and ilium bone structures.

As is well established, the physical state of poly(glycerol-co-sebacate) acrylate (PGSA) can also be modulated by combining the PGSA with a suitable photoinitiator and subjecting the PGS A to radiation.

Indeed, as set forth in Nijst, et al., *Synthesis and Characterization of Photocurable Elastomers from Poly(Glycerol-Co-Sebacate)*, Biomacromolecules, vol. 8, no. 10, pp. 3067-3073 (2007), PGSA can be induced to transition from a liquid or flowable state to a solid elastomer state when combined with a photoinitiator, such as 2-hydroxy-1-[4-hydroxyethoxy) phenyl]-2-methyl-1-propanone (D 2959, Ciba Geigy), 2,2-dimethoxy-2-phenylacetophenone, titanocenes, fluorinated diaryltitanocenes, iron arene complexes, manganese decacarbonyl and methylcyclopentadienyl manganese tricarbonyl, and subjected to radiation, such as visible light; particularly, radiation in the range of approximately 380-750 nm, and ultraviolet (UV) light, particularly, radiation in the range of 10-400 nm.

Thus, in some embodiments, a composition comprising PGSA (also referred to herein as a "PGSA based composition" and "fixation composition") is employed to enhance the engagement of the prosthesis 70 to a post-prosthesis insertion SI joint opening, such as post-prosthesis insertion SI joint openings 300, 400, and, thereby, SI joint bone structures, i.e., sacrum and ilium bone structures.

In such embodiments, the PGSA based composition (in a flowable state) is disposed in the internal prosthesis engagement member lumens 86a, 86b of the prosthesis 70, whereby the PGSA based composition is dispersed when the prosthesis 70 is positioned in the dysfunctional SI joint and fills any gaps between the prosthesis 70 and a post-prosthesis insertion SI joint opening of the invention; particularly, post-prosthesis insertion SI joint openings 300, 400, and thereafter cured via radiation and solidified, whereby the solidified PGSA enhances the engagement of the prosthesis 70 to the post-prosthesis insertion SI joint opening and, thereby, to the sacrum and ilium bone structures.

According to the invention, the PGSA fixation concept described above can also be readily employed in other prostheses configured and/or adapted to stabilize bone structures and joints defined thereby, including and in addition to sacrum and ilium bone structures and SI joints defined thereby, e.g., vertebral bone structures and vertebral joints defined thereby, and tarsal bone structures and tarsal joints (e.g., tarsometatarsal joints, intermetatarsal joints and metatarsophalangeal joints) defined thereby, which comprise at least one internal cavity configured to receive a fixation composition of the invention therein and means for dispersing the fixation composition into one or more gaps or cavities between an exterior region of the prostheses and an adjoining surface of a bone structure when the prostheses are inserted therein. By way of example, such prostheses can comprise a simple pin structure with an internal lumen configured to receive a fixation composition of the invention therein and a plurality of slots that extend through the pin structure and are in communication with the internal lumen to facilitate dispersal of the fixation composition out of the pin structure and into one or more gaps between an exterior region of the pin structure and an adjoining surface of a bone structure when the pin structure is inserted therein.

PGS and its derivatives; particularly, PGSA are also excellent platforms for delivery and, hence, administration of biologically active agents and pharmacological agents to mammalian tissue, including osseous or bone tissue.

Thus, in some embodiments of the invention, the PGS based outer coatings and PGS and PGS A based compositions further comprise one or more of the aforementioned biologically active or pharmacological agents.

In some embodiments, the system for stabilizing dysfunctional SI joints further comprises an image capture apparatus configured and adapted to capture images reflecting positions and/or orientations of the elongated guide probe and/or defect creation assembly when disposed in the body, and, particularly, during advancement of the elongated guide probe and defect creation assembly toward and into the dysfunctional SI joint.

As set forth in Co-pending U.S. application Ser. No. 17/463,831, suitable image capture apparatus comprise a fluoroscope, a CT system, an ultrasound system, a radiography system, and a magnetic resonance imaging system.

In some embodiments, the system for stabilizing dysfunctional SI joints further comprises a drill guide assembly that facilitates proper placement of (i) the elongated guide probe 20 in the dysfunctional SI joint, and (ii) the pilot SI joint openings 100, 200 of tire invention and, hence, sacrum and ilium portions thereof, and, thereby, placement of the prosthesis 70 (and other prostheses described in Co-pending U.S. application Ser. No. 13/857,977) in the dysfunctional SI joint.

Figure 9A:
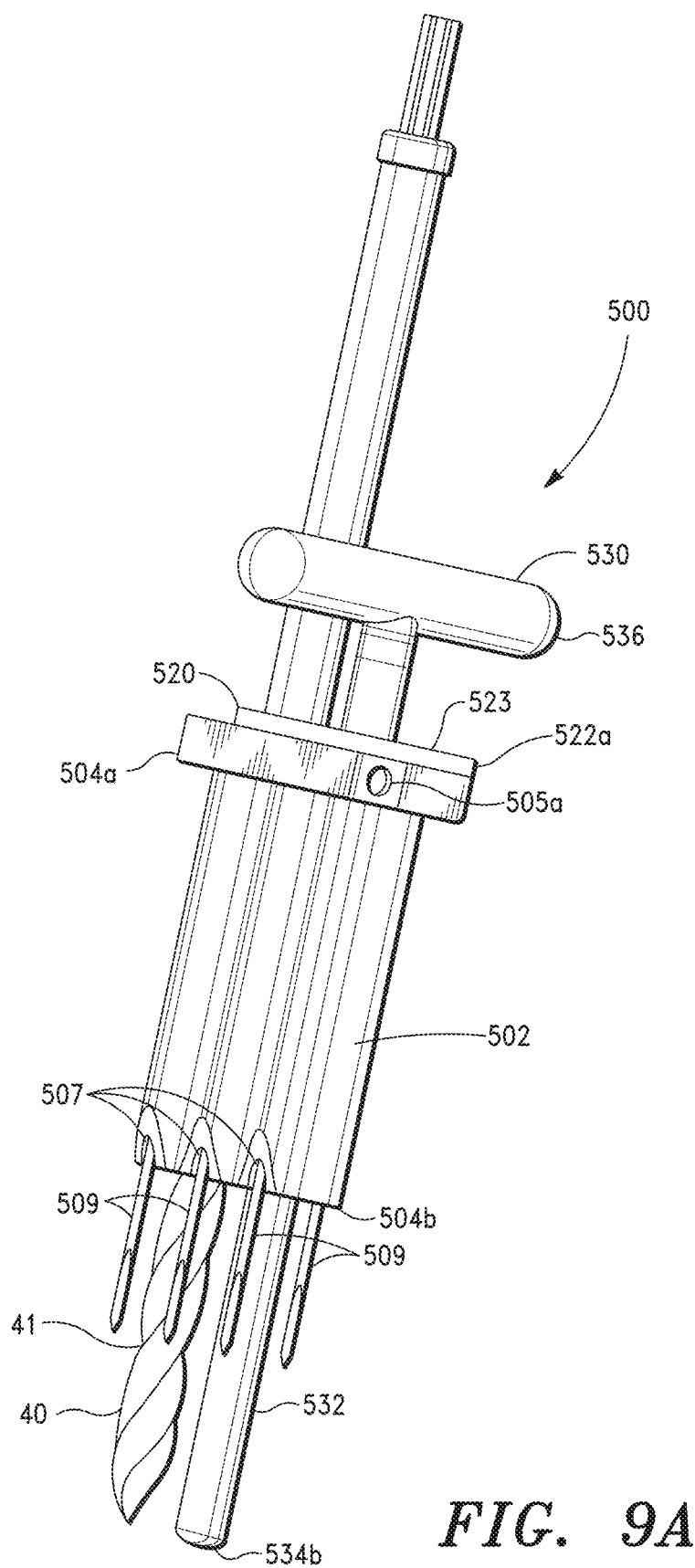
FIG. 9A is a perspective view of one embodiment of drill guide assembly, in accordance with the invention.

Referring now to FIG. 9A, there is shown a preferred embodiment of a drill guide assembly 500.

As illustrated in FIG. 9A, the drill guide assembly 500 comprises an access sleeve 502, drill guide 520 and a guide pin 530.

Figure 9B:
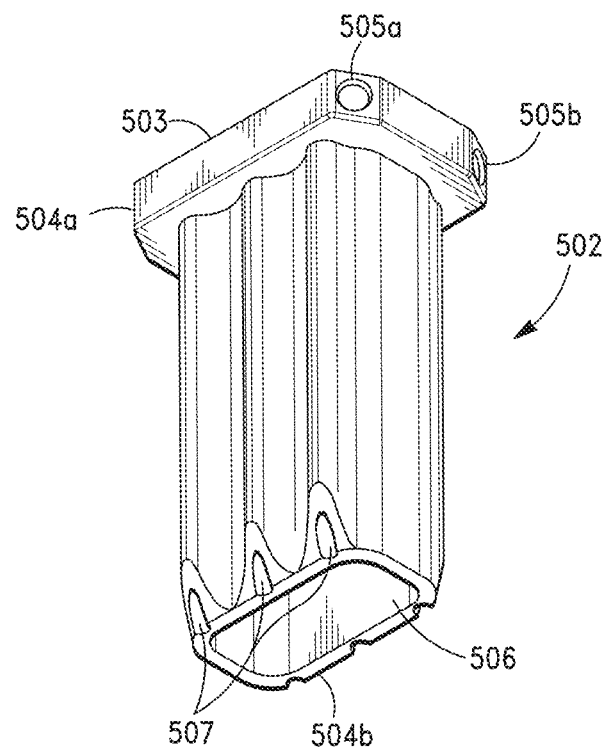
FIG. 9B is a perspective view the access sleeve of the drill guide assembly shown in FIG. 9A, in accordance with the invention.
Figure 9C:
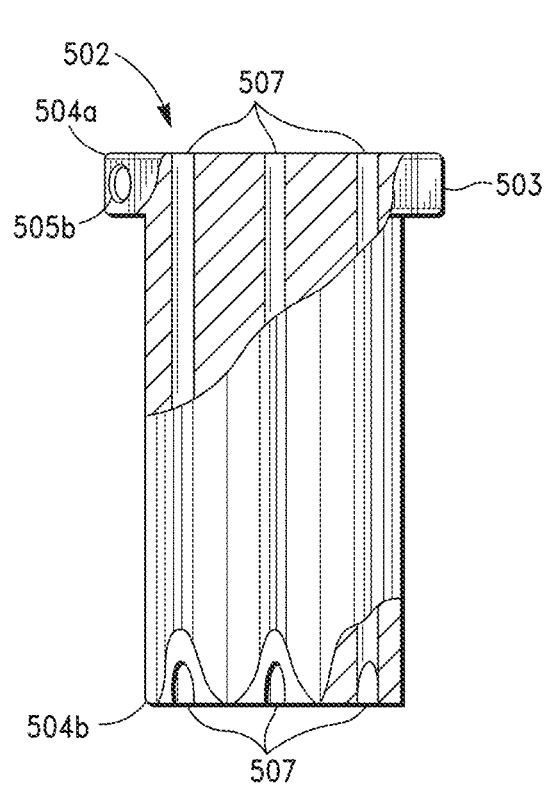
FIG. 9C is a front plan view of the access sleeve shown in FIG. 9B, in accordance with the invention.
Figure 9D:
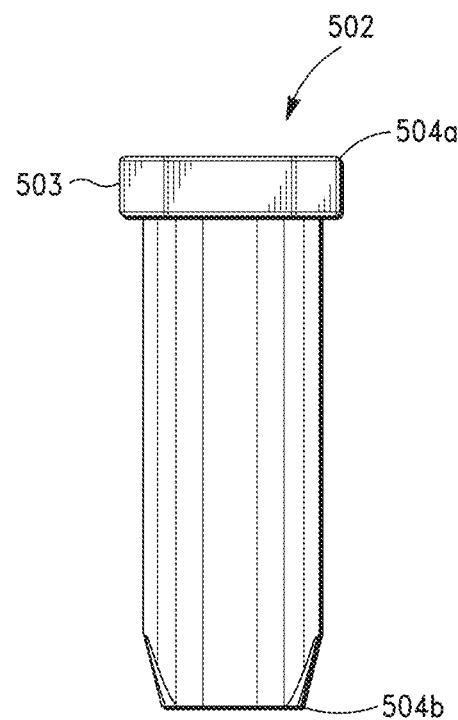
FIG. 9D is a right-side plan view of the access sleeve shown in FIG. 9B, in accordance with the invention.

Referring now to FIGS. 9B-9D, there is shown a preferred embodiment of the access sleeve 502.

As illustrated in FIGS. 9B-9D, the access sleeve 502 comprises proximal and distal ends 504a, 504b, and an internal opening 506 that extends from the proximal end 504a to the distal end 504b of the access sleeve 502, and a plurality of lumens 507, which, as illustrated in FIG. 9A, are sized and configured to receive and position Kirschner wires (K-wires) 509 or similar pin structures therein.

As illustrated in FIG. 9A, the access sleeve internal opening 506 is preferably sized and configured to receive and position the drill guide 520 therein.

As further illustrated in FIGS. 9B and 9D, the proximal end 504a of tire access sleeve 502 comprises a planar region 503, which, as illustrated in FIG. 9A, is configured to seat the proximal end 522a of the drill guide 520 (discussed below) thereon.

In a preferred embodiment, as additionally shown in FIGS. 9B and 9D, the proximal end 504a of the access sleeve 502, i.e., planar region 503, further comprises two (2) threaded holes 505a, 505b, which are preferably disposed on opposing edge regions of the planar region 503. According to the invention, the threaded holes 505a, 505b are sized and configured to receive the threaded end 514 of the access sleeve handle 510, discussed below.

Figure 9E:
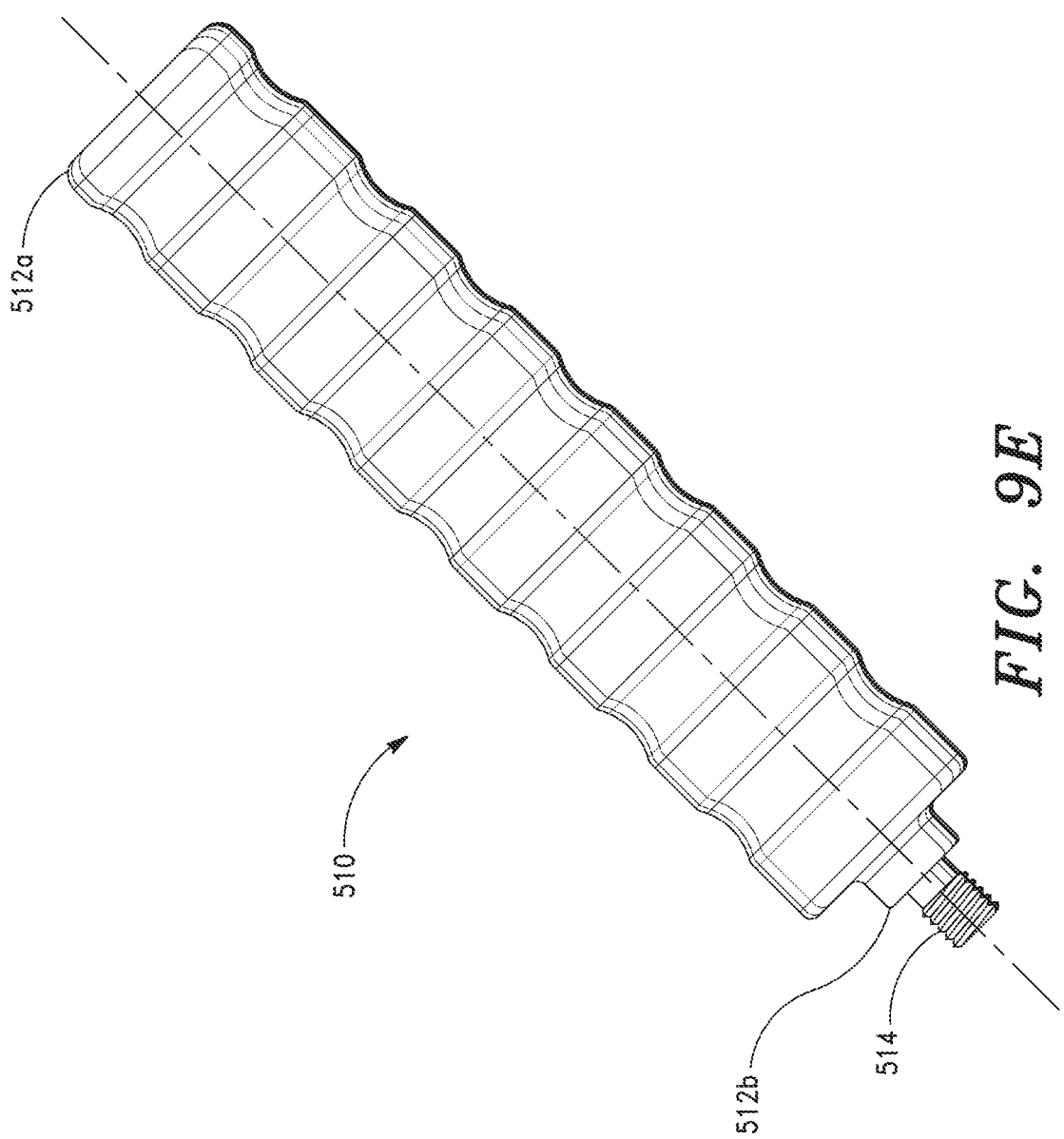
FIG. 9E is a perspective view of one embodiment of an access sleeve handle that is configured to engage the access sleeve shown in FIG. 9B, in accordance with the invention.
Figure 9F:
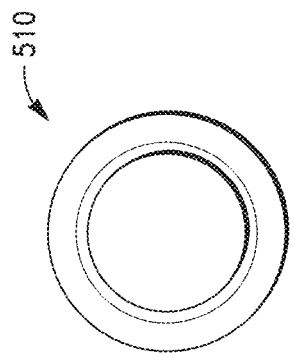
FIG. 9F is an end plan view of the access sleeve handle shown in FIG. 9E, in accordance with the invention.
Figure 9H:
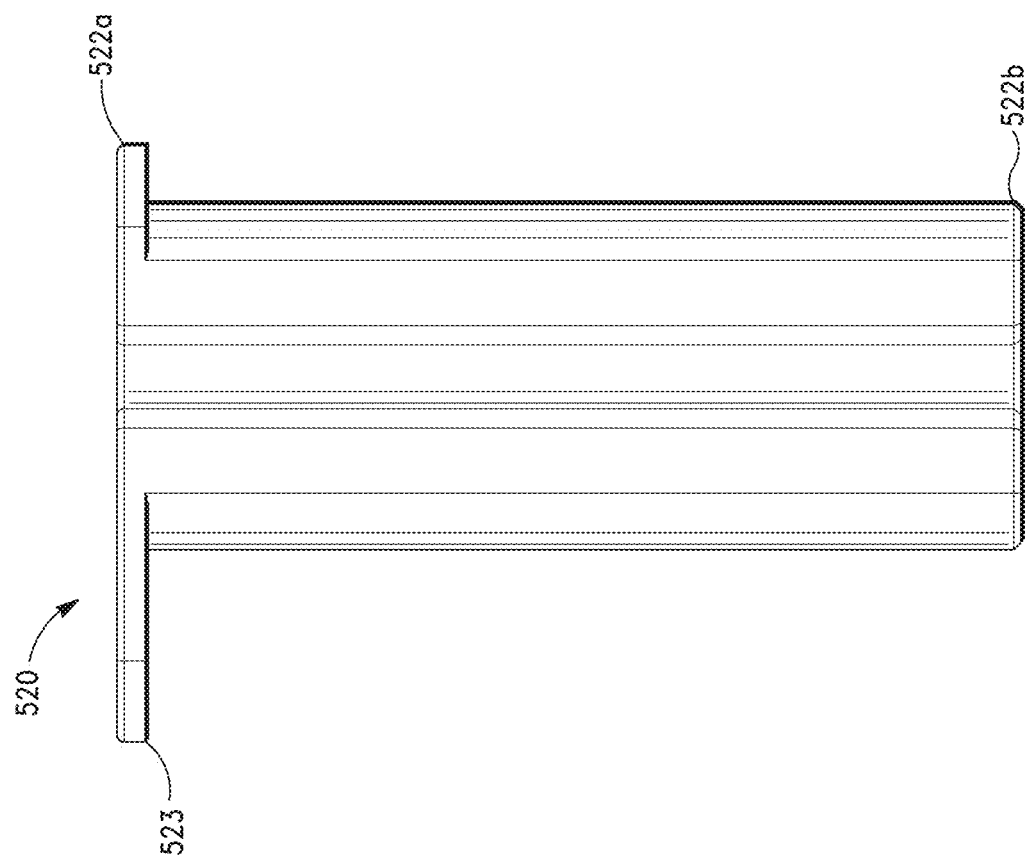
FIG. 9H is a front plan view of the drill guide shown in FIG. 9G, in accordance with the invention.
Figure 9G:
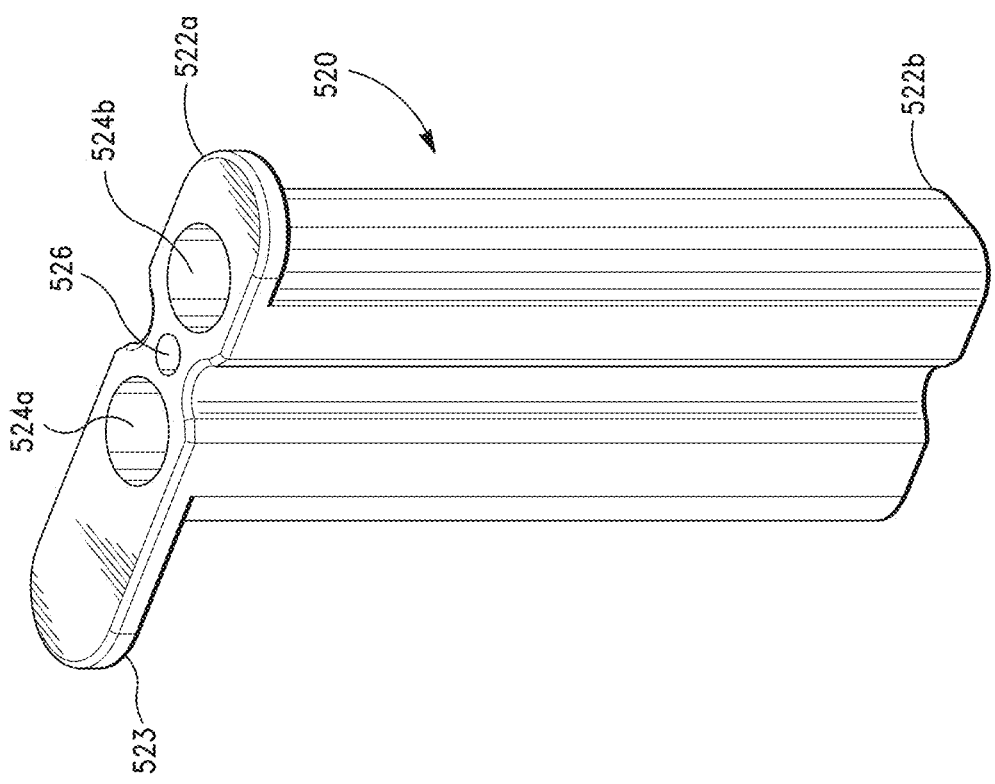
FIG. 9G is a perspective view of the drill guide of the drill guide assembly shown in FIG. 9A, in accordance with the invention.
Figure 9I:
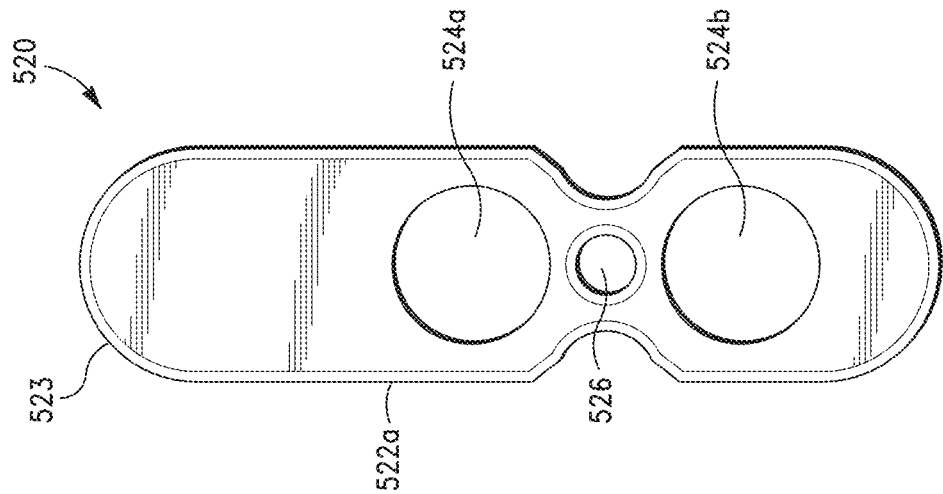
FIG. 9I is a top plan view of the drill guide shown in FIG. 9G, in accordance with the invention.
Figure 9J:
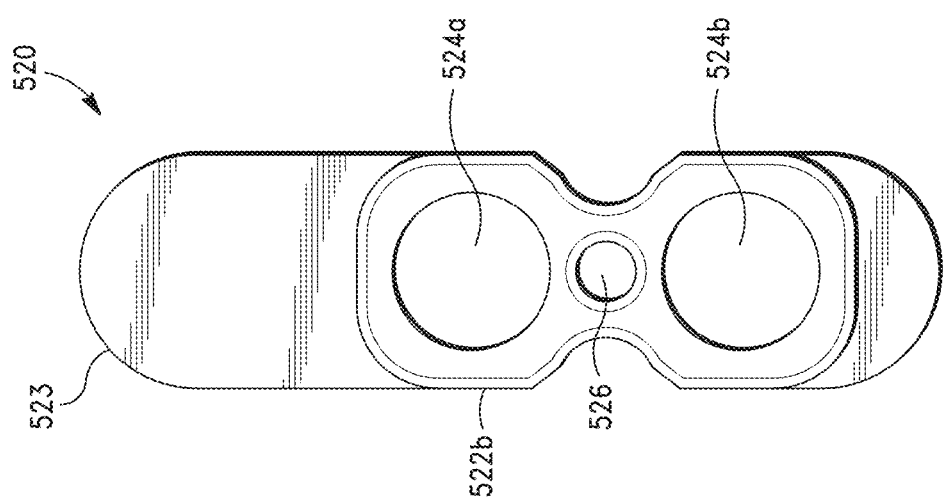
FIG. 9J is a bottom plan view of the drill guide shown in FIG. 9G, in accordance with the invention.

Referring now to FIGS. 9B and 9F, there is shown a preferred embodiment of the access sleeve handle 510.

As illustrated in FIGS. 9E and 9F, tire access sleeve handle 510 preferably comprises an elongated cylindrical shaped member comprising proximal and distal ends 512a, 512b.

As further illustrated in FIG. 9E, in a preferred embodiment, the distal end 512b of the access sleeve handle 510 comprises a threaded extension 514 that is sized and configured to cooperate with the threaded holes 505a, 505b of the access sleeve 502, whereby the access sleeve handle 510 can be threadably engaged to the access sleeve 502.

Referring now to FIGS. 9G-9J, there is shown a preferred embodiment of the drill guide 520.

As illustrated in FIGS. 9E-9J, the drill guide 520 comprises proximal and distal ends 522a, 522b, a pair of drill guide lumens 524a, 524b and a drill guide medial lumen 526; tire drill guide lumens 524a, 524b and drill guide medial lumen 526 extending from the proximal end 522a to the distal end 522b of the drill guide 520.

Figure 9L:
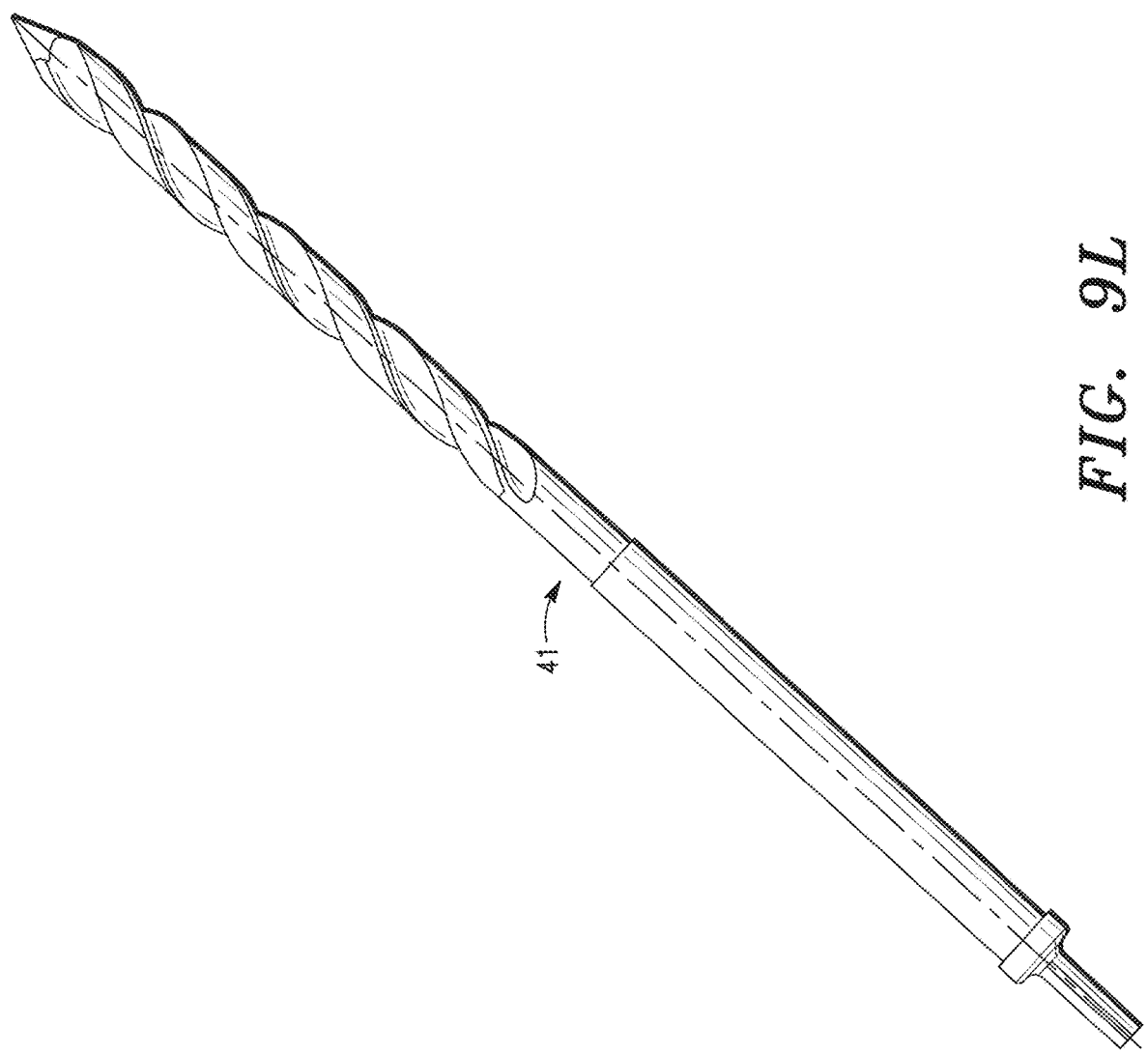
FIG. 9L is a perspective view of the bone dislodging apparatus, i.e., drill bit, shown in FIG. 9A, in accordance with tire invention.

As illustrated in FIG. 9A, in a preferred embodiment, the drill guide lumens 524a, 524b are sized and configured to receive (i) a bone dislodging system 40 of the defect creation assembly 30, in this instance, the drill bit 41 shown in FIG. 9L, and (ii) the guide pin 530 shown in FIG. 9K and discussed below.

In a preferred embodiment, the drill guide medial lumen 526 is sized and configured to receive and guide the elongated guide probe 20 of the invention to a desired position proximate the dysfunctional SI joint.

The drill guide internal lumens 524a, 524b and drill guide medial lumen 526 can also be sized and configured to receive various other suitable instruments, such as surgical scopes, center punches, location pins, drill probes and drill stop assemblies, to facilitate the creation of a pilot SI joint opening.

Referring back to FIGS. 9G and 9H, in a preferred embodiment, the proximal end 522a of the drill guide 520 comprises a planar configuration comprising an extended region 523, which, as illustrated in FIG. 9A, is sized and configured to abut the proximal end 504a of the access sleeve 502 to position the drill guide 520 therein.

Figure 9K:
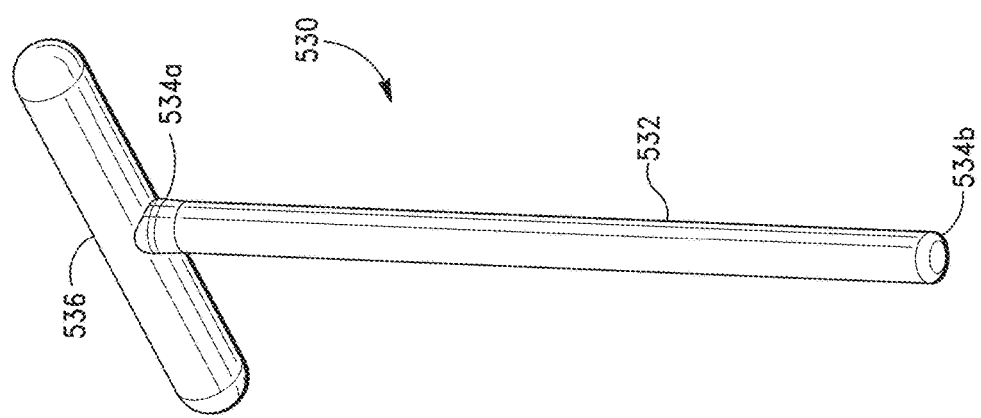
FIG. 9K is a perspective view of the guide pin of the drill guide assembly shown in FIG. 9A, in accordance with the invention.

Referring now to FIG. 9K, there is shown one embodiment of a guide pin 530 of the invention.

As illustrated in FIG. 9K, the guide pin 530 preferably comprises an elongated guide member 532 comprising proximal and distal ends 534a, 534b. The guide pin 530 further comprises a handle 536 that is operatively connected to the proximal end 534a of the guide member 532.

In some embodiments, the system for stabilizing dysfunctional SI joints further comprises a prosthesis extraction assembly 600 that is configured and adapted to remove the prosthesis 70 from the expanded post-prosthesis insertion SI joint opening and, thereby, dysfunctional SI joint.

Referring now to FIGS. 10A-10G, there is shown a preferred embodiment of a prosthesis extraction assembly 600 with prosthesis 70 connected thereto.

Figure 10A:
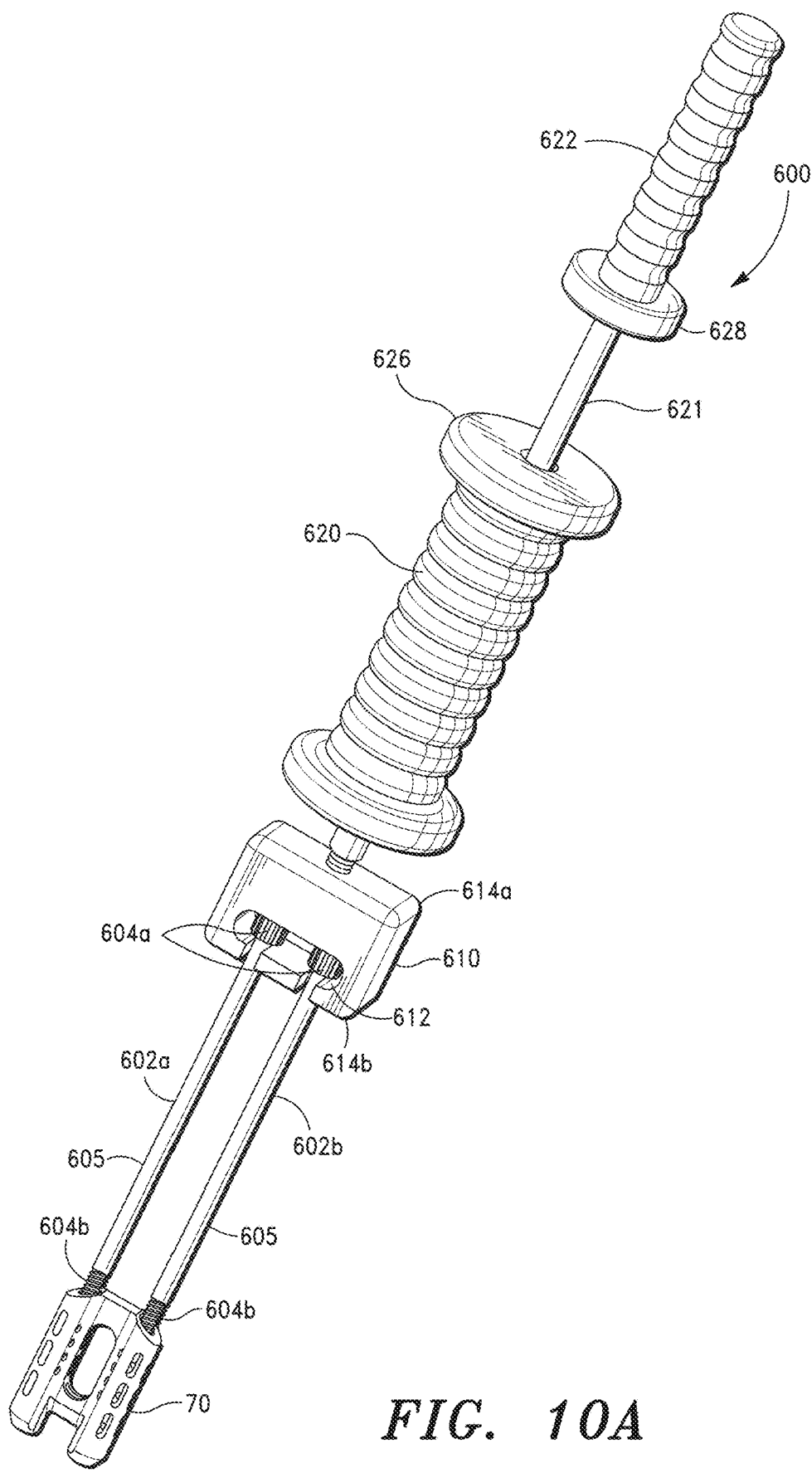
FIG. 10A is a perspective view of one embodiment of a prosthesis extraction assembly, in accordance with the invention.

As illustrated in FIG. 10A, the prosthesis extraction assembly 600 generally comprises prosthesis extraction rods or screws 602a, 602b, an extraction fork 610 and a slap hammer assembly 620.

Figure 10B:
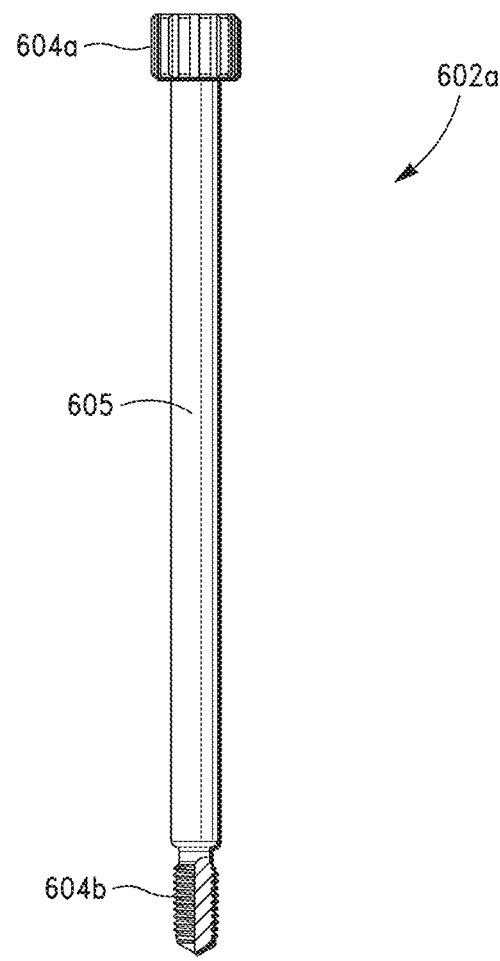
FIG. 10B is a front plan sectional view of the prosthesis extraction rod of the prosthesis extraction assembly shown in FIG. 10A, in accordance with the invention.
Figure 10C:
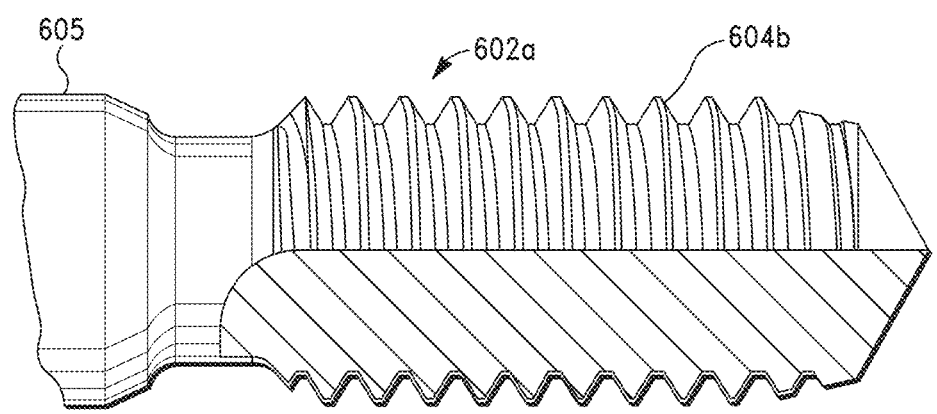
FIG. 10C is a partial section, front sectional plan view of the threaded end of the prosthesis extraction rod shown in FIG. 10B, in accordance with the invention.

As illustrated in FIGS. 10A-10C, the prosthesis extraction rods 602a, 602b comprise elongated rod members 605 comprising capped proximal ends 604a and threaded distal ends 604b, which are sized and configured to threadably engage threaded internal prosthesis engagement lumens 86a, 86b of the prosthesis 70.

Figure 10D:
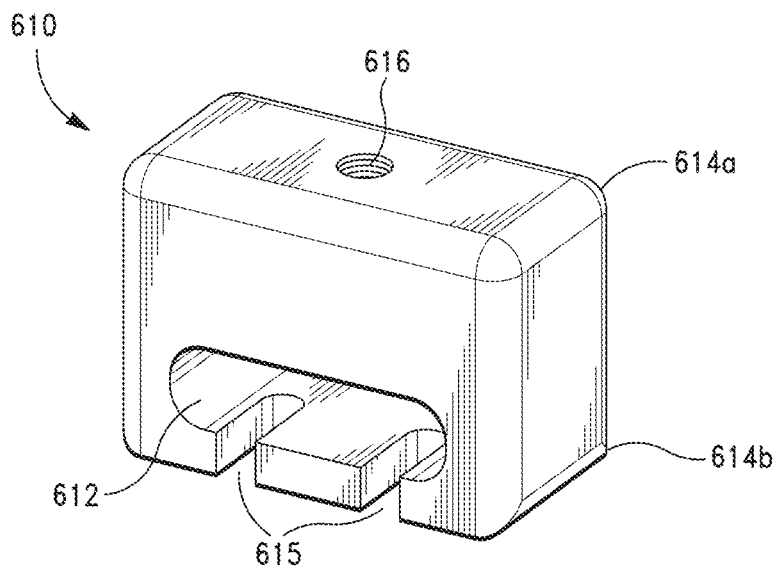
FIG. 10D is a perspective view of the extraction fork of the prosthesis extraction assembly shown in FIG. 10A, in accordance with the invention.
Figure 10E:
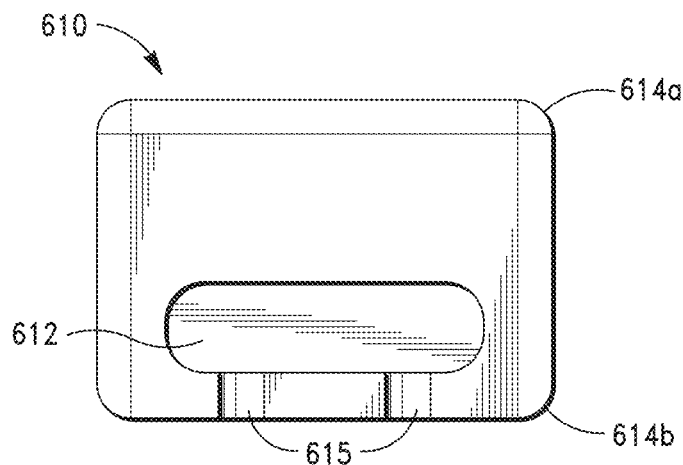
FIG. 10E is a front plan view of the extraction fork shown in FIG. 10D, in accordance with the invention.
Figure 10F:
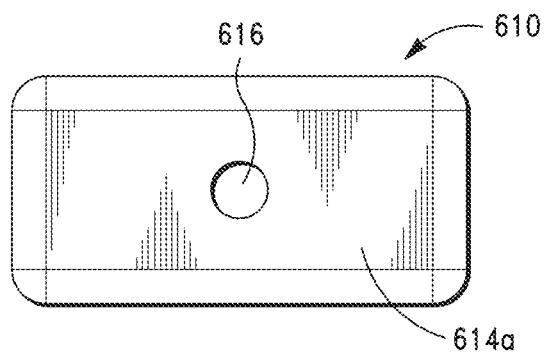
FIG. 10F is a top plan view of the extraction fork shown in FIG. 10D, in accordance with the invention.

As illustrated in FIGS. 10D-10F, the extraction fork 610 comprises proximal and distal ends 614a, 614b, a primary recess 612 and secondary recesses 615 proximate the distal end 614b. The extraction fork 610 further comprises a threaded lumen 616 proximate the proximal end 614a, which, as discussed below, is sized and configured to threadably engage the threaded distal end 624b of the elongated rod member 621 of the slap hammer assembly 620 discussed below.

As illustrated in FIG. 10A, in a preferred embodiment, the secondary recesses 615 of the extraction fork 610 are configured to receive and releasably engage or ensnare the capped proximal ends 604a of the prosthesis extraction rods 602a, 602b.

As further illustrated in FIG. 10A, the extraction fork 610 is further configured to releasably engage the threaded distal end 624b of the slap hammer assembly 620 via the threaded lumen 616.

Figure 10G:
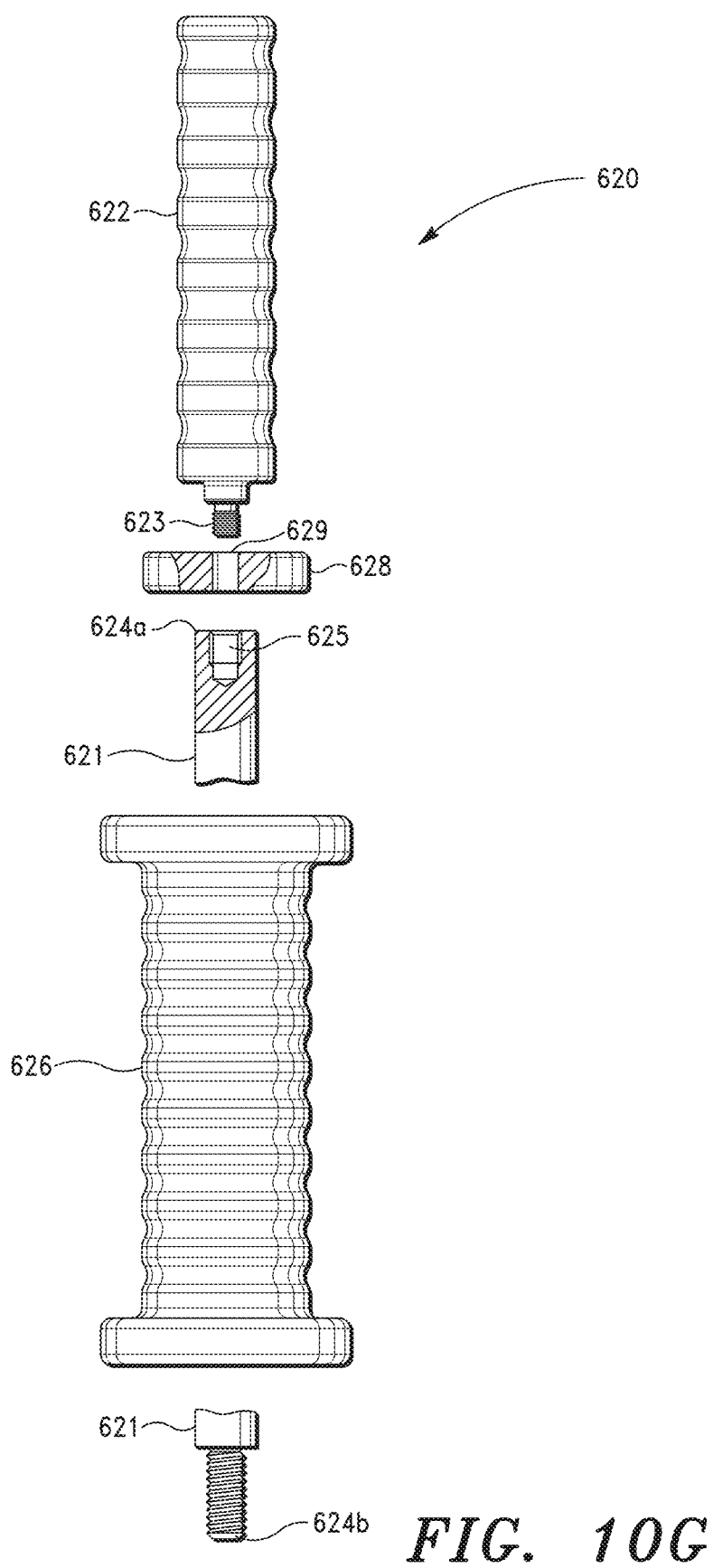
FIG. 10G is an exploded view of the slap hammer assembly of the prosthesis extraction assembly shown in FIG. 10A, in accordance with the invention.

As illustrated in FIGS. 10A and 10G, the slap hammer assembly 620 comprises a handle 622, an elongated rod member 621, a weighted sleeve member 626 and a bump stop 628.

As illustrated in FIG. 10G, the elongated rod member 621 comprises a proximal end 624a, comprising internal threads 625, and a threaded distal end 624b.

As further illustrated in FIG. 10G, the handle 622 comprises threaded distal end 623, which, as illustrated in FIG. 10A, is sized and configured to threadably engage the proximal end 624a of the elongated rod member 621.

As illustrated in FIG. 10A, the threaded distal end 623 of the handle 622 is further sized and configured to receive and seat the bump stop 628 thereon, wherein the bump stop 628 is securely positioned between the handle 622 and elongated rod member 621 when the handle 622 is engaged to the elongated rod member 621.

In a preferred embodiment, the weighted sleeve member 626 is configured to slidably translate along the elongated rod member 621 and abut the proximal end 614a of the extraction fork 610 and bump stop 628 when the slap hammer assembly 620 is releasably engaged to the extraction fork 610.

According to the invention, removal of prosthesis 70 from the expanded post-prosthesis insertion SI joint opening is achieved as follows:

the prosthesis extraction rods 602a, 602b are initially connected to prosthesis 70; and after the prosthesis extraction rods 602a, 602b are connected to prosthesis 70, the surgeon grips the handle 622 of the prosthesis extraction assembly 600 and forcibly abuts the handle 622 against the bump stop 628, wherein a removal or extraction force is exerted on prosthesis 70 via the prosthesis extraction rods 602a, 602b and the prosthesis 70 is released from the expanded post-prosthesis insertion SI joint opening.

Examples

The following example is provided to enable those skilled in the art to more clearly understand and practice the present invention. The example should not be considered as limiting the scope of the invention, but merely as being illustrated as representative thereof.

An adult male, age 42 presented with a traumatic injury proximate the SI joint, resulting in a dysfunctional SI joint and significant pain associated therewith, i.e., a visual analog pain score (VAS) of approximately 8.0.

A CT scan was initially performed to determine the full extent of the patient's injury, check for any SI joint abnormalities and plan the stabilization procedure, including the prosthesis required to stabilize the dysfunctional SI joint.

The stabilization procedure was performed in accord with the method set forth in Co-pending U.S. application Ser. No. 17/463,779; specifically, ¶¶[000258]-[000261] thereof. The specifics of the procedure were as follows:

Prosthesis

The prosthesis selected for the procedure was similar to prosthesis 70 illustrated in FIGS. 6A-6H and described in detail above. The prosthesis comprised a length of 30 mm and the elongated partially cylindrical sections, i.e., barrels, of the prosthesis comprised a diameter of 7.5 mm. The prosthesis was sourced from Applicant, i.e., Tenon Medical, Inc., and referred to as a CATAMARAN SIJ Fixation System™.

The prosthesis included a bone graft material, which was placed in the barrels of the prosthesis after the prosthesis was implanted in the dysfunctional SI joint.

Posterior Inferior Surgical Approach

The initial incision was placed along the lateral lip of the posterior third of the iliac crest to the posterior superior spine, which provided a prosthesis entry point into the dysfunctional SI joint through the posterior ligaments at approximately the S3 level. The trajectory of the prosthesis was toward the mid-point of the S1 end plate and the sacral promontory.

Creation of Pilot SI Joint Opening

The pilot SI joint opening was created with the defect creation assembly shown in FIGS. 3B and 3C, and described above. The bone dislodging apparatus of the assembly comprised a drill assembly and associated drill bit.

The pilot SI joint opening was similar to pilot SI joint opening 200 described above. The pilot SI joint opening was created by drilling a first opening in the sacrum bone structure and a second opening in the ilium bone structure (such as shown in FIG. 48) with the drill assembly.

Radiological Assessment

Figure 11A:
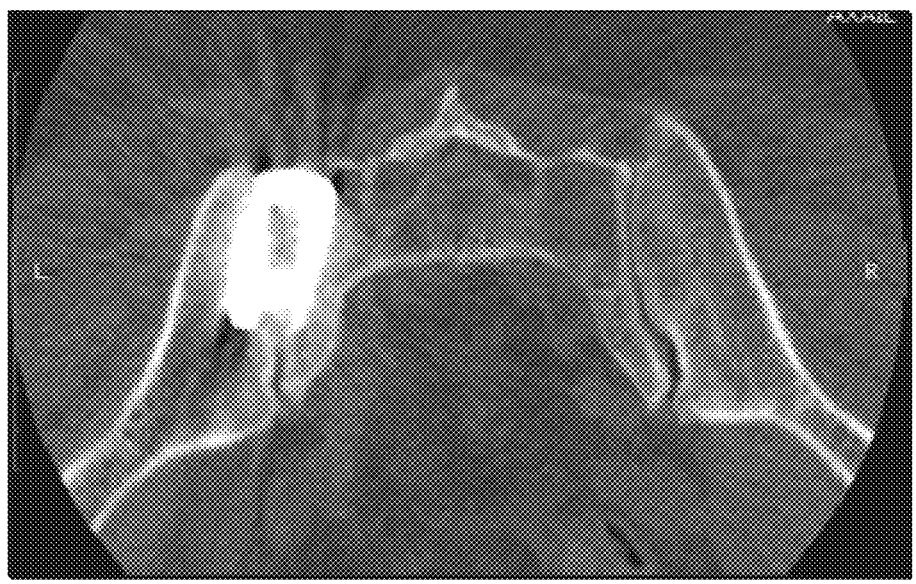
FIGS. 11A and 11B are CT scan images of a patient's SI joint at six (6) months following an SI joint stabilization procedure with the prosthesis shown in FIG. 6A, in accordance with the invention.
Figure 11B:
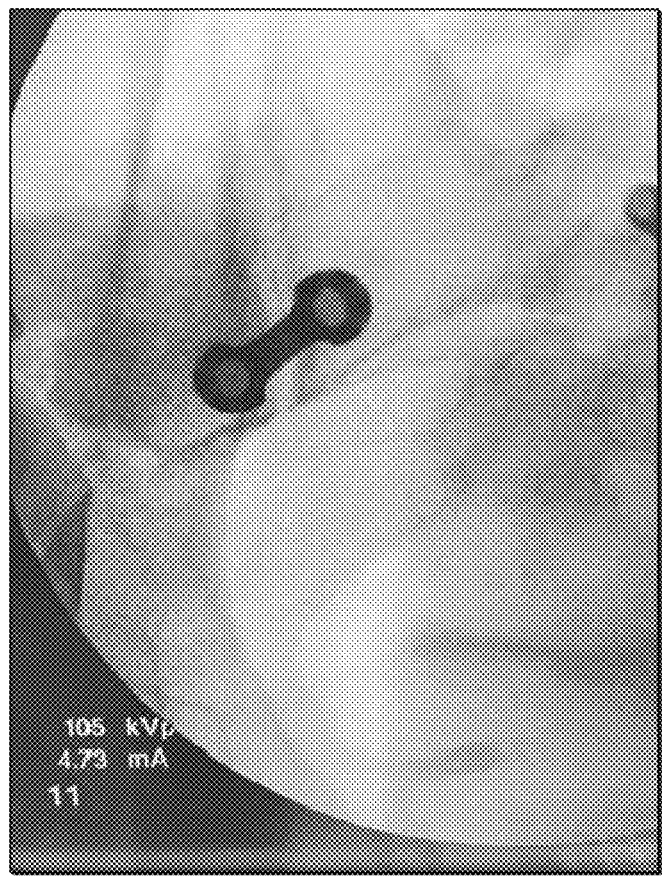

CT scan images of the patient's SI joint six (6) months after the SI joint stabilization procedure, which are shown in FIGS. 11A and 11B, reflect (i) secure and proper placement of the prosthesis in the SI joint, (ii) substantial solid bridging of osseous tissue, and, hence, bone across the SI joint and, (iii) substantial ossification around tire prosthesis.

Post-Procedure SI Joint Pain Relief and Function

Figure 12:
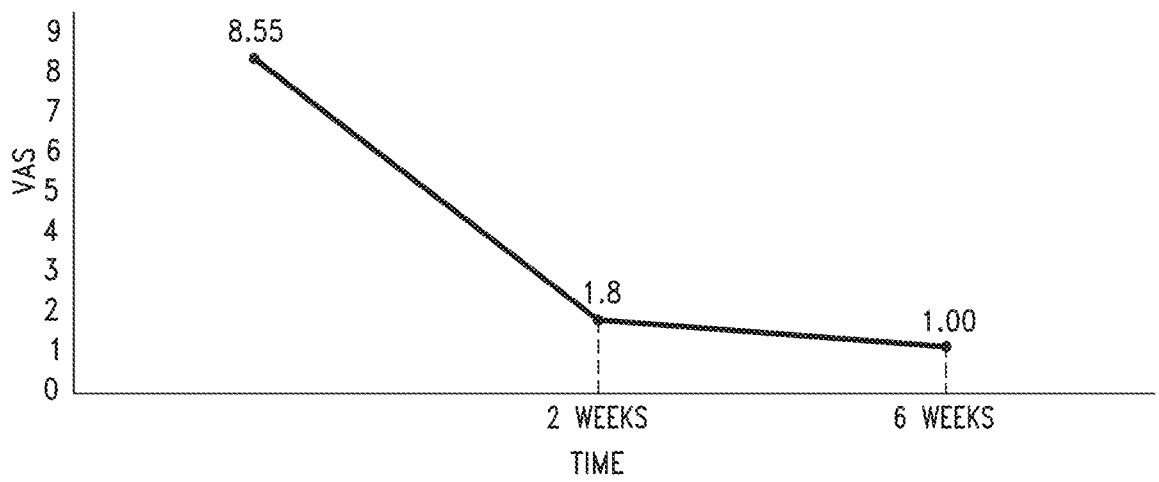
FIG. 12 is a graphical illustration of a patient's visual analog pain score over a six (6) week period of time following an SI joint stabilization procedure with the prosthesis shown in FIG. 6A, in accordance with the invention.

After a recovery period of fourteen (14) days, tire patient reported that the pain had been substantially reduced. Indeed, as shown in FIG. 12, fourteen (14) days after the procedure a visual analog pain score (VAS) of 1.8 was achieved.

The patient was also subjected to a series of post procedure tests to determine the stability of the SI joint and mobility of the musculoskeletal structures of the pelvic and lumbar regions proximate the SI joint. The results were very favorable. The patient tested positive to the flexion abduction and external rotation (FABER) test. The patient also responded very favorably to Gaenslen, thigh thrust, compression and distraction tests.

The tests thus confirmed that the post procedure SI joint was stabilized and that the musculoskeletal structures of the pelvic and lumbar regions proximate thereto were restored to a near normal level.

As will readily be appreciated by one having ordinary skill in the art, the present invention provides numerous advantages compared to prior art methods and apparatus for stabilizing dysfunctional SI joints. Among the advantages are the following:

the provision of improved SI joint stabilization systems and apparatus, which can be readily employed in minimally-invasive SI joint stabilization procedures to stabilize dysfunctional SI joints via a posterior approach;

the provision of improved SI joint prostheses, which, when implanted in a dysfunctional SI joint, effectively ameliorate pain associated with tire SI joint dysfunction;

the provision of improved SI joint prostheses, which can readily be employed in minimally-invasive SI joint stabilization procedures and provide secure engagement to SI joint structures.

the provision of improved SI joint prostheses, which can readily be employed in minimally-invasive SI joint stabilization procedures and possess optimal structural properties to effectively stabilize dysfunctional SI joints; and the provision of improved SI joint prostheses, which can readily be employed in minimally-invasive SI joint stabilization methods and facilitate remodeling of damaged osseous tissue and regeneration of new osseous tissue and osseous tissue structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An implant for stabilizing a dysfunctional sacroiliac (SI) joint, said dysfunctional SI joint comprising a sacrum bone structure, an ilium bone structure and an intraarticular region between said sacrum and ilium bone structures, said implant comprising:

a hollow monolithic member configured and adapted to be advanced into said dysfunctional SI joint in a posterior trajectory, said monolithic member comprising a first elongated section, a second elongated section, and a bridge section, said bridge section disposed between and not extending beyond said first elongated section and said second elongated section in any direction, whereby said monolithic member comprises a first bridge/elongated section interface proximate said first elongated section and a second bridge/elongated section interface proximate said second elongated section, said monolithic member further comprising an outer surface and a first longitudinal axis, said first elongated section configured to be advanced into said sacrum bone structure when said monolithic member is said advanced into said dysfunctional SI joint in said posterior trajectory, said second elongated section configured to be advanced into said ilium bone structure when said monolithic member is said advanced into said dysfunctional SI joint in said posterior trajectory, said bridge section configured to be advanced into said intraarticular region of said dysfunctional SI joint when said monolithic member is said advanced into said dysfunctional SI joint in said posterior trajectory, said first elongated section comprising a first open proximal end, a first distal end, and a first plurality of slots, said first elongated section further comprising a first elongate lumen, extending from said first open proximal end to said first distal end and a second plurality of slots disposed in said first bridge/elongated section interface of said monolithic member, said first plurality of slots and said second plurality of slots in communication with said first elongate lumen of said first elongated section, said first elongated section further comprising a first tapered region disposed on said first distal end, said second elongated section comprising a second open proximal end, a second distal end, and a third plurality of slots, said second elongated section further comprising a second elongate lumen extending from said second open proximal end to said second distal end and a fourth plurality of slots disposed in said second bridge/elongated section interface of said monolithic member, said third plurality of slots and said fourth plurality of slots in communication with said second elongate lumen of said second elongated section, said second elongated section further comprising a second tapered region disposed on said second distal end, said bridge section comprising a second longitudinal axis, a first proximal end and a third distal end, said bridge section further comprising an elongate opening disposed between said first proximal end and said third distal end of said bridge section and extending through said bridge section, said elongate opening being in communication with said second plurality of slots and, thereby said first elongate lumen and said first plurality of slots of said first elongated section, and said fourth plurality of slots and, thereby said second elongate lumen and third plurality of slots of said second elongated section, said bridge section further comprising a third tapered region disposed on said third distal end, said third tapered region comprising a gradually decreasing thickness along said second longitudinal axis of said bridge section, said second longitudinal axis of said bridge section being coincident with said first longitudinal axis of said monolithic member, said monolithic member further comprising an osteogenic composition comprising poly(glycerol-co-sebacate) acrylate (PGSA), said osteogenic composition comprising a flowable state and a solid elastomer state, said osteogenic composition disposed in at least one of said first elongate lumen of said first elongated section and said second elongate lumen of said second elongated section in said flowable state, said monolithic member configured and adapted to allow said osteogenic composition to flow out of said at least one of said first elongate lumen of said first elongated section and said second elongate lumen of said second elongated section in said flowable state when said monolithic member is said advanced into said dysfunctional SI joint, whereby said osteogenic composition is in communication with said outer surface of said monolithic member and said at least one of said sacrum bone structure and said ilium bone structure of said dysfunctional SI joint, said monolithic member further adapted to stabilize said dysfunctional SI joint and induce remodeling of damaged bone tissue of said at least one of said sacrum bone structure and said ilium bone structure of said dysfunctional SI joint when said monolithic member is said advanced into said dysfunctional SI joint.

2. The implant of claim 1, wherein said osteogenic composition is adapted to transition from said flowable state to said solid elastomer state upon application of radiation energy.

3. The implant of claim 2, wherein said radiation energy comprises ultraviolet (UV) light radiation in the range of 10-400 nm.

4. The implant of claim 2, wherein, when said osteogenic composition is in communication with said outer surface of said monolithic member and said osteogenic composition is subjected to said application of radiation energy, whereby said osteogenic composition transitions to said solid elastomer state, said osteogenic composition configured to facilitate engagement of said monolithic member to said at least one of said sacrum bone structure and said ilium bone structure of said dysfunctional SI joint.

5. The implant of claim 1, wherein said osteogenic composition further comprises a bone morphogenic protein (BMP) selected from the group consisting of BMP-1, BMP2a, BMP2b, BMP3, BMP4, BMP5, BMP6, BMP7 and BMP8a.

6. The implant of claim 1, wherein said osteogenic composition further comprises an antibiotic selected from the group consisting of penicillin, gentamicin, vancomycin and rifampin.

7. The implant of claim 1, wherein said osteogenic composition further comprises an anti-inflammatory selected from the group consisting of dexamethasone, betamethasone, prednisone and ibuprofen.

* * * * *